US012611625B2

(12) United States Patent
Lim et al.

(10) Patent No.: US 12,611,625 B2
(45) Date of Patent: Apr. 28, 2026

(54) AIR CLEANER

(71) Applicant: SAMSUNG ELECTRONICS CO., LTD., Suwon-si (KR)

(72) Inventors: Youngseok Lim, Suwon-si (KR);
Nakhyun Kim, Suwon-si (KR);
Juyoung Kim, Suwon-si (KR);
Taeyong Lee, Suwon-si (KR); Euysung Chu, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 282 days.

(21) Appl. No.: 18/383,309

(22) Filed: Oct. 24, 2023

(65) Prior Publication Data

US 2024/0207766 A1 Jun. 27, 2024

Related U.S. Application Data

(63) Continuation of application No. PCT/KR2023/015459, filed on Oct. 6, 2023.

(51) Int. Cl.
B01D 46/00 (2022.01)
A61L 9/20 (2006.01)

(52) U.S. Cl.
CPC ........... B01D 46/0004 (2013.01); A61L 9/20 (2013.01); B01D 46/0028 (2013.01); B01D 46/0041 (2013.01); B01D 46/0047 (2013.01); A61L 2209/12 (2013.01); A61L 2209/14 (2013.01); B01D 2265/024 (2013.01)

(58) Field of Classification Search
None
See application file for complete search history.

(56) References Cited

U.S. PATENT DOCUMENTS 10,139,118 B2 * 11/2018 Law ................... B01D 46/0045
10,967,319 B2 4/2021 Chu et al.
(Continued)

FOREIGN PATENT DOCUMENTS

KR 10-0660138 B1 12/2006
KR 20-2008-0003197 8/2008
(Continued)

OTHER PUBLICATIONS

Translation of KR-101955571-B1 (Year: 2018).*
(Continued)

*Primary Examiner* — Brit E. Anbacht
(74) *Attorney, Agent, or Firm* — STAAS & HALSEY LLP

(57) ABSTRACT

An air cleaner including a first housing including a first suction port and a first discharge port; a first fan inside the first housing; a coupling duct on an upper portion of the first housing; a second housing including a second suction port and a second discharge port; a second fan inside the second housing; and a coupling base on a lower portion of the second housing and including a guide surface sloping outwardly in an upward direction, wherein the coupling base is separably couplable to the coupling duct. When the coupling base and coupling duct are coupled, a portion of air discharged through the first discharge port is guided by the guide surface and discharged outside of the second housing, and when the coupling base and coupling duct are separated, air is guided by the guide surface into the second housing.

15 Claims, 25 Drawing Sheets

(56)  References Cited

U.S. PATENT DOCUMENTS

| | | | |
|---|---|---|---|
| 11,223,162 B2 | 1/2022 | So et al. | |
| 11,752,461 B2 | 9/2023 | Jeon et al. | |
| 2005/0172816 A1* | 8/2005 | Son .................... | B01D 46/0013 |
| | | | 96/417 |
| 2017/0246579 A1 | 8/2017 | Mun et al. | |
| 2019/0160411 A1* | 5/2019 | Chu ................... | H01R 13/2421 |
| 2020/0298161 A1* | 9/2020 | Jeon ................... | B01D 46/0008 |
| 2022/0011009 A1 | 1/2022 | Lee et al. | |
| 2022/0184540 A1 | 6/2022 | Park et al. | |
| 2024/0207766 A1* | 6/2024 | Lim ......................... | F24F 8/22 |

FOREIGN PATENT DOCUMENTS

| | | | | |
|---|---|---|---|---|
| KR | 10-0891128 B1 | 4/2009 | | |
| KR | 10-0943328 B1 | 2/2010 | | |
| KR | 10-1192846 B1 | 10/2012 | | |
| KR | 10-1685170 B1 | 12/2016 | | |
| KR | 10-1707333 B1 | 2/2017 | | |
| KR | 10-1796291 B1 | 11/2017 | | |
| KR | 10-1803267 B1 | 12/2017 | | |
| KR | 10-1826236 B1 | 2/2018 | | |
| KR | 10-2019-0000114 | 1/2019 | | |
| KR | 10-2019-0059729 A | 5/2019 | | |
| KR | 10-1955571 | 5/2019 | | |
| KR | 101955571 B1 * | 5/2019 | ............. | B01D 46/44 |
| KR | 10-2019-0061138 | 6/2019 | | |
| KR | 10-2019-0077703 A | 7/2019 | | |
| KR | 10-2020-0112595 | 10/2020 | | |
| KR | 10-2224629 B1 | 3/2021 | | |
| KR | 10-2021-0110526 A | 9/2021 | | |
| KR | 10-2330840 B1 | 11/2021 | | |
| KR | 10-2022-0083530 A | 6/2022 | | |
| KR | 10-2022-0161239 | 12/2022 | | |

OTHER PUBLICATIONS

International Search Report dated Jan. 26, 2024 for International Application No. PCT/KR2023/015459.
Written Opinion of the International Searching Authority dated Jan. 26, 2024 for International Application No. PCT/KR2023/015459.
Extended European Search Report dated Oct. 2, 2025 for European Application No. 23912480.3.

* cited by examiner

617

AIR CLEANER

CROSS-REFERENCE TO RELATED APPLICATIONS

This application is a continuation application, under 35 U.S.C. § 111(a), of International Application No. PCT/KR2023/015459, filed on Oct. 6, 2023, which claims priority under 35 U.S.C. § 119 to Korean Patent Application 10-2022-0186485, filed on Dec. 27, 2022, in the Korean Intellectual Property Office, the disclosures of which are incorporated by reference herein in their entireties.

TECHNICAL FIELD

The present disclosure relates to an air cleaner, and more specifically, to an air cleaner in which a sterilization unit is separable from a cleaning unit.

BACKGROUND ART

An air cleaner is a device used to remove contaminants from air. The air cleaner may remove odor-causing chemicals such as bacteria, viruses, molds, and particulates present in the drawn air.

The air cleaner may include a suction port configured to suction contaminated air, a discharge port configured to discharge purified air, and a blower fan configured to cause a flow of air.

A filter configured to purify contaminated indoor air may be provided in the air cleaner. Air drawn into the air cleaner may be purified into clean air as contaminants are removed from the air while the air passes through the filter, and the purified air may be discharged to the outside of the air cleaner.

An air passage along which air flows from the suction port toward the discharge port may be formed in the air cleaner. The air passage of the air cleaner may be provided in various ways according to the purpose of operation of the air cleaner. The shapes, positions, and the like of the suction port and the discharge port may be determined in various ways in consideration of the shape of the air passage.

DISCLOSURE

Technical Problem

Therefore, it is an aspect of the present disclosure to provide an air cleaner including a structure in which a sterilization unit is separable from a cleaning unit.

It is an aspect of the present disclosure to provide an air cleaner including a structure in which a sterilization unit is separately usable by being separated from a cleaning unit.

It is an aspect of the present disclosure to provide an air cleaner having passages each improved for a structure in which a sterilization unit is coupled to a cleaning unit and a structure in which a sterilization unit is separated from a cleaning unit and separately usable.

Aspects of the present disclosure are not limited to those mentioned above, and other unmentioned aspects should be clearly understood by those of ordinary skill in the art to which the present disclosure pertains from the description below.

According to an embodiment of the disclosure, an air cleaner includes a first housing including a first suction port, and a first discharge port; a first fan inside the first housing; a dust collector filter inside the first housing; a coupling duct on an upper portion of the first housing; a second housing including a second suction port, and a second discharge port; a second fan inside the second housing; a light source inside the second housing to emit ultraviolet rays onto air drawn into the second housing through the second suction port; and a coupling base on a lower portion of the second housing, the coupling base including a guide surface sloping outwardly of the second housing in an upward direction. The coupling base is separably couplable to the coupling duct so that, when the coupling base is coupled to the coupling duct, a portion of the air discharged through the first discharge port is guided by the guide surface to be discharged to an outside of the second housing, and when the coupling base is separated from the coupling duct, the air drawn into the second suction port is guided by the guide surface into the second housing.

According to an embodiment of the disclosure, the guide surface may include a guide hole communicating with the second suction port. When the coupling base is separated from the coupling duct, the air drawn into the second suction port may pass through the guide hole.

According to an embodiment of the disclosure, the guide hole may extend along the guide surface of the coupling base, from a lower portion of the guide surface toward an upper portion of the guide surface.

According to an embodiment of the disclosure, the coupling base may include a lower end of the guide surface configured to be supported on a floor when the coupling base is separated from the coupling duct. The guide hole may extend upward from the lower end of the guide surface.

According to an embodiment of the disclosure, the coupling base may include a connection surface extending from the lower end of the guide surface toward an inside of the guide surface, the connection surface configured to be supported by the coupling duct when the coupling base is coupled to the coupling duct. At least a portion of the guide hole may extend along the connection surface.

According to an embodiment of the disclosure, the coupling base may include a base holder having a hollow and including a coupling protrusion protruding downward and extending in a circumferential direction relative to the hollow. The coupling duct may include a coupling plate having an insertion hole into which the coupling protrusion is insertable.

According to an embodiment of the disclosure, the insertion hole may extend in a circumferential direction of the coupling plate so that the coupling protrusion is rotatable with respect to the coupling plate.

According to an embodiment of the disclosure, the coupling duct may include a fixing portion configured to cover an upper side of the coupling protrusion to fix the coupling protrusion when the coupling protrusion is inserted into the insertion hole and rotated.

According to an embodiment of the disclosure, the air cleaner may further include a first housing cover configured to be couplable to the coupling duct to cover an upper side of the first housing when the coupling base is separated from the coupling duct.

According to an embodiment of the disclosure, the first housing cover may include a cover plate, and a coupling protrusion protruding downward from the cover plate and couplable to the coupling duct.

According to an embodiment of the disclosure, the air cleaner may further include a first air cleaning unit including the first housing, the first fan, the dust collector filter, the coupling duct, and a first connection terminal; and a second air cleaning unit including the second housing, the second fan, the light source, the coupling base, and a second connection terminal. The first connection terminal and the second connection terminal may be electrically connected to each other when the coupling base is coupled to the coupling duct.

According to an embodiment of the disclosure, the coupling base may include an inner surface located inside of the guide surface, and on which the guide hole is formed, such that the second connection terminal is mounted on the inner surface. The first connection terminal may be disposed at the coupling duct to be connected to the second connection terminal when the coupling base is coupled to the coupling duct.

According to an embodiment of the disclosure, the second housing may include a power connector configured to supply the second fan and the light source with power when the coupling base is separated from the coupling duct.

According to an embodiment of the disclosure, the coupling base may be configured to be supported on a floor when the coupling base is separated from the coupling duct.

According to an embodiment of the disclosure, the first housing may have a cylindrical shape. The second housing may have a cylindrical shape with a diameter smaller than a diameter of the first housing.

DESCRIPTION OF DRAWINGS

These and/or other embodiments of the disclosure will become apparent and more readily appreciated from the following description of embodiments, taken in conjunction with the accompanying drawings of which.

4

Figure 12:
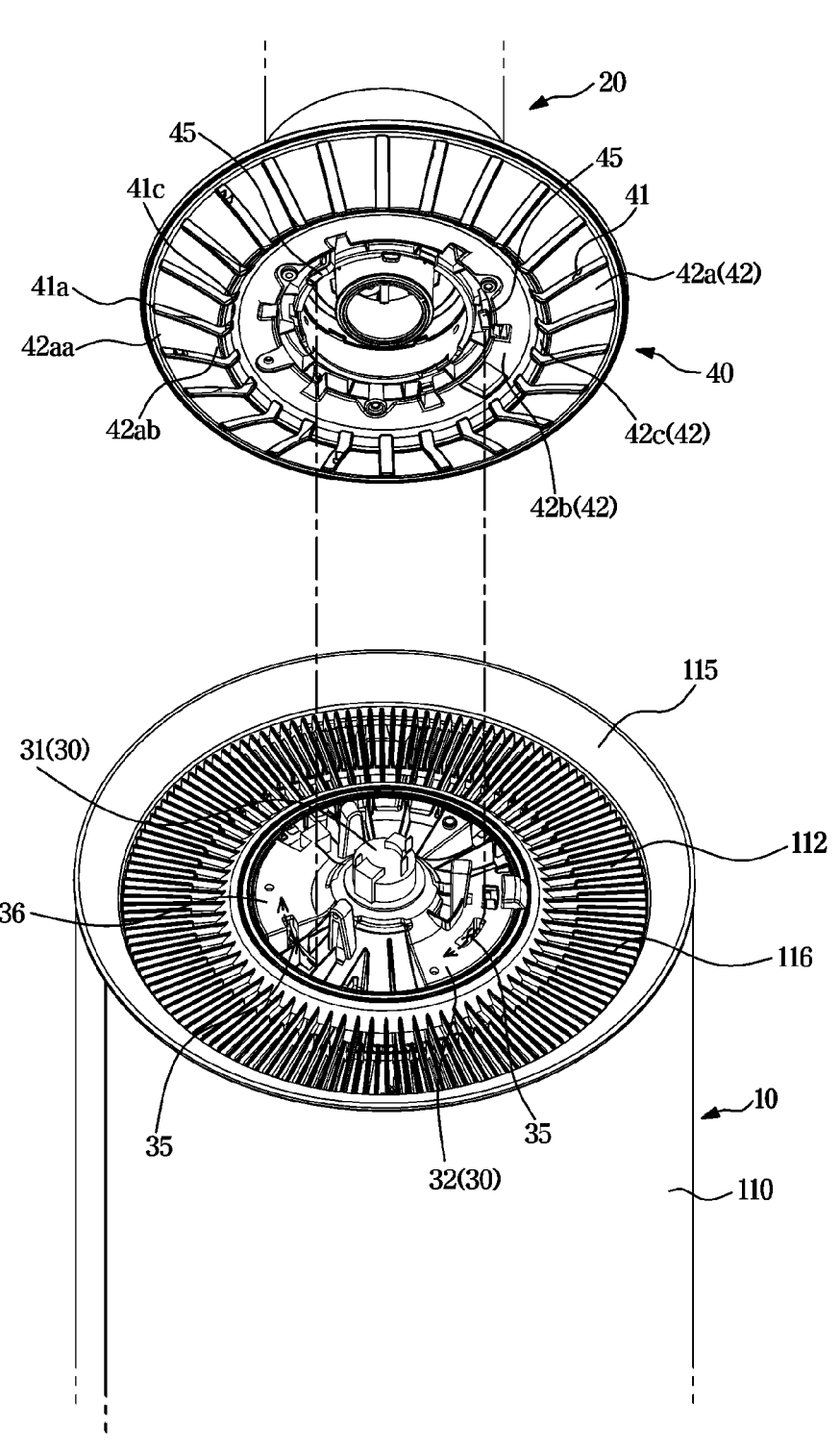

FIG. 12 is a view illustrating a bottom of a second air cleaning unit and a perspective appearance of a first air cleaning unit of the air cleaner according to an embodiment of the present disclosure.

Figure 13:
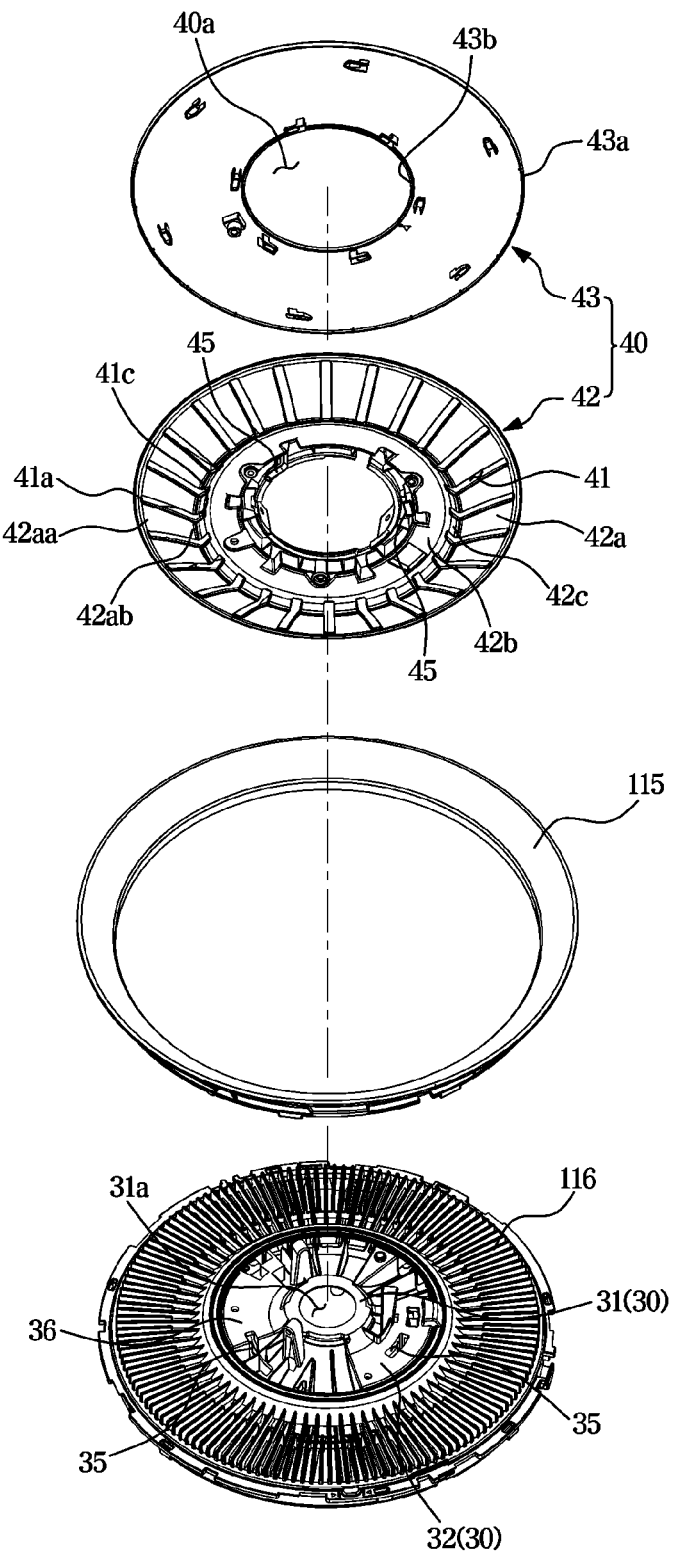

FIG. 13 is a view illustrating a base cover, a base holder, a first upper cover, and a coupling duct of the air cleaner according to an embodiment of the present disclosure.

Figure 14:
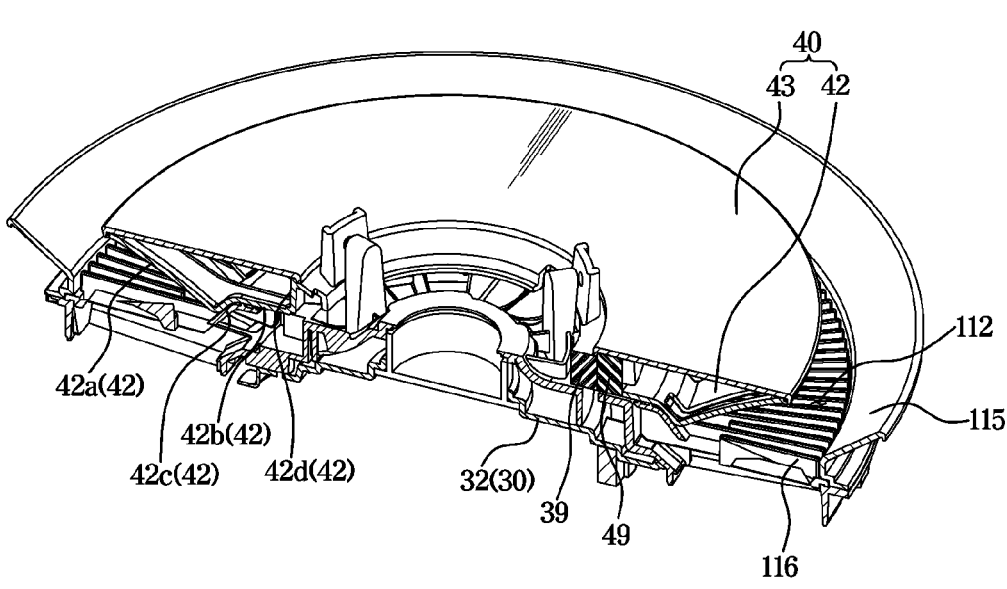

FIG. 14 is a cross-sectional perspective view illustrating a coupled state of the base cover, the base holder, the first upper cover, and the coupling duct shown in FIG. 13.

Figure 15:
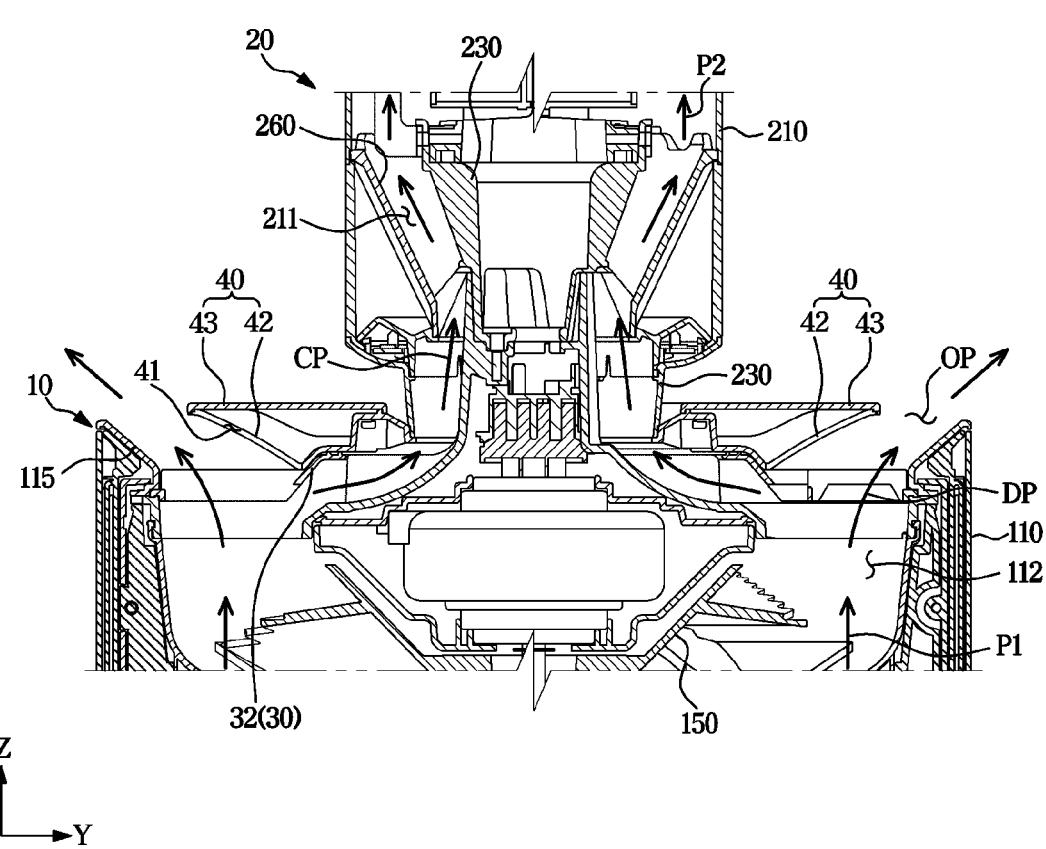

FIG. 15 is an enlarged cross-sectional view illustrating an enlarged cut-out of a partial configuration of the air cleaner according to an embodiment of the present disclosure.

Figure 16:
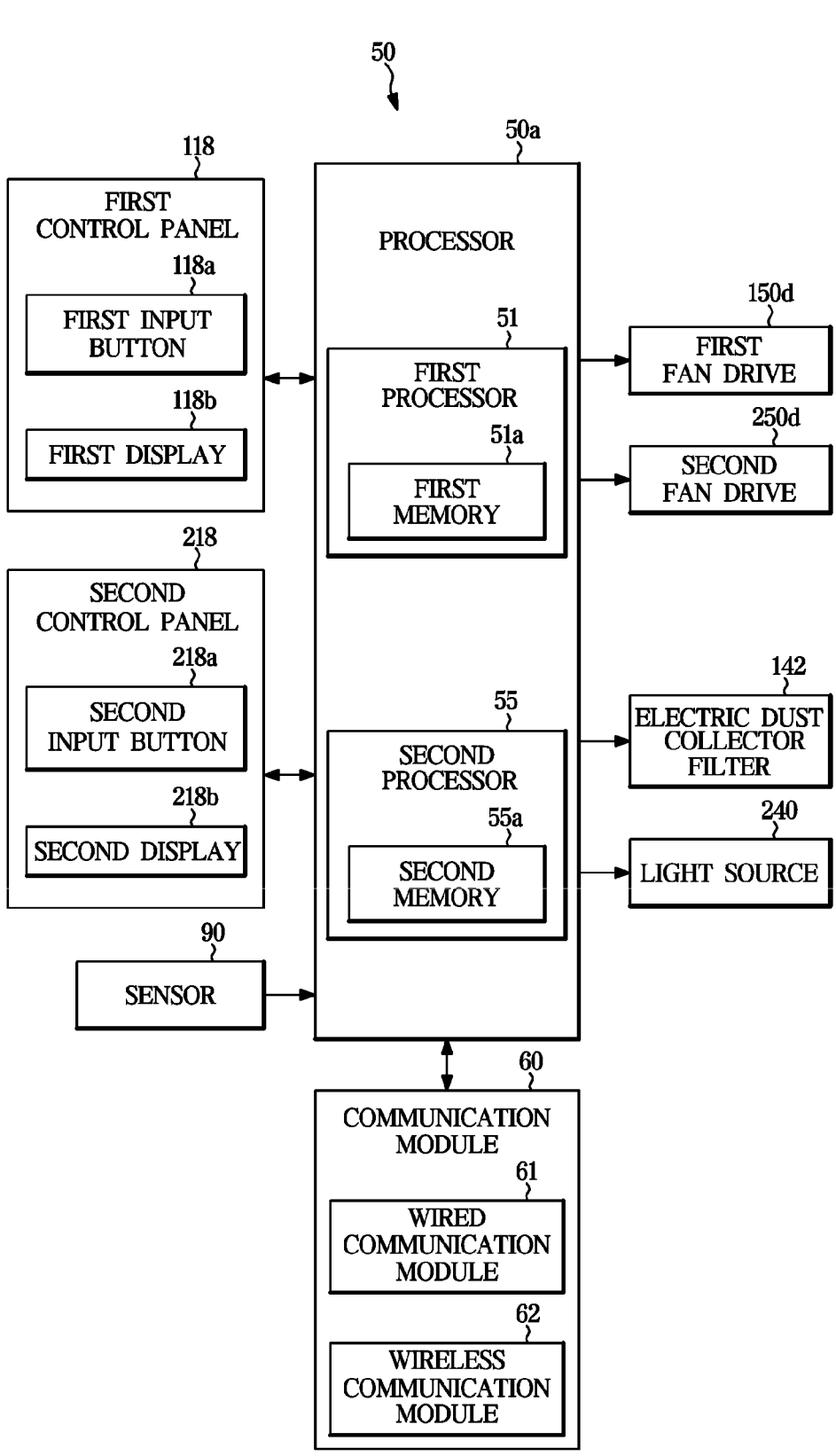

FIG. 16 is a block diagram illustrating a configuration of the air cleaner according to an embodiment of the present disclosure.

Figure 17:
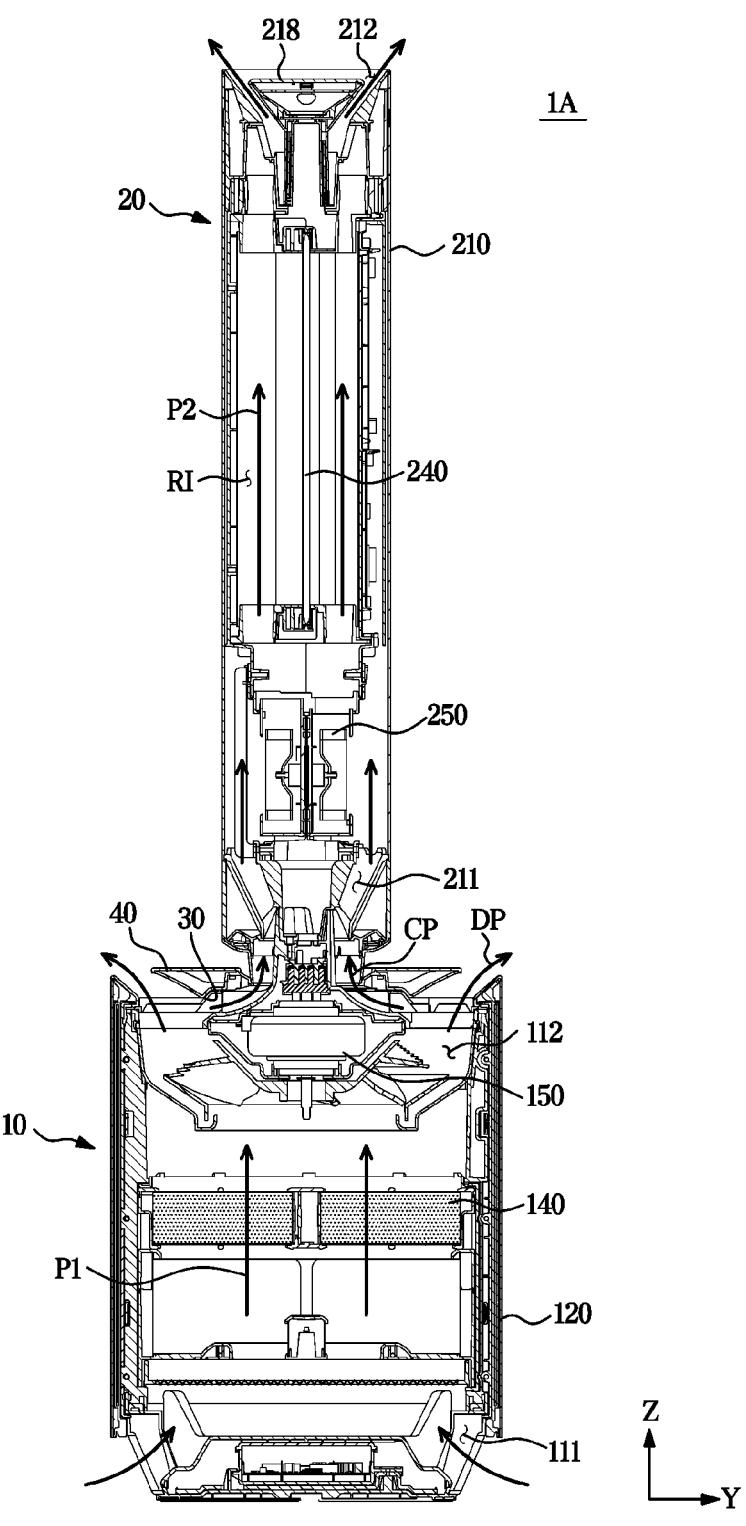

FIG. 17 is a cross-sectional side view illustrating an operation according to a first mode when a first air cleaning unit and a second air cleaning unit are coupled to each other according to an embodiment of the present disclosure.

Figure 18:
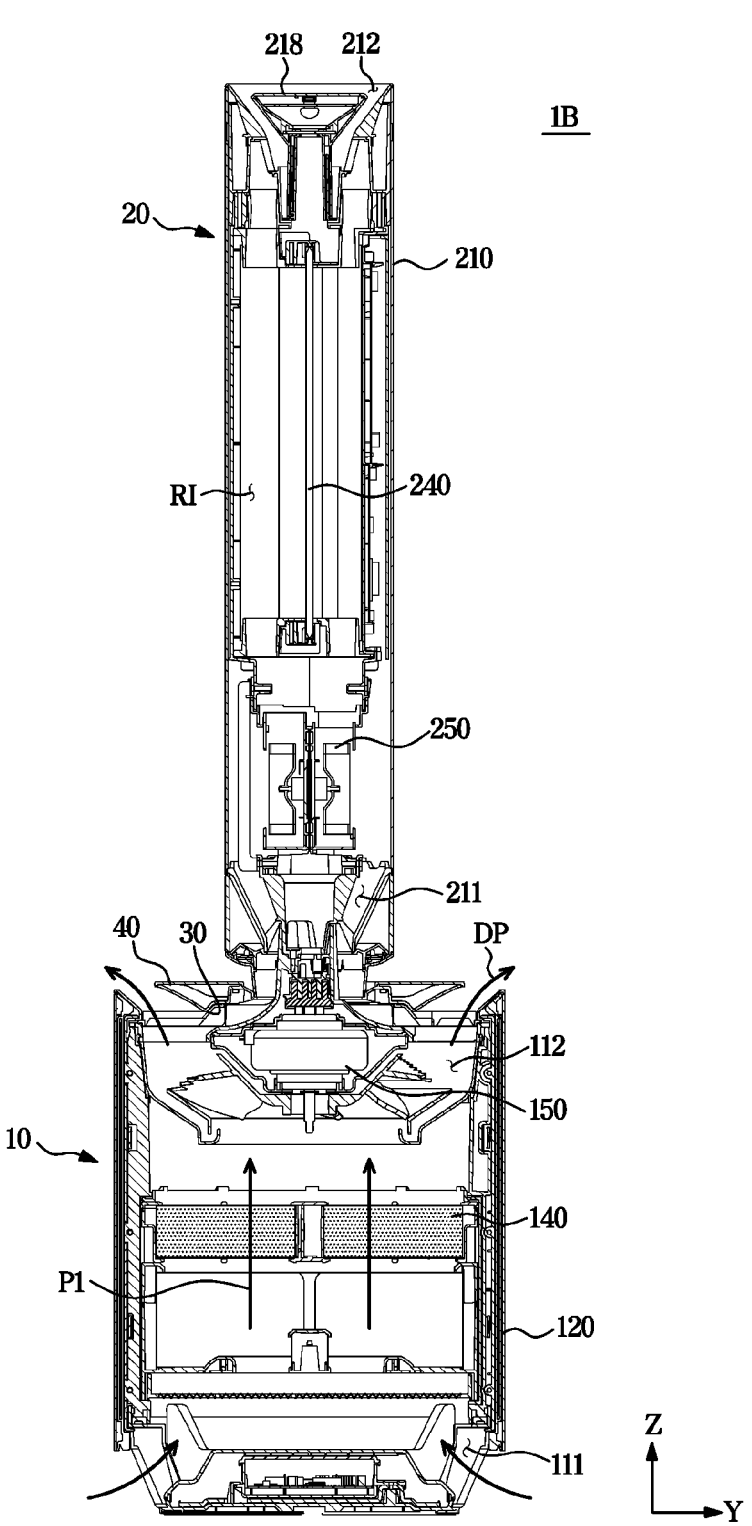

FIG. 18 is a cross-sectional side view illustrating an operation according to a second mode when a first air cleaning unit and a second air cleaning unit are coupled to each other according to an embodiment of the present disclosure.

Figure 19:
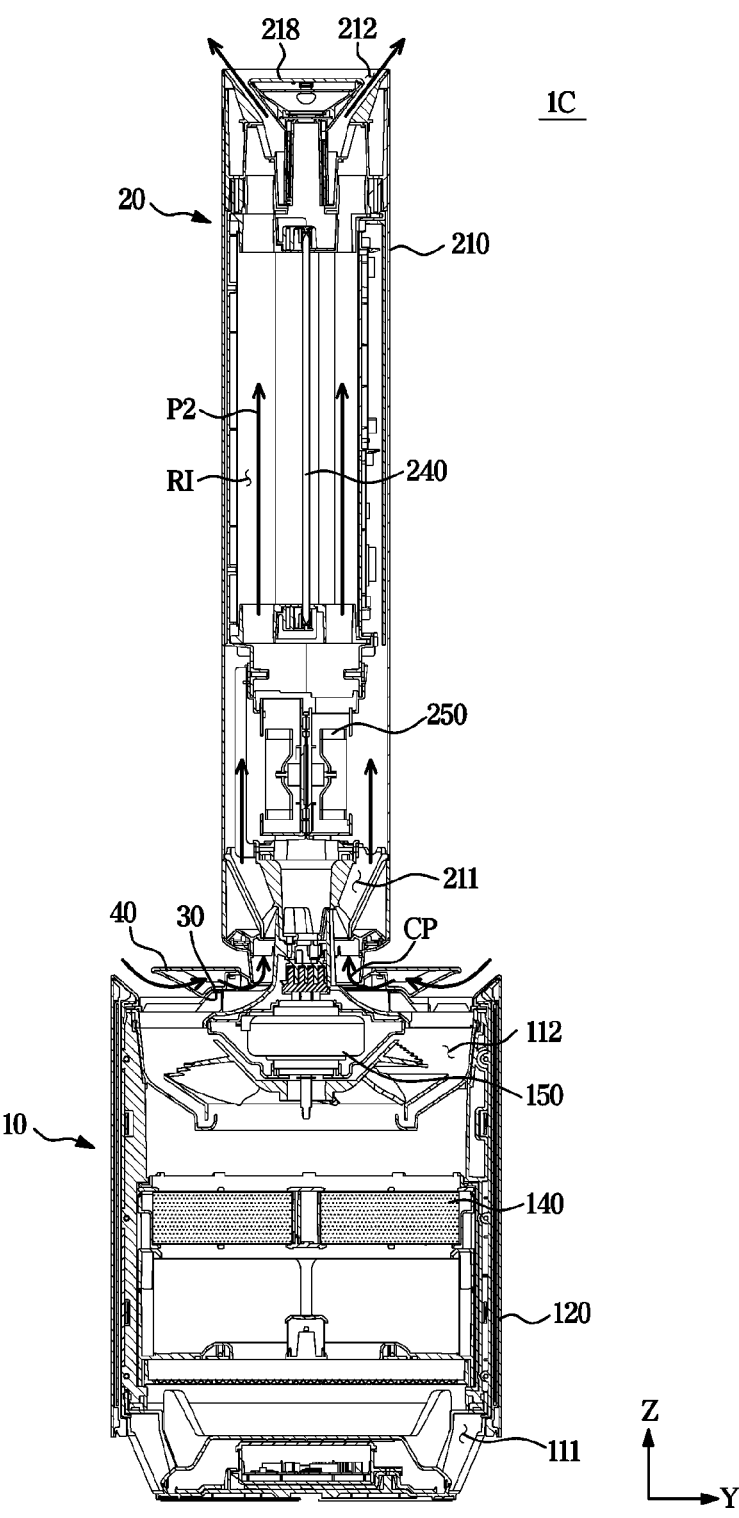

FIG. 19 is a cross-sectional side view illustrating an operation according to a third mode when a first air cleaning unit and a second air cleaning unit are coupled to each other according to an embodiment of the present disclosure.

Figure 20:
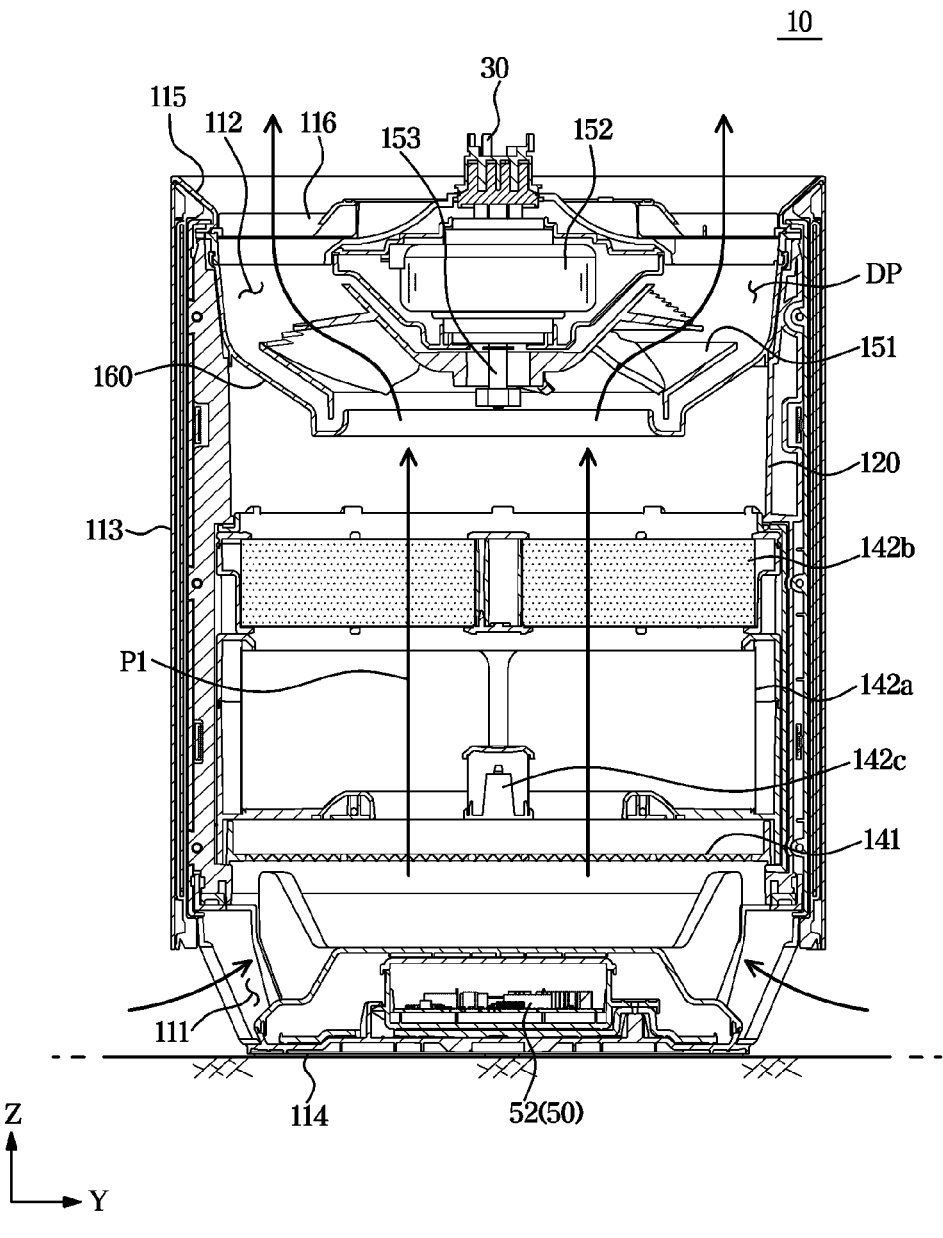

FIG. 20 is a side cross-sectional view of a first air cleaning unit of an air cleaner according to an embodiment of the present disclosure.

Figure 21:
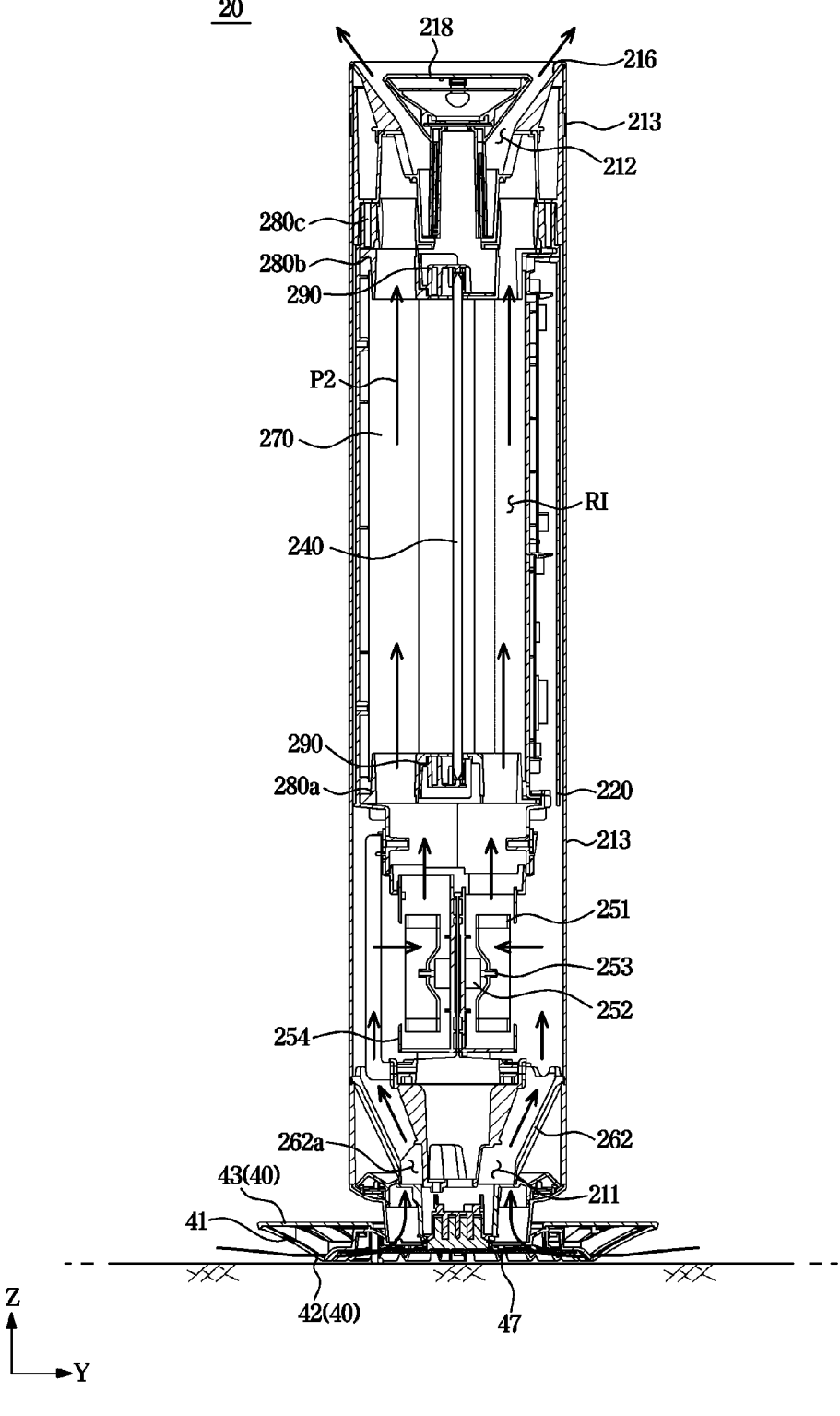

FIG. 21 is a side cross-sectional view of a second air cleaning unit of an air cleaner according to an embodiment of the present disclosure.

Figure 22:
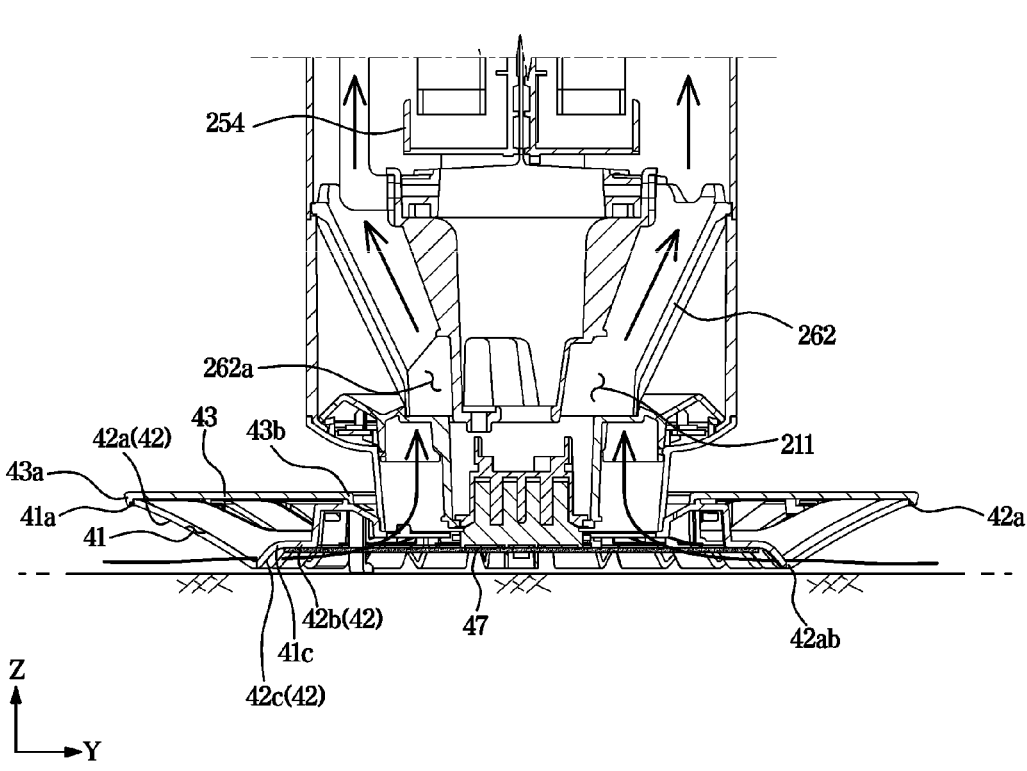

FIG. 22 is a cross-sectional view illustrating external air being introduced through a guide hole of a second air cleaning unit of the air cleaner according to an embodiment of the present disclosure.

Figure 23:
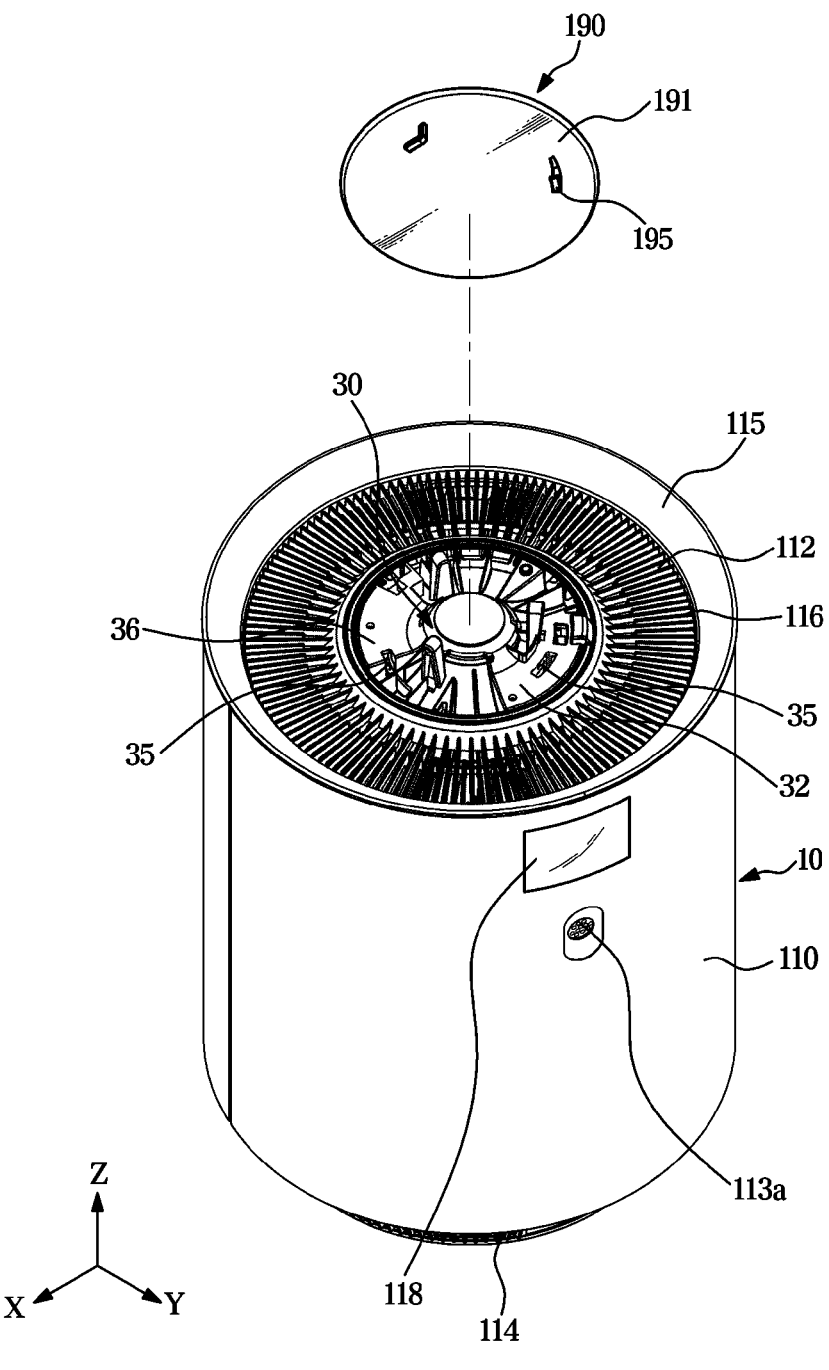

FIG. 23 is a view illustrating appearances of a first air cleaning unit and a first housing cover of the air cleaner according to an embodiment of the present disclosure.

Figure 24:
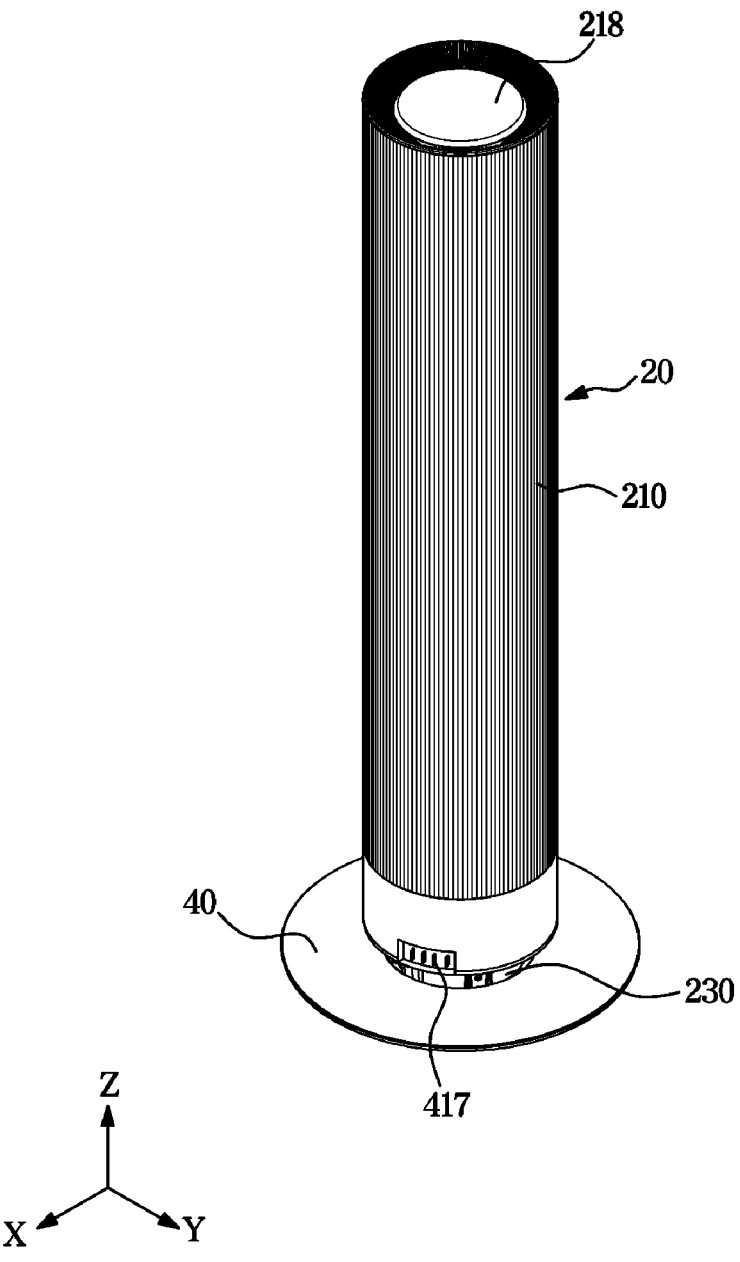

FIG. 24 is a perspective view of a second air cleaning unit including an open type pin according to an embodiment of the present disclosure.

Figure 25:
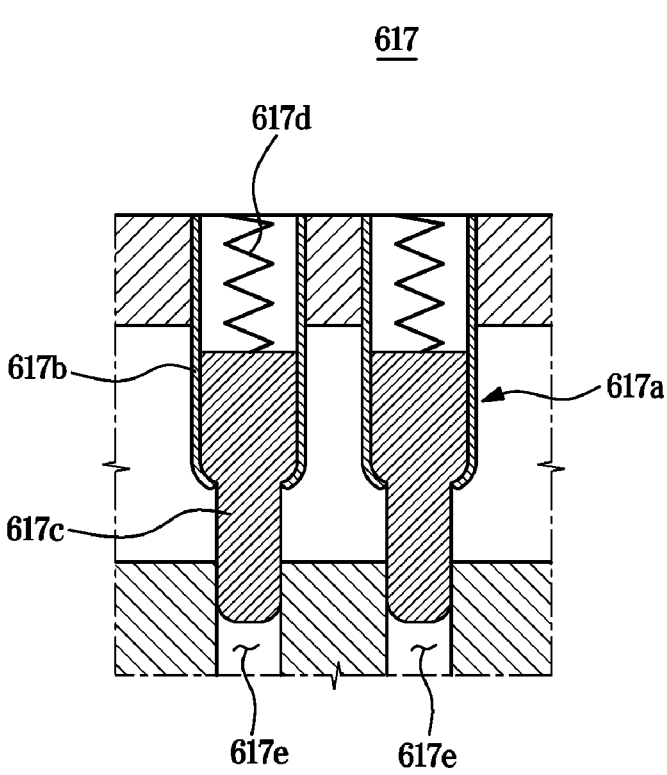

FIG. 25 is a cross-sectional view of a pogo pin structure according to an embodiment of the present disclosure.

MODES OF THE DISCLOSURE

Embodiments described herein and configurations illustrated in the drawings are merely exemplary embodiments of the present disclosure, and various modifications which may replace the embodiments and the drawings herein may be present at the time of filing this application.

Also, like reference numerals or symbols presented in the drawings of the application indicate parts or elements that perform substantially the same functions.

Also, terms used herein are for describing the embodiments and are not intended to limit and/or restrict the disclosure. A singular expression includes a plural expression unless context clearly indicates otherwise. In the application, terms such as "include" or "have" are for designating that features, numbers, steps, operations, elements, parts, or combinations thereof are present, and do not preclude the possibility of presence or addition of one or more other features, numbers, steps, operations, elements, parts, or combinations thereof in advance.

Also, terms including ordinals such as "first" and "second" used herein may be used to describe various elements, but the elements are not limited by the terms, and the terms are only used for the purpose of distinguishing one element from another element. For example, a first element may be referred to as a second element while not departing from the scope of rights of the present disclosure, and likewise, a second element may also be referred to as a first element. The term "and/or" includes a combination of a plurality of associated listed items or any one item among the plurality of associated listed items.

Meanwhile, terms such as "up-down direction," "lower side," and "front-lower direction" used in the following description are defined based on the drawings, and the shape and position of each element are not limited by the terms.

The terms "portion," "module," "member," and "block" used in the following description may be implemented using software or hardware, and according to embodiments, a plurality of "portions," "modules," "members," or "blocks" may be implemented as a single element, or a single "portion," "module," "member," or "block" may include a plurality of elements.

In the following description, when a certain portion is described as being "connected" to another portion, this includes a case in which the certain portion is indirectly connected to the other portion as well as a case in which the certain portion is directly connected to the other portion, and the indirect connection includes connection through a wireless network.

Hereinafter, embodiments according to the present disclosure will be described in detail with reference to the accompanying drawings.

Figure 1:
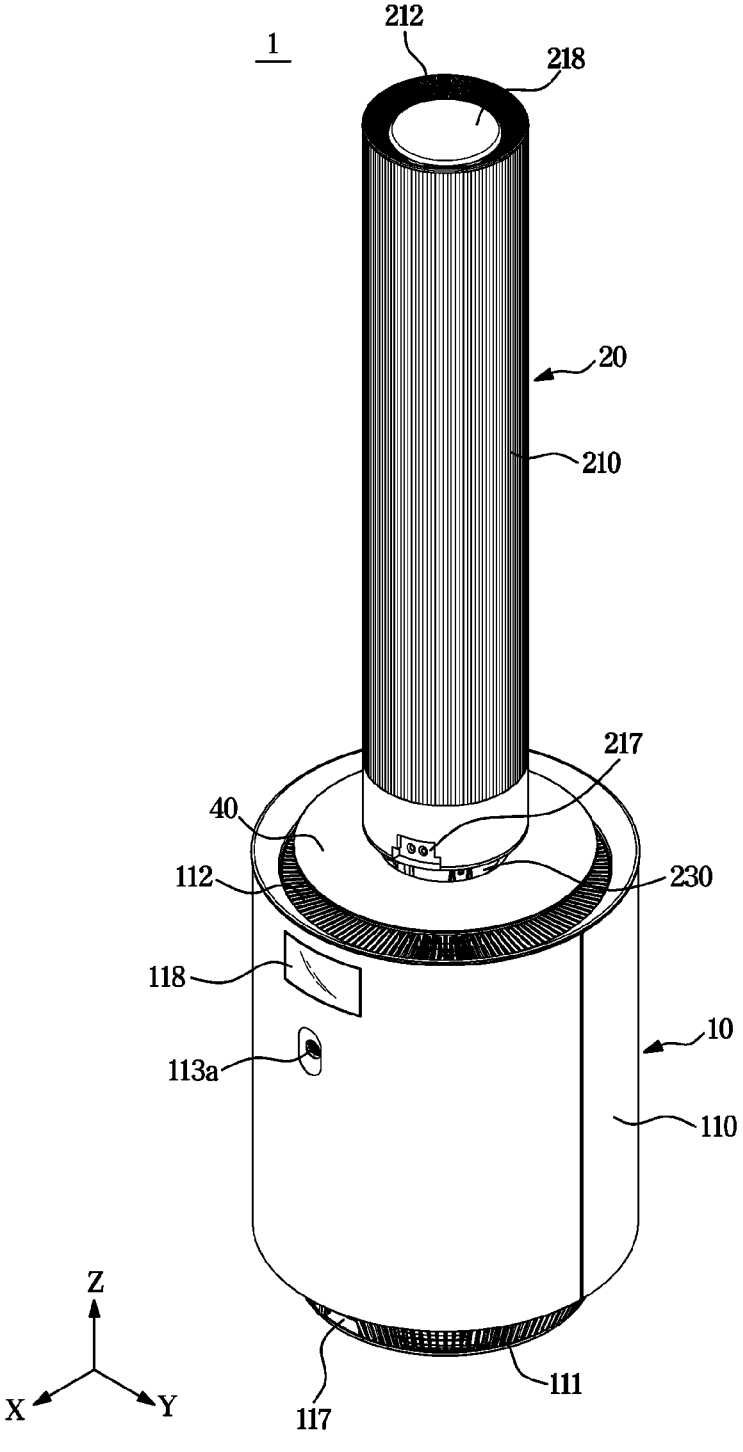
FIG. 1 is a perspective view of an air cleaner according to an embodiment of the present disclosure.
Figure 2:
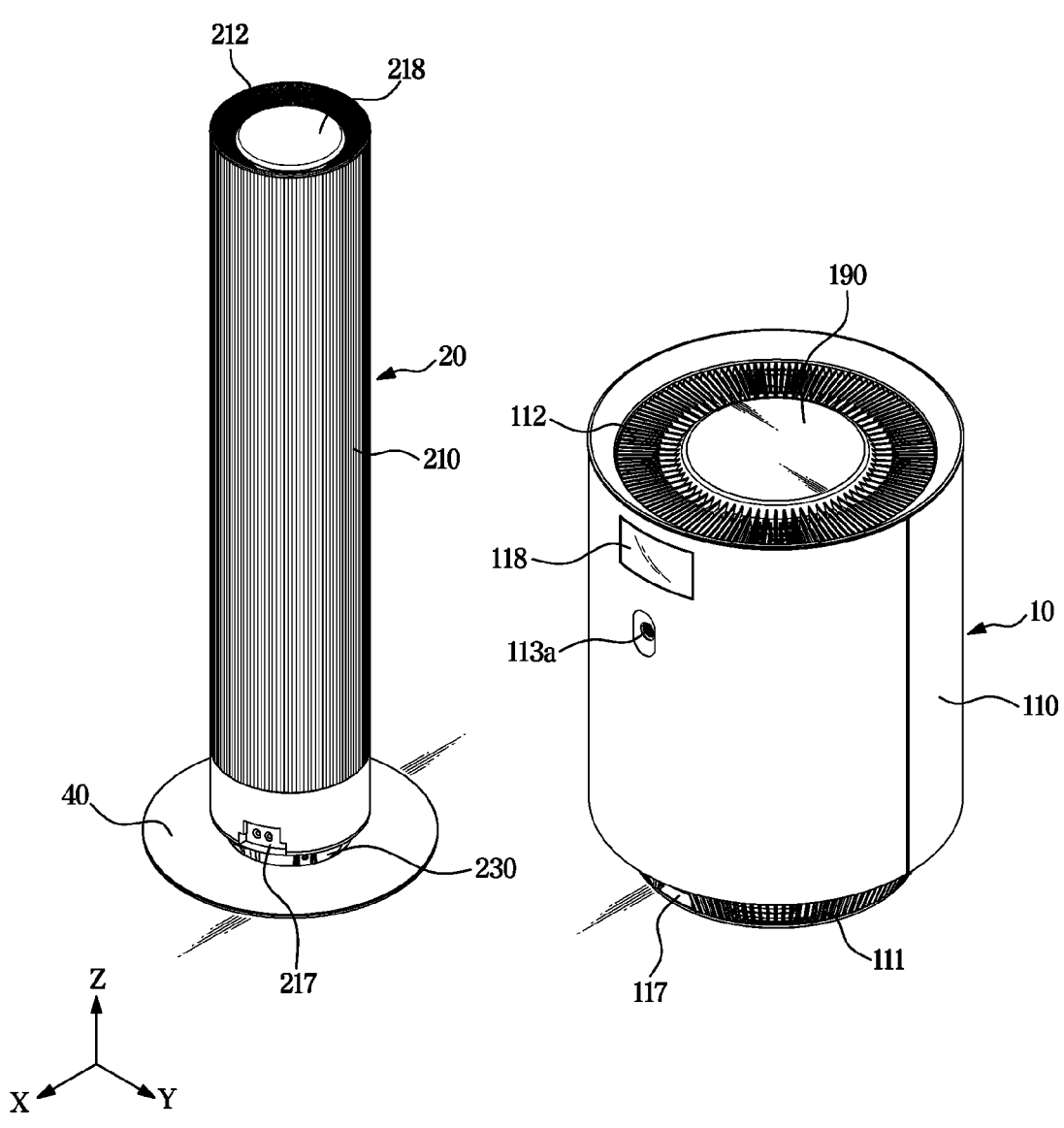
FIG. 2 is a view of a first air cleaning unit and a second air cleaning unit of the air cleaner that are separately supported on the floor according to an embodiment of the present disclosure.
Figure 3:
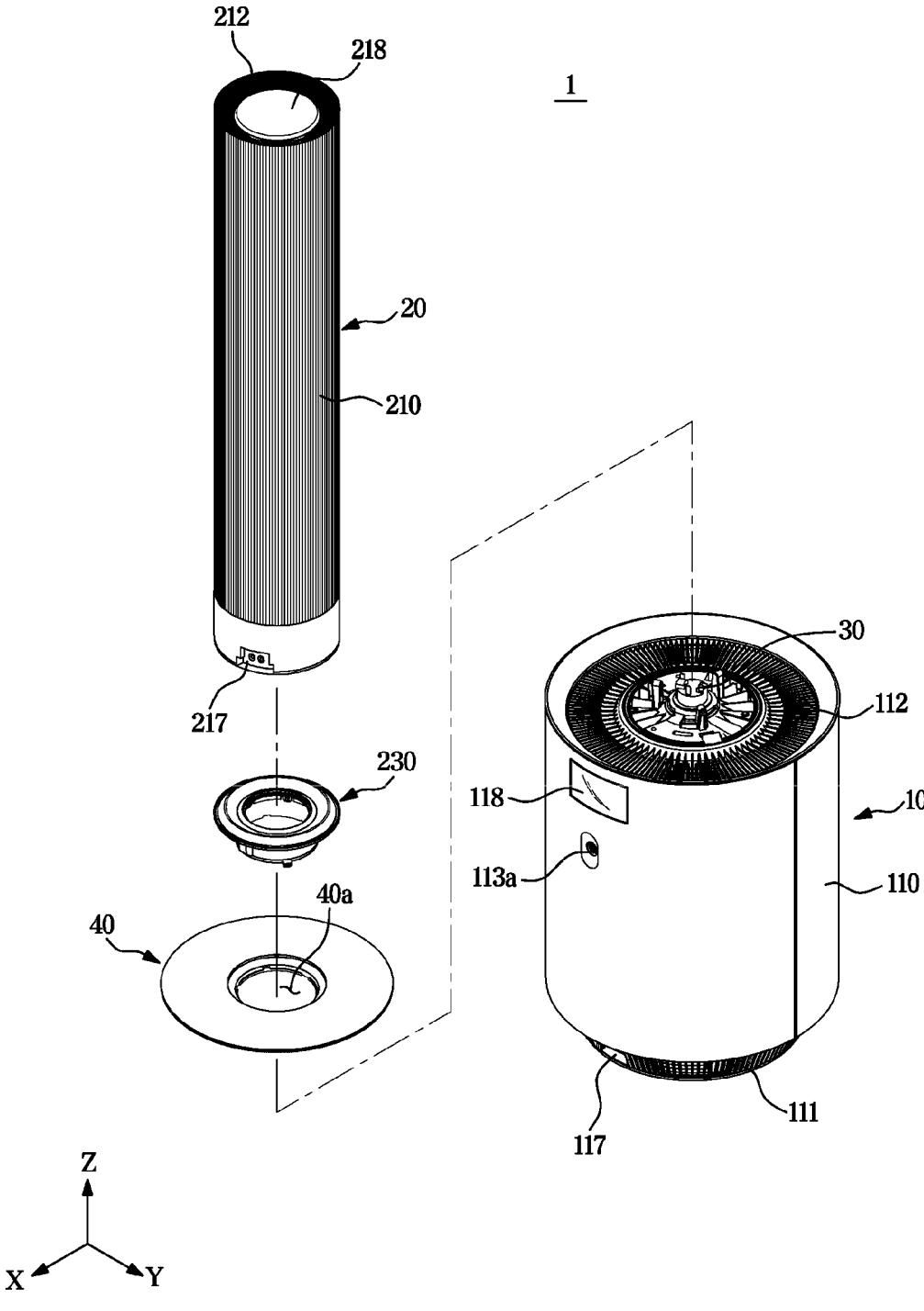
FIG. 3 is an exploded view of a first air cleaning unit and a second air cleaning unit of the air cleaner according to an embodiment of the present disclosure.

FIG. 1 is a perspective view of an air cleaner according to one embodiment of the present disclosure. FIG. 2 is a view of a first air cleaning unit and a second air cleaning unit of the air cleaner that are separately supported on the floor according to one embodiment of the present disclosure. FIG. 3 is an exploded view of a first air cleaning unit and a second air cleaning unit of the air cleaner according to one embodiment of the present disclosure.

Referring to FIGS. 1 to 3, an air cleaner 1 according to one embodiment of the present disclosure may include a first air cleaning unit 10 and a second air cleaning unit 20. The first air cleaning unit 10 may include a first housing 110 formed in a cylindrical shape. The second air cleaning unit 20 may include a second housing 210 formed in a cylindrical shape having a smaller diameter than the first housing 110.

The first air cleaning unit 10 may be configured to purify air introduced from an outside and discharge the purified air back to the outside.

The first air cleaning unit 10 may include a first suction port 111, a first discharge port 112, and a first fan 150. The first air cleaning unit 10 may include a first passage P1 provided between the first suction port 111 and the first discharge port 112. More specifically, the first passage P1 may extend from the first suction port 111 to the first discharge port 112. In a case in which the first fan 150 is driven, air may be introduced through the first suction port 111, flow along the first passage P1, and be discharged through the first discharge port 112 (see FIG. 20).

Air flowing along the first passage P1 in the first air cleaning unit 10 may be purified and discharged to the first discharge port 112. For example, the first air cleaning unit 10 may include a dust collector filter 140 (see FIG. 4). The dust collector filter 140 may be provided in the first passage P1.

The dust collector filter 140 may be provided to collect foreign matter from air introduced through the first suction port 111. Foreign matter such as dust and organic matter including bacteria and viruses in the air flowing along the first passage P1 may be removed from the air by the dust collector filter 140.

A detailed configuration of the first air cleaning unit 10 will be described below.

The second air cleaning unit 20 may be configured to purify air introduced from the outside and discharge the purified air back to the outside.

The second air cleaning unit 20 may include a second suction port (211 in FIG. 6), a second discharge port 212, and a second fan 250. The second air cleaning unit 20 may include a second passage P2 provided between the second suction port 211 and the second discharge port 212. More specifically, the second passage P2 may extend from the second suction port 211 to the second discharge port 212. In a case in which the second fan 250 is driven, air may be introduced through the second suction port 211, flow along the second passage P2, and be discharged through the second discharge port 212 (see FIG. 21).

Air flowing along the second passage P2 in the second air cleaning unit 20 may be purified and discharged to the second discharge port 212. For example, the second air cleaning unit 20 may include a light source (240 in FIG. 6). The light source 240 may be provided in the second passage P2. Organic matter such as bacteria and viruses in the air flowing along the second passage P2 may be removed from the air by the ultraviolet rays emitted from the light source 240.

A detailed configuration of the second air cleaning unit 20 will be described below.

The first air cleaning unit 10 may be disposed to support the second air cleaning unit 20. The first air cleaning unit 10 may be provided to support a lower portion of the second air cleaning unit 20. The second air cleaning unit 20 may be disposed to be seated on an upper side of the first air cleaning unit 10 and may be supported by the first air cleaning unit 10. The case in which the second air cleaning unit 20 is supported by the first air cleaning unit 10 is when the second air cleaning unit 20 is coupled to the first air cleaning unit 10. In this case, the first air cleaning unit 10 and the second air cleaning unit 20 may be disposed in the up-down direction, and the second air cleaning unit 20 may be supported in a direction facing upward by the first air cleaning unit 10. In this respect, the first air cleaning unit 10 may also be referred to as a "lower air cleaning unit," and the second air cleaning unit 20 may also be referred to as an "upper air cleaning unit."

Alternatively, the second air cleaning unit 20 may be separated from the first air cleaning unit 10 and separately provided as shown in FIG. 2. The second air cleaning unit 20 separated from the first air cleaning unit 10 may be supported by the floor. In this way, the second air cleaning unit 20 may be separated from the first air cleaning unit 10, and the air cleaning units 10 and 20 may be separately operated.

The first air cleaning unit 10 and the second air cleaning unit 20 may be separably coupled to each other. The first air cleaning unit 10 and the second air cleaning unit 20 may be provided such that, as the first air cleaning unit 10 and the second air cleaning unit 20 are coupled to each other, the first passage P1 and the second passage P2 may be provided to be connected to each other. In other words, the inside of the first air cleaning unit 10 and the inside of the second air cleaning unit 20 may communicate with each other.

The second air cleaning unit 20 may be coupled to the first air cleaning unit 10 so that the second suction port 211 faces the first discharge port 112 of the first air cleaning unit 10.

For example, as illustrated in FIG. 1, the second air cleaning unit 20 may be coupled to an upper portion of the first air cleaning unit 10. More specifically, the first discharge port 112 may be provided at the upper portion of the first air cleaning unit 10. The second suction port 211 may be provided at the lower portion of the second air cleaning unit 20. The first air cleaning unit 10 and the second air cleaning unit 20 may be coupled to each other in the up-down direction, and the first discharge port 112 provided at the upper portion of the first air cleaning unit 10 and the second suction port 211 provided at the lower portion of the second air cleaning unit 20 may be disposed in the up-down direction.

Unlike in FIG. 1 and so on, for example, the first air cleaning unit 10 and the second air cleaning unit 20 may be coupled to each other in a direction horizontal to the floor. Here, the first discharge port 112 of the first air cleaning unit 10 and the second suction port 211 of the second air cleaning unit 20 may be disposed to face each other in the direction horizontal to the floor.

Hereinafter, for convenience of description, description will be given on the basis of one embodiment in which the second air cleaning unit 20 is coupled to the upper portion of the first air cleaning unit 10 as illustrated in FIG. 1.

The first air cleaning unit 10 may include a first power connector 117 for receiving power from the outside and a first control panel 118. The first power connector 117 may be disposed in a lower portion of the first air cleaning unit 10. The first control panel 118 may be installed on an outer wall of the first housing 110 to be exposed to the outside.

The second air cleaning unit 20 may include a second power connector 217 for receiving power from the outside and a second control panel 218. The second power connector 217 may be disposed in a lower portion of the second air cleaning unit 20. The second control panel 218 may be disposed on an upper side of the second housing 210 to be exposed to the outside.

The reason for separately providing the first power connector 117 and the second power connector 217 is for each of the first air cleaning unit 10 and the second air cleaning unit 20 to receive power from an external power source when the first air cleaning unit 10 and the second air cleaning unit 20 are separated and used separately. The first power connector 117 and the second power connector 217 may have shapes corresponding to each other or may have different shapes.

The first control panel 118 may be a first input device 118, and the second control panel 218 may be a second input device 218. The reason for providing the first control panel 118 and the second control panel 218 in the first air cleaning unit 10 and the second air cleaning unit 20, respectively, is for each of the control panel 118 and the second control panel 218 to separately a user's input when the first air cleaning unit 10 and the second air cleaning unit 20 are separated and used separately.

The first air cleaning unit 10 may include the first housing 110 and a coupling duct 30. The first housing 110 may include a base 114 provided to be supported by a floor. The coupling duct 30 may be located in an upper portion of the first housing 110. The coupling duct 30 may communicate with the first discharge port 112. The coupling duct 30 may be provided such that at least a portion of the air discharged from the first discharge port 112 flows into the second suction port 211.

The second air cleaning unit 20 may include the second housing 210 and a coupling base 40. The coupling base 40 may be disposed on a lower side of the second housing 210, and when the second air cleaning unit 20 is separated from the first air cleaning unit 10, the coupling base 40 may be separately supported by the floor. In addition, the coupling base 40 may be coupled to the coupling duct 30 such that the second air cleaning unit 20 may be supported by the first air cleaning unit 10.

The air cleaner 1 may include a connection passage (CP in FIG. 17) provided inside the coupling duct 30. The connection passage CP may be provided to connect the first passage P1 and the second passage P2. The connection passage CP may be provided between the first passage P1 and the second passage P2. The connection passage CP may be provided to be branched from the first passage P1 and connect the first passage P1 and the second passage P2. An area in which the connection passage CP is branched from the first passage P1 may be positioned adjacent to the first discharge port 112.

The connection passage CP may be provided so that at least one portion of air discharged from the first discharge port 112 is introduced into the second suction port 211 when the first air cleaning unit 10 is coupled to the second air cleaning unit 20. For example, the connection passage CP may be provided between at least one portion of the first discharge port 112 and the second suction port 211. In other words, the connection passage CP may be provided to extend from at least one portion of the first discharge port 112 to the second suction port 211. For example, while the second fan 250 is driven, air in the first passage P1 may flow along the connection passage CP and be introduced into the second passage P2. In other words, the connection passage CP may be provided so that at least one portion of air discharged from the first discharge port 112 is introduced into the connection passage CP and flows to the second passage P2 through the second suction port 211.

Detailed configurations of the coupling duct 30 and the coupling base 40 will be described below.

Figure 4:
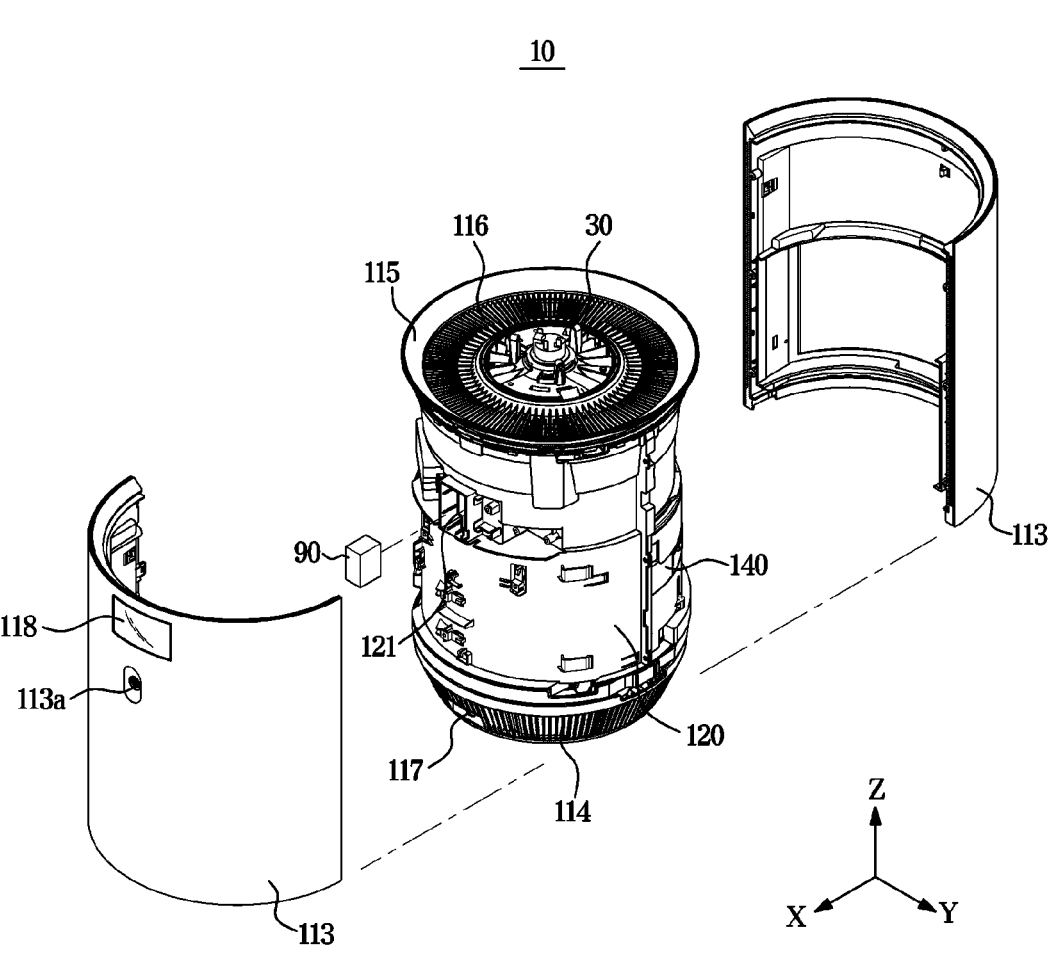
FIG. 4 is an exploded view of a partial configuration of a first air cleaning unit of the air cleaner according to an embodiment of the present disclosure.
Figure 5:
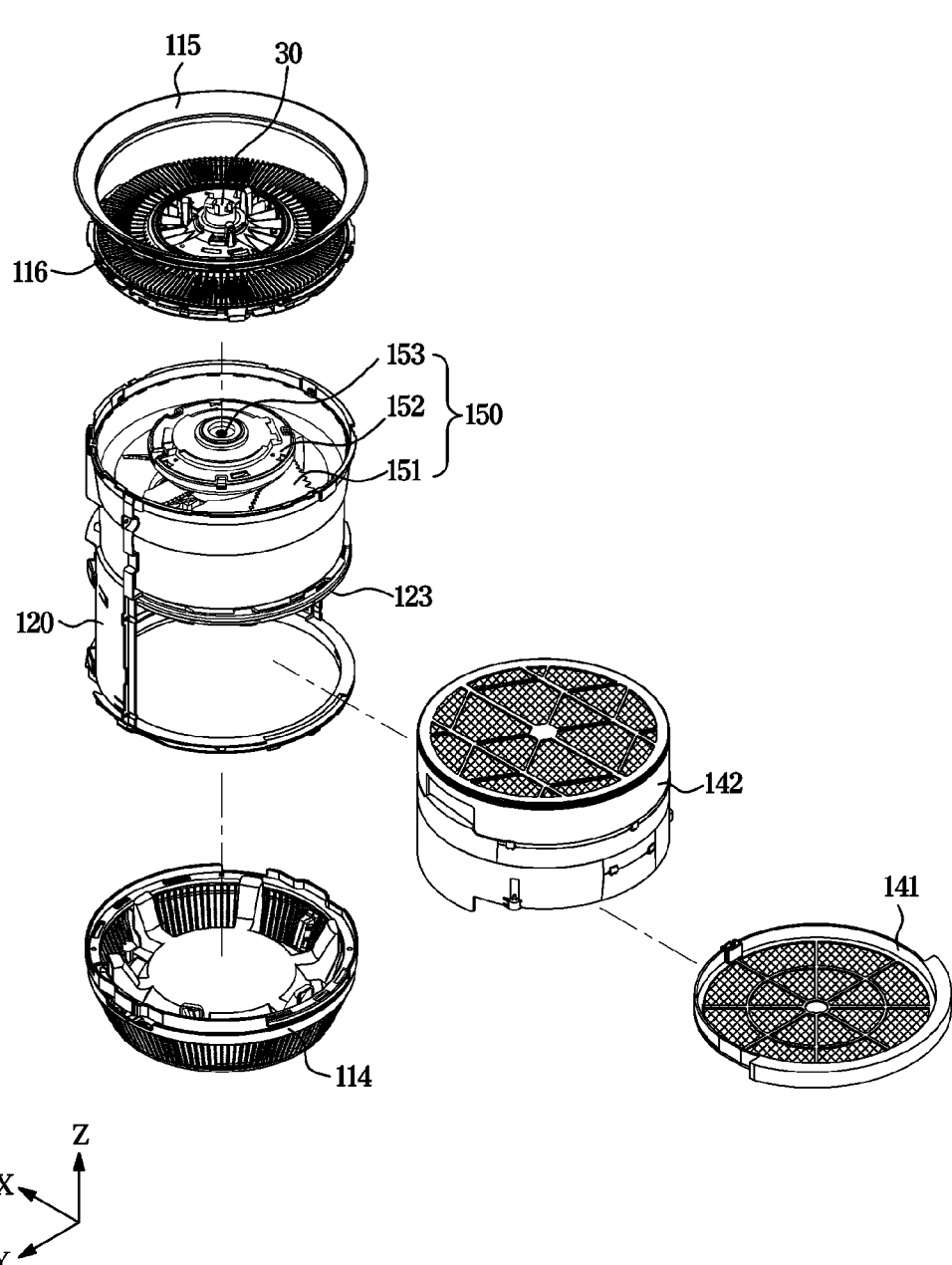
FIG. 5 is an exploded view of a partial configuration of a first air cleaning unit of the air cleaner according to an embodiment of the present disclosure.

FIG. 4 is an exploded view of a partial configuration of the first air cleaning unit of the air cleaner according to one embodiment of the present disclosure. FIG. 5 is an exploded view of a partial configuration of a first air cleaning unit of the air cleaner according to one embodiment of the present disclosure.

Referring to FIGS. 4 and 5, detailed configurations of the first air cleaning unit 10 will be described. The first air cleaning unit 10 may include the first housing 110 configured to have the first passage P1 provided. The first housing 110 may be configured to accommodate various components of the first air cleaning unit 10.

The first housing 110 may include the first suction port 111 and the first discharge port 112. The first suction port 111 may be provided so that air outside the first housing 110 is introduced into the first housing 110. The first discharge port 112 may be provided so that air inside the first housing 110 is discharged to the outside of the first housing 110. While the first fan 150 is driven, due to pressure generated by the first fan 150, air outside the first housing 110 may be drawn into the first housing 110 through the first suction port 111, and air inside the first housing 110 may be discharged to the outside of the first housing 110 through the first discharge port 112.

The first air cleaning unit 10 may include the first passage P1 provided between the first suction port 111 and the first discharge port 112 inside the first housing 110. The first passage P1 may extend from the first suction port 111 to the first discharge port 112. While the first fan 150 is driven, air drawn into the first housing 110 through the first suction port 111 may flow along the first passage P1 and may be discharged to the outside of the first housing 110 through the first discharge port 112. The first suction port 111 may be provided at one end of the first passage P1, and the first discharge port 112 may be provided at the other end of the first passage P1.

For example, the first suction port 111 may be formed at a lower portion of the first housing 110. For example, the first discharge port 112 may be formed at an upper portion of the first housing 110. For example, the first passage P1 may be formed to have a shape elongated in the up-down direction. Accordingly, air introduced into the first housing 110 through the first suction port 111 may flow upward along the first passage P1.

However, the present disclosure is not limited thereto, and the first suction port 111 and the first discharge port 112 may be formed at various other positions of the first housing 110. Corresponding thereto, the first passage P1 provided between the first suction port 111 and the first discharge port 112 may extend in various directions.

The first housing 110 may include a first housing body 113, the base 114, a first upper cover 115, and a first discharge port cover 116. The first housing body 113, the base 114, the first upper cover 115, and the first discharge port cover 116 may each constitute a portion of the exterior of the first air cleaning unit 10.

The first housing body 113 may form a side surface of the first air cleaning unit 10 in the horizontal direction. The first housing body 113 may be provided to cover various components of the first air cleaning unit 10 in the horizontal direction. The first housing body 113 may connect the base 114 and the first upper cover 115.

The first housing body 113 may cover the first passage P1 from outside the first passage P1 in a radial direction. For example, the first passage P1 may be formed between the base 114 and the first discharge port cover 116, and the first housing body 113 may cover the first passage P1 from beside the first passage P1 in the horizontal direction.

The first housing body 113 may extend in a direction parallel to the first passage P1. For example, the first housing body 113 may extend in the up-down direction.

The first housing body 113 may be formed in a substantially hollow cylindrical shape. A space formed inside the first housing body 113 may be formed to have a substantially cylindrical shape. However, the present disclosure is not limited thereto, and the first housing body 113 may be formed to have various other shapes according to the outer shape of the first air cleaning unit 10.

The first housing body 113 may be formed to be divided into a plurality of panels as illustrated in FIG. 4. The plurality of panels constituting the first housing body 113 may be formed to constitute the first housing body 113 in a state in which the plurality of panels are coupled to each other. Accordingly, it may become easy to disassemble or assemble the first housing body 113, and ease of access to an internal configuration of the first housing 110 by a user may be improved. However, the present disclosure is not limited thereto, and the first housing body 113 may be a single configuration formed as one body.

The first housing body 113 may include a sensing hole 113a formed so that a sensor 90 communicates with the outside of the first housing 110. The sensing hole 113a may be formed at a position corresponding to the sensor 90. The sensor 90 may detect outside air introduced through the sensing hole 113a.

The base 114 may be provided at the lower portion of the first housing 110. The base 114 may form a bottom surface of the first air cleaning unit 10. While the first air cleaning unit 10 is placed on the floor, the base 114 may be provided to support the first air cleaning unit 10. Further, in a case in which the second air cleaning unit 20 is coupled to the upper portion of the first air cleaning unit 10, the base 114 may be provided to support the second air cleaning unit 20 as well as the first air cleaning unit 10. That is, the base 114 may be provided to support the air cleaner 1 in the up-down direction. The base 114 may be coupled to a lower portion of the first housing body 113.

The base 114 may include the first power connector 117. The first power connector 117 may be formed on a side surface of the base 114. The first power connector 117 may be configured to allow the first air cleaning unit 10 to be connected to an external power source and receive power from the outside.

As illustrated in FIGS. 4 and 5, the base 114 may be formed in a shape having a bottom surface for coming in contact with the floor in the vertical direction and a side surface which is formed along the circumference of the bottom surface of the base 114 and extends after being bent from the bottom surface. The bottom surface of the base 114 may extend in the horizontal direction. The side surface of the base 114 may be formed in the circumferential direction of the base 114. The side surface of the base 114 may extend from the bottom surface of the base 114 in the vertical direction or a direction having a predetermined angle relative to the vertical direction.

The first suction port 111 may be formed in the base 114. The first suction port 111 may be formed in the side surface of the base 114. The first suction port 111 may be disposed along the circumference of the base 114. The first suction port 111 may be disposed along the circumference of the bottom surface of the base 114. In this case, the side surface of the base 114 may be formed to include the shape of a grille to allow air to enter and exit through the first suction port 111.

However, the present disclosure is not limited thereto, and the first suction port 111 may be formed at various other positions. For example, the first suction port 111 may be formed in the side surface of the base 114 but may be formed only in a portion of the side surface instead of being formed along the circumference of the side surface. For example, the first suction port 111 may be formed to face only one direction in the side surface of the base 114. For example, the first suction port 111 may be formed at various positions of the first housing 110 such as the lower portion of the first housing body 113, other than the base 114.

The first upper cover 115 and the first discharge port cover 116 may be provided at the upper portion of the first housing 110. The first upper cover 115 and the first discharge port cover 116 may form an upper surface of the first air cleaning unit 10. The first upper cover 115 and the first discharge port cover 116 may be formed to cover a space inside the first housing 110 from above the space. The first upper cover 115 may form one portion of an upper surface of the first housing 110, and the first discharge port cover 116 may form another portion of the upper surface of the first housing 110.

The first discharge port 112 may be formed in the upper surface of the first housing 110. The first discharge port cover 116 may be provided to cover the first discharge port 112.

The first discharge port cover 116 may be formed to include the shape of a grille to allow air to enter and exit through the first discharge port 112. For example, the shape of the grille of the first discharge port cover 116 may be disposed along the circumference of the upper surface of the first housing 110. Alternatively, for example, the shape of the grille of the first discharge port cover 116 may be formed only in one portion of the upper surface of the first housing 110. For example, the shape of the grille of the first discharge port cover 116 may be formed only in one portion of the upper surface of the first housing 110.

The first upper cover 115 may be disposed along the circumference of the first discharge port cover 116. The first upper cover 115 may be coupled to an edge of the first discharge port cover 116. The first upper cover 115 may be disposed outside the edge of the first discharge port cover 116.

The first upper cover 115 may have a shape that extends in a direction inclined relative to the horizontal direction. For example, as illustrated in FIGS. 4 and 5, the first upper cover 115 may extend to be inclined upward from the edge of the first discharge port cover 116 toward the outside of the edge. A flow direction of air flowing along the discharge passage (DP in FIG. 17) of air discharged through the first discharge port 112 may be guided by the first upper cover 115.

However, the present disclosure is not limited thereto, and the first upper cover 115 and the first discharge port cover 116 described above are only one example of a configuration forming the upper portion of the first housing 110.

Also, different from the above description, the first discharge port 112 may be formed at various other positions of the first housing 110 such as an upper portion of the first housing body 113.

Unlike in FIGS. 4 and 5, at least some of the first housing body 113, the base 114, the first upper cover 115, and the first discharge port cover 116, which constitute the first housing 110, may be integrally formed with each other. For example, the first upper cover 115 and the first discharge port cover 116 may be integrally formed with each other.

The first housing 110 described above is only one example of a configuration forming the exterior of the first air cleaning unit 10 and having the first passage P1 provided therein, and the spirit of the present disclosure is not limited thereto.

The first air cleaning unit 10 may include a first inner frame 120. The first inner frame 120 may be disposed inside the first housing 110. The first inner frame 120 may be coupled to an inner surface of the first housing 110. The first inner frame 120 may support the inner surface of the first housing 110.

The first inner frame 120 may be provided to support various components of the first air cleaning unit 10. The components of the first air cleaning unit 10, such as the sensor 90, the dust collector filter 140, and the first fan 150, may be supported by the first inner frame 120.

The first inner frame 120 may be covered by the first housing 110. For example, a side of the first inner frame 120 may be covered by the first housing body 113 in the horizontal direction. A bottom of the first inner frame 120 may be covered by the base 114 in the vertical direction. A top of the first inner frame 120 may be covered by the first upper cover 115 and the first discharge port cover 116 in the vertical direction.

The first inner frame 120 may be formed to be divided into a plurality of frames as illustrated in FIGS. 4, 5, and so on. The plurality of frames constituting the first inner frame 120 may be formed to constitute the first inner frame 120 in a state in which the plurality of frames are coupled to each other. Accordingly, it may become easy to disassemble or assemble the first inner frame 120, and ease of access to an internal configuration of the first inner frame 120 by a user may be improved. However, the present disclosure is not limited thereto, and the first inner frame 120 may be a single configuration formed as one body.

A space having a substantially cylindrical shape may be formed inside the first inner frame 120. The dust collector filter 140, the first fan 150, and the like may be disposed in the space inside the first inner frame 120. The first passage P1 may be provided in the space inside the first inner frame 120. The first inner frame 120 may cover an outer side of the first passage P1.

However, the present disclosure is not limited thereto, and the first inner frame 120 may be formed to have various other shapes. For example, the space formed inside the first inner frame 120 may have a shape other than the cylindrical shape. Alternatively, for example, the first inner frame 120 may be provided to support various components of the first air cleaning unit 10 without forming the space therein or covering the outer side of the first passage P1.

The first inner frame 120 described above is only one example of a configuration provided to support various components of the first air cleaning unit 10, and the spirit of the present disclosure is not limited thereto.

The first air cleaning unit 10 may include the coupling duct 30 provided to be coupled to the second air cleaning unit 20. The coupling duct 30 may be provided to be coupled to the coupling base 40 such that the first air cleaning unit 10 and the second air cleaning unit 20 are coupled to each other. For example, the coupling duct 30 and the coupling base 40 may be disposed to face each other.

For example, the coupling duct 30 may be disposed at the upper portion of the first air cleaning unit 10. For example, the coupling duct 30 may be positioned on the upper side of the first housing 110. For example, the coupling duct 30 may extend upward from the first discharge port cover 116 and, further, may be integrally formed with the first discharge port cover 116.

However, the present disclosure is not limited thereto, and the first air cleaning unit 10 may include various other configurations provided to be coupled to the second air cleaning unit 20.

The first air cleaning unit 10 may include the first fan 150. The first fan 150 may be provided in the first passage P1. The first fan 150 may be disposed between the first suction port 111 and the first discharge port 112. The first fan 150 may generate a suction force by rotating, and air outside the first air cleaning unit 10 may be drawn into the first suction port 111 due to the suction force of the first fan 150. The air drawn into the first suction port 111 may flow along the first passage P1 and be discharged to the first discharge port 112.

The first fan 150 may include a first blade 151, a first motor 152 configured to supply power to the first blade 151, and a first fan rotating shaft 153 connected to the first blade 151 and the first motor 152 to transmit power generated by the first motor 152 to the first blade 151.

The first fan 150 may be configured to various types of fans. For example, the first fan 150 may be configured as an axial fan. Alternatively, for example, the first fan 150 may be configured as a centrifugal fan.

The first fan 150 may be disposed between the dust collector filter 140, which will be described below, and the first discharge port 112. While the first fan 150 is driven, air drawn into the first suction port 111 may sequentially pass through the dust collector filter 140 and the first fan 150 and be discharged through the first discharge port 112.

However, the present disclosure is not limited thereto, and for example, the first fan 150 may be disposed between the dust collector filter 140 and the first suction port 111.

The first air cleaning unit 10 may include a first fan support frame (160 in FIG. 20). The first fan 150 may be supported by the first fan support frame 160.

More specifically, the first fan support frame 160 may support the first motor 152. The first motor 152 may be fixed to the first fan support frame 160. The first blade 151 of the first fan 150 is provided to be rotatable about the first fan rotating shaft 153 relative to the first motor 152 and thus may be provided to be rotatable relative to the first fan support frame 160. The first blade 151 may be rotatably supported by the first fan support frame 160.

An opening through which the first passage P1 passes may be formed in the first fan support frame 160. As the first fan 150 is driven, air may pass through the opening of the first fan support frame 160 and flow. For example, in a case in which the first fan 150 is an axial fan, a plurality of openings disposed to oppose each other may be formed in the first fan support frame 160.

The first fan support frame 160 may be supported by the first inner frame 120. The first fan support frame 160 may be coupled to the first inner frame 120. For example, the first fan support frame 160 may be disposed inside the first inner frame 120 and may be coupled to an inner surface of the first inner frame 120.

However, the present disclosure is not limited thereto, and the first fan 150 may be supported by various other configurations.

The first fan 150 described above is only one example of a configuration generating pressure to allow air to flow along the first passage P1 of the first air cleaning unit 10, and the spirit of the present disclosure is not limited thereto.

The first air cleaning unit 10 may include the dust collector filter 140 provided in the first passage P1. While the first fan 150 is driven, air introduced through the first suction port 111 may flow along the first passage P1 and pass through the dust collector filter 140. By the dust collector filter 140, foreign matter may be removed from the air flowing along the first passage P1. Air purified as foreign matter is removed from the air by the dust collector filter 140 may be discharged through the first discharge port 112.

The dust collector filter 140 may be provided to collect foreign matter from air introduced through the first suction port 111. Foreign matter such as dust and organic matter including bacteria and viruses in the air flowing along the first passage P1 may be removed from the air by the dust collector filter 140.

The dust collector filter 140 may be mounted on the first inner frame 120. For example, the dust collector filter 140 may be mounted inside the first inner frame 120. The dust collector filter 140 may be mounted on the inner surface of the first inner frame 120 in order to be disposed in the first passage P1.

The dust collector filter 140 may have an outer peripheral surface formed to come in contact with an inner peripheral surface of the first inner frame 120. The dust collector filter 140 may be provided to substantially fully cover a transverse cross-section of the first passage P1. Even in this case, since the dust collector filter 140 is configured to allow passage of air, air flowing along the first passage P1 may pass through the dust collector filter 140. Further, since the dust collector filter 140 is provided so that, while the first fan 150 is driven, most of the air flowing along the first passage P1 passes through the dust collector filter 140, efficiency of purifying the air of the first passage P1 may be improved.

The dust collector filter 140 may be separably mounted on the first inner frame 120. For example, the first inner frame 120 may include a dust collector filter mounting opening 123 formed so that the dust collector filter 140 is able to be inserted into or withdrawn from the inside of the first inner frame 120. The inside of the first inner frame 120 may be open through the dust collector filter mounting opening 123.

For example, the dust collector filter mounting opening 123 may be formed at one side of the first inner frame 120. The dust collector filter 140 may be inserted and mounted at the one side of the first inner frame 120 or may be withdrawn and detached at the one side of the first inner frame 120.

By such a configuration, a user may easily detach or assemble the dust collector filter 140 from or to the first inner frame 120, and repair, replacement, cleaning, or the like of the dust collector filter 140 may be facilitated.

However, the present disclosure is not limited thereto, and the dust collector filter 140 may be mounted on the first inner frame 120 in various other ways. Alternatively, the dust collector filter 140 may be supported by various other configurations in order to be disposed in the first passage P1.

The dust collector filter 140 may include a first pre-filter 141. The first pre-filter 141 may be provided in the first passage P1. The first pre-filter 141 may be provided to primarily collect foreign matter from air drawn into the first suction port 111. The first pre-filter 141 may be provided to separate relatively large foreign matter from the air.

The dust collector filter 140 may include an electric dust collector filter 142. The electric dust collector filter 142 may be provided in the first passage P1.

The electric dust collector filter 142 may be configured to collect dust using an electrostatic force. The electric dust collector filter 142 may receive power from the first power connector 117 which will be described below. While power is applied to the electric dust collector filter 142, an electric field may be formed in the electric dust collector filter 142. Due to the electric field formed in the electric dust collector filter 142, foreign matter such as dust may be collected from air. Also, due to the electric field formed in the electric dust collector filter 142, organic matter such as bacteria and viruses may be decomposed. That is, the electric dust collector filter 142 may perform a dust collection function and a sterilization function.

Specifically, the electric dust collector filter 142 may include a filter case 142a, a dust collector 142b, and a charger 142c configured to form an exterior of the electric dust collector filter 142.

The filter case 142a may support the dust collector 142b and the charger 142c. The filter case 142a may be supported by the first inner frame 120. At least one electrode configured to receive power from the first power connector 117 may be provided in the filter case 142a. For example, an electrode of the first inner frame 120 that is electrically connected to the first power connector 117 may be provided in the first inner frame 120, and while the dust collector filter 140 is mounted on the first inner frame 120, the electrode of the first inner frame 120 and the electrode of the filter case 142a may be connected to each other. The electrode of the first inner frame 120 or the electrode of the filter case 142a may be configured to include a conductive metal material. More specifically, at least one of the electrode of the first inner frame 120 and the electrode of the filter case 142a may be configured to include a leaf spring shape (not illustrated).

The charger 142c may be provided to charge foreign matter in air. The dust collector 142b may be provided to collect foreign matter charged by the charger 142c.

The dust collector 142b and the charger 142c may each be provided to receive power from the first power connector 117. The dust collector 142b and the charger 142c may each be electrically connected to the electrode of the filter case 142a.

Electrodes of different polarities may be connected to the charger 142c and the dust collector 142b. An electric field may be formed between the charger 142c and the dust collector 142b. Foreign matter in air that is charged by the charger 142c may be charged to a polarity identical to the polarity of the charger 142c and may be charged to a polarity opposite to the polarity of the dust collector 142b. Accordingly, due to an electric force, the foreign matter in the air that is charged by the charger 142c may move to the dust collector 142b and be collected by the dust collector 142b. Also, due to the electric force, organic matter such as bacteria and viruses floating in the air may be decomposed.

The charger 142c may be provided at one side of the electric dust collector filter 142, and the dust collector 142b may be provided at the other side of the electric dust collector filter 142. The charger 142c and the dust collector 142b may be disposed to oppose each other. For example, the charger 142c and the dust collector 142b may be disposed to face each other in the up-down direction.

More specifically, the charger 142c may be provided upstream of the dust collector 142b in the first passage P1. The charger 142c may be disposed between the dust collector 142b and the first suction port 111. The dust collector 142b may be disposed between the charger 142c and the first discharge port 112. For example, the dust collector 142b may be provided at an upper portion of the electric dust collector filter 142, and the charger 142c may be provided at a lower portion of the electric dust collector filter 142.

By such a configuration, the electric dust collector filter 142 may remove foreign matter from air flowing along the first passage P1.

The pre-filter 141 may be disposed between the first suction port 111 and the electric dust collector filter 142. The electric dust collector filter 142 may be disposed between the first discharge port 112 and the pre-filter 141.

The pre-filter 141 may be separably mounted on the electric dust collector filter 142. More specifically, the pre-filter 141 may be separably mounted on the filter case 142a of the electric dust collector filter 142. The pre-filter 141 may be supported by the filter case 142a. Specifically, the pre-filter 141 may be supported by a lower portion of the filter case 142a.

The dust collector filter 140 described above is only one example of a configuration provided to remove foreign matter such as dust and organic matter from air flowing along the first passage P1 of the first air cleaning unit 10, and the spirit of the present disclosure is not limited thereto.

For example, the pre-filter 141 included in the dust collector filter 140 may not be mounted on the electric dust collector filter 142 and, further, may be disposed to be spaced apart from the electric dust collector filter 142. That is, the pre-filter 141 and the electric dust collector filter 142 may each be separately mounted on the first inner frame 120.

For example, the pre-filter 141 may not be included in the dust collector filter 140.

For example, the electric dust collector filter 142 may not be included in the dust collector filter 140. Instead, various other filters such as a high efficiency particulate air (HEPA) filter may be included in the dust collector filter 140. Antibacterial treatment, such as application of an antibacterial substance, may be performed on a filter included in the dust collector filter 140, and accordingly, organic matter such as bacteria and viruses in air introduced through the first suction port 111 may be removed from the air by the dust collector filter 140.

The air cleaner 1 may include a control device (50 in FIG. 16) configured to control the operation of the air cleaner 1. The control device 50 may include a first printed circuit board assembly (PBA) (52 in FIG. 20). The first PBA 52 may be configured to control the operation of the air cleaner 1. The first PBA 52 may be formed by electronic components for controlling the operation of the air cleaner 1 being mounted on a printed circuit board (PCB). For example, the first PBA 52 may be a main board.

The first PBA 52 may be disposed in the first air cleaning unit 10. For example, the first PBA 52 may be supported by the base 114 of the first air cleaning unit 10.

The first PBA 52 may be electrically connected to various components disposed in the first air cleaning unit 10, such as the first power connector 117, the sensor 90, and the first fan 150. Further, the first PBA 52 may be electrically connected to a second PBA (53 in FIG. 7), which will be described below, provided in the second air cleaning unit 20. In the case in which the first PBA 52 is a main board, the first PBA 52 may be connected to the second PBA 53 via a wire and may transmit a command for controlling the operation of the second air cleaning unit 20 to the second PBA 53.

The present disclosure is not limited thereto, and the first PBA 52 may be disposed at various other positions. Also, the first PBA 52 may be configured in various other ways to control the operation of the air cleaner 1.

The air cleaner 1 may include the first power connector 117 configured to supply power to various components of the air cleaner 1. The first power connector 117 may be electrically connected to the first PBA 52. The first power connector 117 may be configured to apply power to various components such as the electric dust collector filter 142.

The first power connector 117 may be disposed in the first air cleaning unit 10. For example, the first power connector 117 may be mounted on the first inner frame 120.

The first power connector 117 may receive power from an external power source. The first power connector 117 may be configured to immediately transmit power received from the external power source to components for driving the air cleaner 1 or configured to store power received from the external power source and then transmit the power to components for driving the air cleaner 1.

The present disclosure is not limited thereto, and the first power connector 117 may be disposed at various other positions. Also, the first power connector 117 may be configured in various other ways to supply power for driving the air cleaner 1.

The air cleaner 1 may include the sensor 90. The sensor 90 may be configured to sense a condition of air in an indoor space or the like where the air cleaner 1 is installed. For example, the sensor 90 may detect outside air through the sensing hole 113a.

Various types of sensors may be configured as the sensor 90. Examples of the sensor 90 may include a dust measuring sensor configured to measure concentration of dust in air, a carbon dioxide measuring sensor configured to measure concentration of carbon dioxide in air, a harmful gas measuring sensor configured to measure concentration of other harmful gases (e.g., total volatile organic compounds (TVOC)) in air, and an organic matter measuring sensor configured to measure concentration of organic matter in air.

For example, the sensor 90 may be disposed in the first air cleaning unit 10. More specifically, the sensor 90 may be mounted on the first inner frame 120. The first inner frame 120 may include a sensor mounting portion 121, and the sensor 90 may be mounted on the sensor mounting portion 121 by various methods such as fastening.

The present disclosure is not limited thereto, and the sensor 90 may be disposed at various other positions. Also, the sensor 90 may be configured in various other ways to sense an air condition that is to be detected to control the operation of the air cleaner 1. The sensor of the air cleaner 1 may be provided in the first passage P1.

The configuration of the first air cleaning unit 10 described above with reference to FIGS. 4 and 5 is only one example for describing the first air cleaning unit of the air cleaner according to the spirit of the present disclosure, and the spirit of the present disclosure is not limited thereto. The first air cleaning unit of the air cleaner according to the spirit of the present disclosure may be provided to include various configurations for performing a function of purifying air flowing along the first passage.

Figure 6:
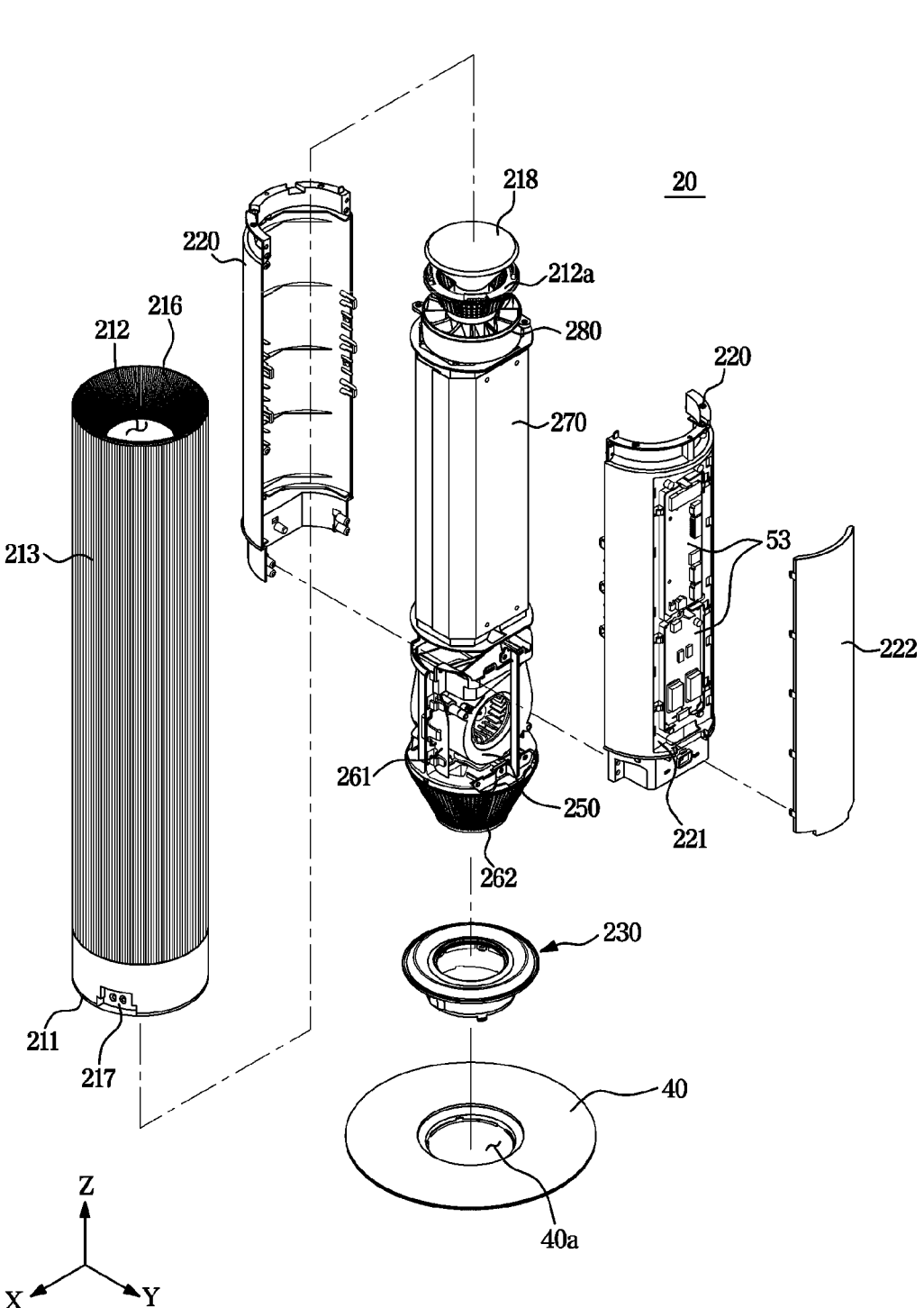
FIG. 6 is an exploded view of a partial configuration of a second air cleaning unit of the air cleaner according to an embodiment of the present disclosure.
Figure 7:
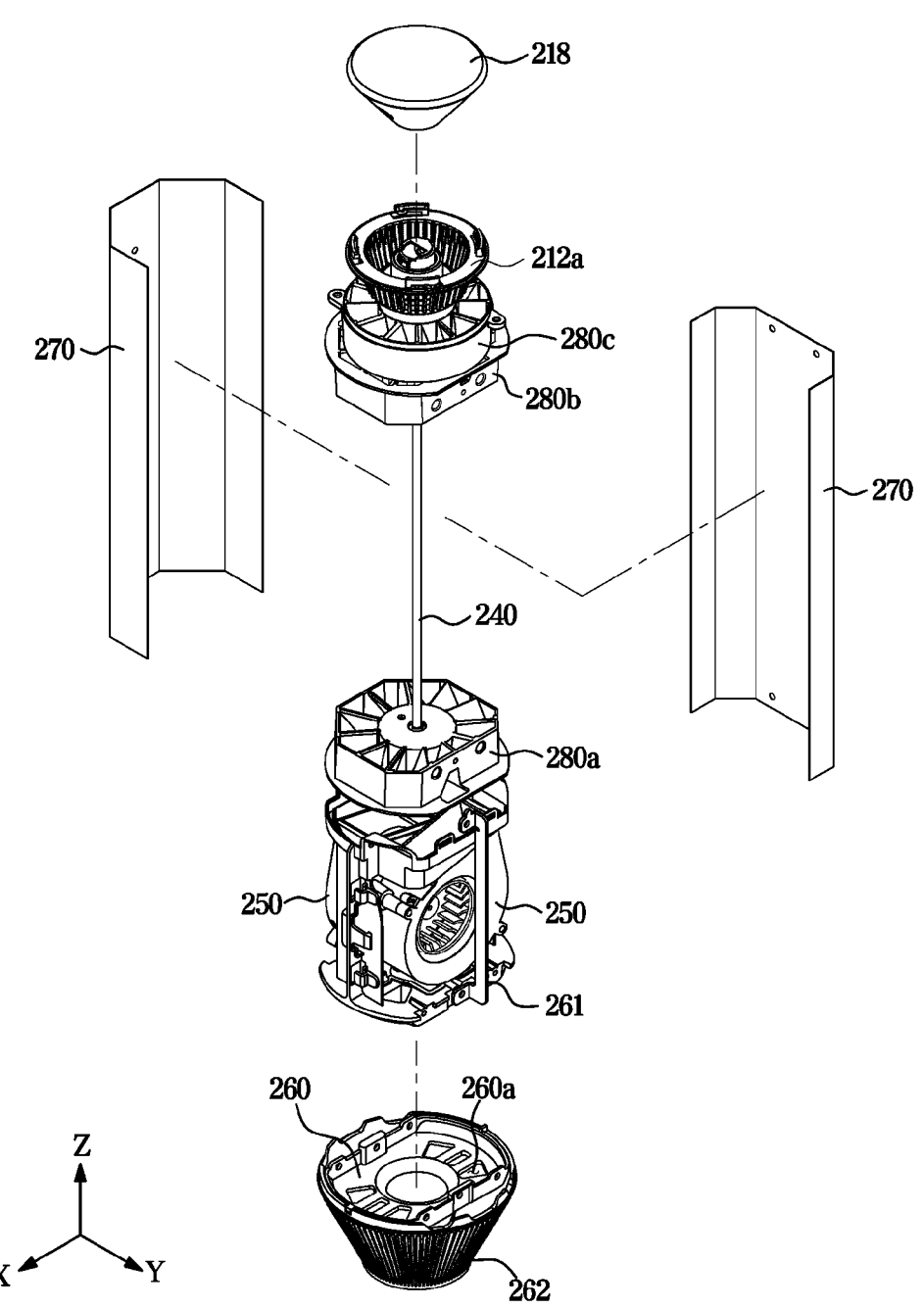
FIG. 7 is an exploded view of a partial configuration of a second air cleaning unit of the air cleaner according to an embodiment of the present disclosure.
Figure 8:
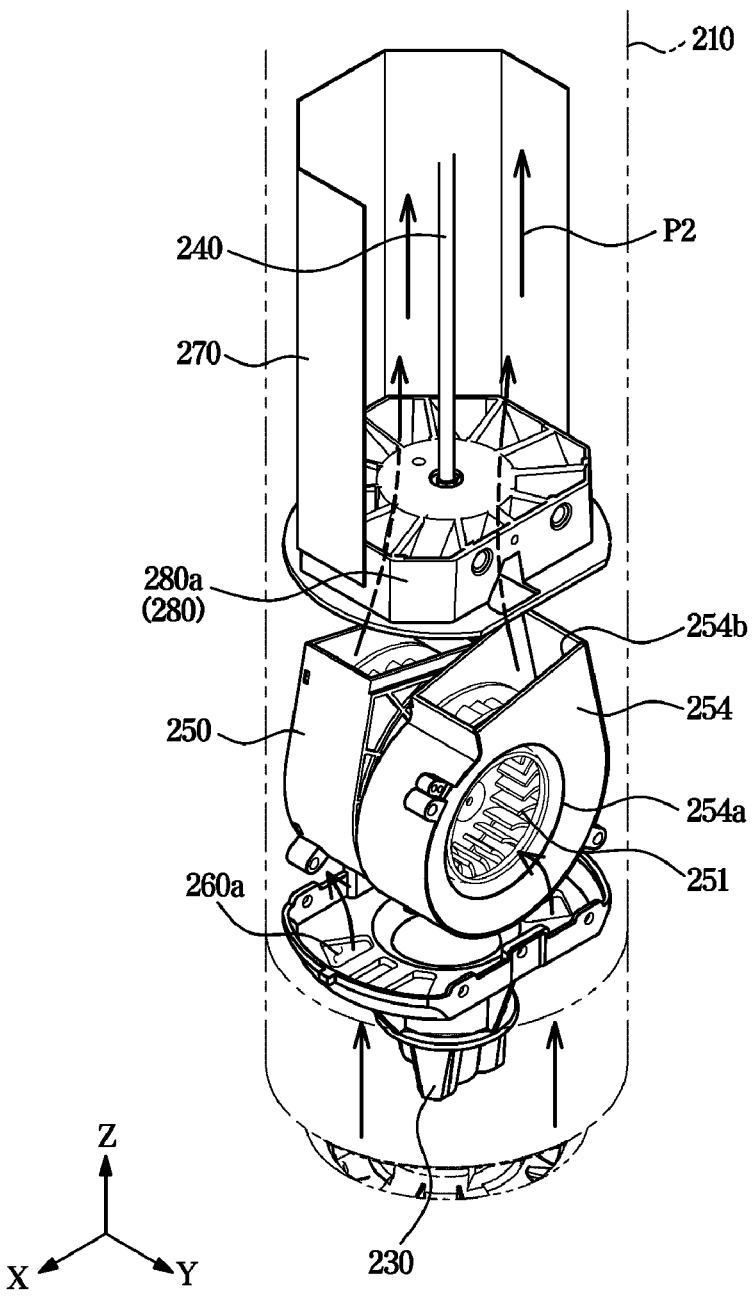
FIG. 8 is a view for describing a state in which air flows in a second air cleaning unit of the air cleaner according to an embodiment of the present disclosure.
Figure 9:
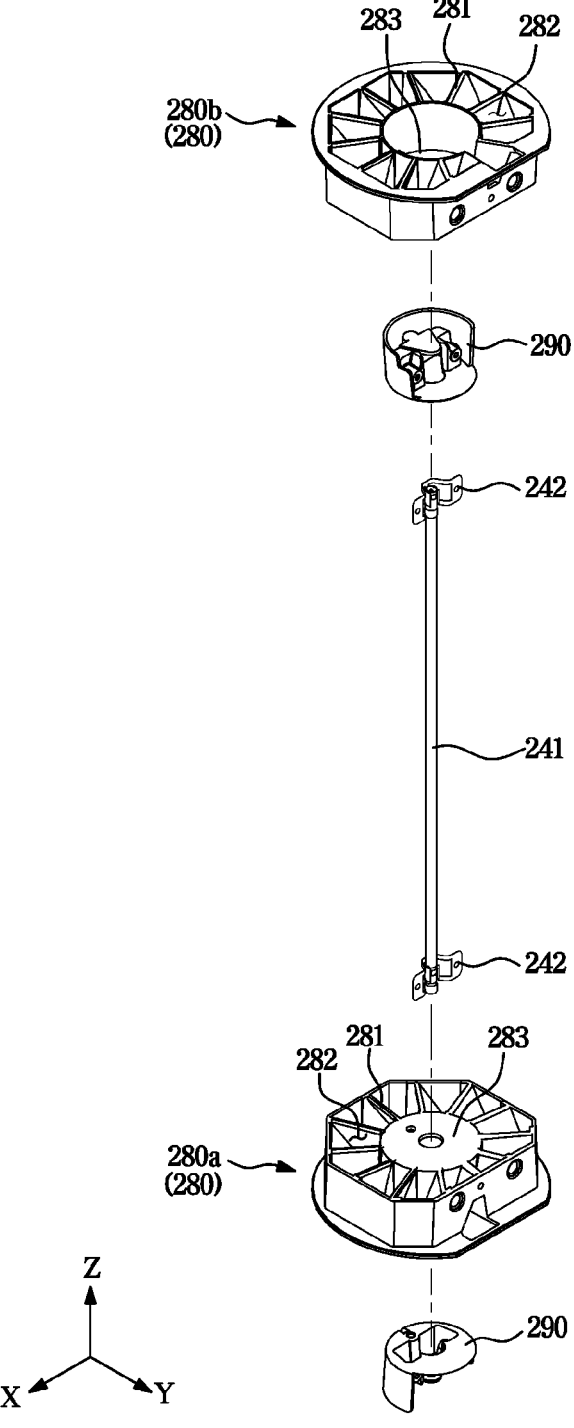
FIG. 9 is a view of a partial configuration of a light source and a second air cleaning unit of the air cleaner according to an embodiment of the present disclosure.
Figure 10:
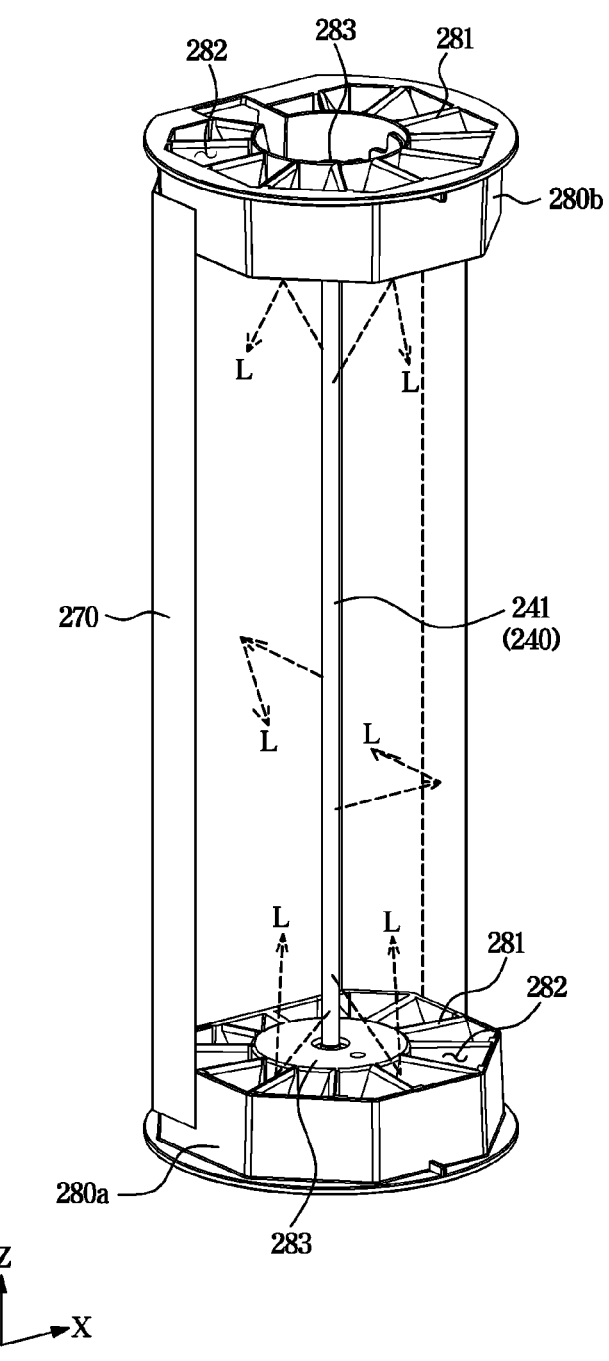
FIG. 10 is a view illustrating a path of light emitted from a light source in the air cleaner according to an embodiment of the present disclosure.
Figure 11:
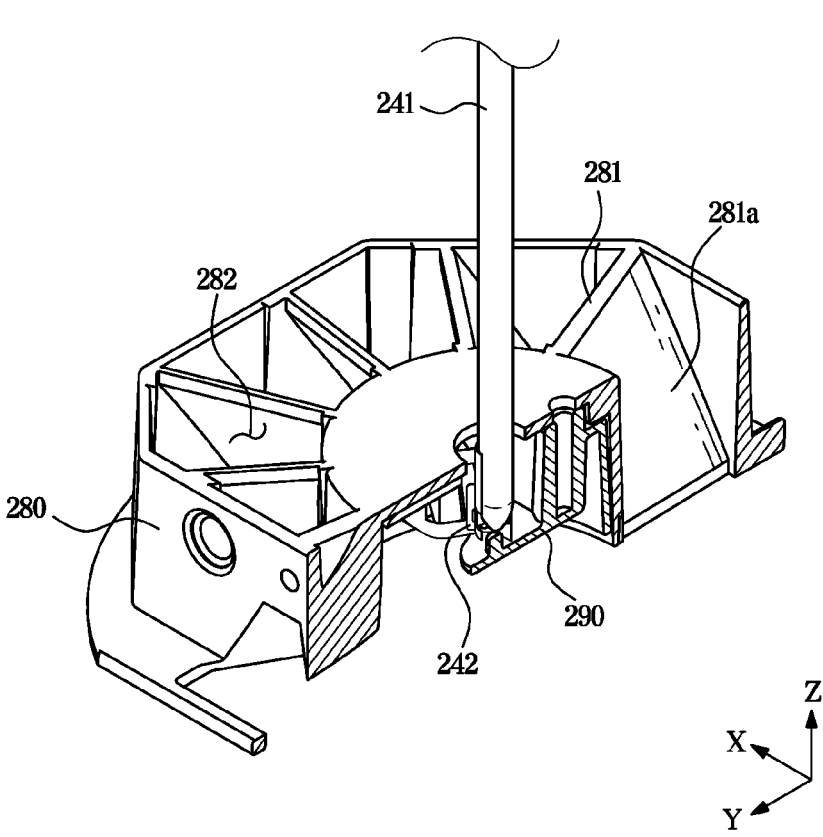
FIG. 11 is a cross-sectional view illustrating a cut-out of a light source and a partial configuration of the air cleaner according to an embodiment of the present disclosure.

FIG. 6 is an exploded view of a partial configuration of the second air cleaning unit of the air cleaner according to one embodiment of the present disclosure. FIG. 7 is an exploded view of a partial configuration of the second air cleaning unit of the air cleaner according to one embodiment of the present disclosure. FIG. 8 is a view for describing a state in which air flows in the second air cleaning unit of the air cleaner according to one embodiment of the present disclosure. FIG. 9 is a view of a partial configuration of a light source and a second air cleaning unit of the air cleaner according to one embodiment of the present disclosure. FIG. 10 is a view illustrating a path of light emitted from a light source in the air cleaner according to one embodiment of the present disclosure. FIG. 11 is a cross-sectional view illustrating a cut-out of a light source of the air cleaner and a partial configuration of the air cleaner according to one embodiment of the present disclosure.

Referring to FIGS. 6 to 11, the second air cleaning unit 20 may include the second housing 210 configured to have the second passage P2 provided therein. The second housing 210 may form an exterior of the second air cleaning unit 20. The second housing 210 may be configured to accommodate various components of the second air cleaning unit 20.

The second housing 210 may include the second suction port 211 and the second discharge port 212. The second suction port 211 may be provided so that air outside the second housing 210 is introduced into the second housing 210. More specifically, the second suction port 211 may be provided so that air inside the first housing 110 or air introduced into the connection passage (CP in FIG. 17) of air outside the first housing 110 and the second housing 210 is introduced into the second housing 210. The second discharge port 212 may be provided so that air inside the second housing 210 is discharged to the outside of the second housing 210.

While the second fan 250 is driven, due to pressure generated by the second fan 250, air outside the second housing 210 may be drawn into the second housing 210 through the second suction port 211, and air inside the second housing 210 may be discharged to the outside of the second housing 210 through the second discharge port 212.

In addition, in the case in which the coupling base 40 of the second air cleaning unit 20 is coupled to and the coupling duct 30 of the first air cleaning unit 10, the first fan (150 in FIG. 5) and the second fan 250 may be simultaneously driven. While the first fan 150 and the second fan 250 are simultaneously driven, at least one portion of air inside the first housing 110 may sequentially pass through the connection passage (CP in FIG. 17) and the second suction port 211 and flow to the second passage P2, and air flowing along the second passage P2 may be discharged through the second discharge port 212.

While the first fan 150 is not driven and the second fan 250 is driven with the second air cleaning unit 20 and the first air cleaning unit 10 being coupled to each other, air outside the first housing 110 and the second housing 210, that is, air outside the air cleaner 1, may, after being introduced into the first housing 110, more specifically, an upper side of the first housing 110, through the first discharge port 112, sequentially pass through the connection passage CP and the second suction port 211 and flow to the second passage P2. The air flowing along the second passage P2 may be discharged through the second discharge port 212.

However, the present disclosure is not limited thereto, and for example, in the case in which the first fan 150 is not driven and only the second fan 250 is driven, the second suction port 211 may be formed to directly intake air outside the air cleaner 1 through a guide hole (41 in FIG. 21) of the coupling base 40.

The second air cleaning unit 20 may include the second passage P2 provided between the second suction port 211 and the second discharge port 212 inside the second housing 210. In other words, the second passage P2 may extend from the second suction port 211 to the second discharge port 212. While the second fan 250 is driven, air drawn into the second housing 210 through the second suction port 211 may flow along the second passage P2 and may be discharged to the outside of the second housing 210 through the second discharge port 212. The second suction port 211 may be provided at one end of the second passage P2, and the second discharge port 212 may be provided at the other end of the second passage P2.

For example, the second suction port 211 may be formed at a lower portion of the second housing 210. For example, the second discharge port 212 may be formed at an upper portion of the second housing 210. For example, the second passage P2 may be formed to have a shape elongated in the up-down direction. Accordingly, air introduced into the second housing 210 through the second suction port 211 may flow upward along the second passage P2.

However, the present disclosure is not limited thereto, and the second suction port 211 and the second discharge port 212 may be formed at various other positions of the second housing 210. Corresponding thereto, the second passage P2 provided between the second suction port 211 and the second discharge port 212 may extend in various directions.

The second housing 210 may include a second housing body 213 and a second upper cover 216. The second housing body 213 and the second upper cover 216 may each constitute a portion of the exterior of the second air cleaning unit 20.

The second housing body 213 may form a side surface of the second air cleaning unit 20 in the horizontal direction. The second housing body 213 may be provided to cover various components of the second air cleaning unit 20 in the horizontal direction. The second housing body 213 may be connected to the second upper cover 216. The second housing body 213 may be connected to the coupling base 40.

The second housing body 213 may cover the second passage P2 from outside the second passage P2 in a radial direction. In other words, the second housing body 213 may cover the second passage P2 from beside the second passage P2 in the horizontal direction.

The second housing body 213 may extend in a direction parallel to the second passage P2. For example, the second housing body 213 may extend in the up-down direction.

The second housing body 213 may be formed in a substantially hollow cylindrical shape. A space formed inside the second housing body 213 may be formed to have a substantially cylindrical shape. However, the present disclosure is not limited thereto, and the second housing body 213 may be formed to have various other shapes according to the outer shape of the second air cleaning unit 20.

The second suction port 211 and the second discharge port 212 may be formed in the second housing body 213. The second suction port 211 may be provided at one end of the second housing body 213 in a direction toward the coupling duct 30. The second discharge port 212 may be provided at the other end of the second housing body 213 that is opposite the second suction port 211.

For example, the second suction port 211 may be formed at a lower end of the second housing body 213. The second discharge port 212 may be formed at an upper end of the second housing body 213.

However, the present disclosure is not limited thereto, and the second suction port 211 and the second discharge port 212 may be formed at various other positions.

The second upper cover 216 may be provided at an upper portion of the second housing 210. The second upper cover 216 may form an upper surface of the second air cleaning unit 20. The second upper cover 216 may be formed to cover the space inside the first housing 110 from above the space. The second upper cover 216 may form at least one portion of the upper surface of the first housing 110.

The second upper cover 216 may be provided at the second discharge port 212. In other words, the second upper cover 216 may partially cover the second discharge port 212. The second upper cover 216 may be provided to guide a flow of air discharged through the second discharge port 212.

The second upper cover 216 may be formed along the circumference of the second discharge port 212. Alternatively, the second upper cover 216 may be formed along the circumference of the second housing body 213.

The second upper cover 216 may have a shape whose width increases in a direction toward an outer edge thereof. For example, the second upper cover 216 may have a shape whose width increases upward. Accordingly, the second upper cover 216 may guide air discharged through the second discharge port 212 to be diffused outward. The second upper cover 216 may be formed to have a substantially diffuser-like shape.

However, the present disclosure is not limited thereto, and the second upper cover 216 may be configured in various other ways to form the upper surface of the second air cleaning unit 20.

For example, the second housing body 213 and the second upper cover 216 may be formed as configurations separated from each other. On the other hand, for example, the second housing body 213 and the second upper cover 216 may also be integrally formed with each other.

The second air cleaning unit 20 may include a second discharge port grille 212a provided in the second discharge port 212. The second discharge port grille 212a may be formed to include the shape of a grille to allow air to enter and exit through the second discharge port 212. For example, the second discharge port 212 may be positioned at an upper side of the second passage P2, and corresponding thereto, the second discharge port grille 212a may be positioned at the upper side of the second passage P2.

The second discharge port grille 212a may be coupled to the second upper cover 216. The second discharge port grille 212a may support the second upper cover 216.

For example, the second discharge port grille 212a may be coupled to an inner edge of the second upper cover 216. The second discharge port grille 212a may be formed along the inner edge of the second upper cover 216.

However, the present disclosure is not limited thereto, and the second discharge port grille 212a may be configured in various other ways to allow air to be discharged through the second discharge port 212. Unlike the above description, the second discharge port 212 may be formed at various other positions of the second housing 210, such as a side surface of the second housing body 213. Corresponding thereto, the second discharge port grille 212a may be provided at various other positions and formed to have various other shapes.

The second housing 210 described above is only one example of a configuration forming the exterior of the second air cleaning unit 20 and having the second passage P2 provided therein, and the spirit of the present disclosure is not limited thereto.

The second air cleaning unit 20 may include a second inner frame 220. The second inner frame 220 may be disposed inside the second housing 210. The second inner frame 220 may be coupled to an inner surface of the second housing 210. The second inner frame 220 may support the inner surface of the second housing 210.

The second inner frame 220 may be provided to support at least some of the components of the second air cleaning unit 20. For example, the light source 240, a reflective cover 270, a light blocking member 280, and the like may be supported by the second inner frame 220. Also, the second PBA 53, the second control panel 218, and the like may also be supported by the second inner frame 220.

The second inner frame 220 may be covered by the second housing 210. For example, a side of the second inner frame 220 may be covered by the second housing body 213 in the horizontal direction. A top of the second inner frame 220 may be covered by the second upper cover 216 in the vertical direction.

The second inner frame 220 may be formed to be divided into a plurality of frames as illustrated in FIG. 6 and so on. The plurality of frames constituting the second inner frame 220 may be formed to constitute the second inner frame 220 in a state in which the plurality of frames are coupled to each other. Accordingly, it may become easy to disassemble or assemble the second inner frame 220, and ease of access to an internal configuration of the second inner frame 220 by a user may be improved. However, the present disclosure is not limited thereto, and the second inner frame 220 may be a single configuration formed as one body.

A space having a substantially cylindrical shape may be formed inside the second inner frame 220. The light source 240, the reflective cover 270, and the like may be disposed in the space inside the second inner frame 220. At least one portion of the second passage P2 may be provided in the space inside the second inner frame 220. More specifically, a radiation area R1, which will be described below, may be provided in the space inside the second inner frame 220.

However, the present disclosure is not limited thereto, and the second inner frame 220 may be formed to have various other shapes. For example, the space formed inside the second inner frame 220 may have a shape other than the cylindrical shape. Alternatively, for example, the second inner frame 220 may be provided to support various components of the second air cleaning unit 20 without forming the space therein or covering the outer side of the second passage P2.

The second inner frame 220 described above is only one example of a configuration provided to support various components of the second air cleaning unit 20, and the spirit of the present disclosure is not limited thereto.

The second air cleaning unit 20 may include the coupling base 40 provided to be coupled to the first air cleaning unit 10. The coupling base 40 may be provided to be coupled to the coupling duct 30 such that the first air cleaning unit 10 and the second air cleaning unit 20 are coupled to each other.

For example, the coupling base 40 may be disposed at the lower portion of the second air cleaning unit 20. For example, the coupling base 40 may be disposed on a lower side of the second housing 210 facing the coupling duct 30.

A second fan guide portion 260 may include at least one hole 260a formed to allow passage of air flowing along the second passage P2.

The second fan guide portion 260 may be supported by a second fan support frame 261. The second fan guide portion 260 may be coupled to a second fan guard 262.

However, the present disclosure is not limited thereto, and the second air cleaning unit 20 may include various other configurations provided to be coupled to the first air cleaning unit 10.

The second air cleaning unit 20 may include the second fan 250. The second fan 250 may be provided in the second passage P2. The second fan 250 may be disposed between the second suction port 211 and the second discharge port 212. The second fan 250 may generate a suction force by rotating, and air outside the second air cleaning unit 20 may be drawn into the second suction port 211 due to the suction force of the second fan 250. The air drawn into the second suction port 211 may flow along the second passage P2 and be discharged to the second discharge port 212.

The second fan 250 may be disposed between the light source 240, which will be described below, and the second suction port 211. While the second fan 250 is driven, air drawn into the second suction port 211 may sequentially pass through the second fan 250 and the light source 240 and be discharged through the second discharge port 212.

However, the present disclosure is not limited thereto, and for example, the second fan 250 may be disposed between the light source 240 and second discharge port 212. Hereinafter, description will be given assuming that the second fan 250 is disposed between the light source 240 and the second suction port 211 as illustrated in FIGS. 6 to 8.

The second fan 250 may include a second blade 251, a second motor 252 configured to supply power to the second blade 251, and a second fan rotating shaft 253 connected to the second blade 251 and the second motor 252 to transmit power generated by the second motor 252 to the second blade 251.

The second fan 250 may include a second fan case 254 configured to support the second blade 251, the second motor 252, the second fan rotating shaft 253, and the like. The second blade 251, the second motor 252, and the second fan rotating shaft 253 may be accommodated in the second fan case 254.

More specifically, the second fan case 254 may support the second motor 252 of the second fan 250. The second motor 252 may be fixed to the second fan case 254. The second blade 251 of the second fan 250 is provided to be rotatable about the second fan rotating shaft 253 relative to the second motor 252 and thus may be provided to be rotatable relative to the second fan case 254. In other words, the second blade 251 may be rotatably supported by the second fan case 254.

The second fan case 254 may include a fan inlet 254a formed so that air is introduced into the second fan case 254 and a fan discharge duct 254b formed so that air is discharged to the outside of the second fan case 254. The second passage P2 may be provided to pass through the fan inlet 254a and the fan discharge duct 254b. As the second fan 250 is driven, air in the second passage P2 may pass through the fan inlet 254a and the fan discharge duct 254b and flow.

As illustrated in FIGS. 6 to 8, in the second fan 250, a direction in which air is introduced through the fan inlet 254a and a direction in which air is discharged through the fan discharge duct 254b may be different from each other. More specifically, the direction in which air is introduced through the fan inlet 254a may be parallel to the second fan rotating shaft 253. The direction in which air is discharged through the fan discharge duct 254b may be orthogonal to the second fan rotating shaft 253.

In other words, the fan discharge duct 254b may extend in a direction orthogonal to the second fan rotating shaft 253. The fan discharge duct 254b may be provided so that air is discharged in the direction orthogonal to the second fan rotating shaft 253 toward the light source 240.

That is, the second fan 250 may be configured as a centrifugal fan.

The second fan 250 may be provided as a plurality of second fans 250. The plurality of second fans 250 may be formed to have shapes that correspond to each other.

Each of the plurality of second fans 250 may be provided to discharge air in the direction orthogonal to the second fan rotating shaft 253 toward the light source 240. Directions in which air is discharged from the plurality of second fans 250 may be provided to be inclined to have a predetermined angle relative to the direction in which the second passage P2 extends, that is, the up-down direction. Here, a direction of inclination relative to the up-down direction of a direction in which air is discharged from one of the plurality of second fans 250 and a direction of inclination relative to the up-down direction of a direction in which air is discharged from the other one of the plurality of second fans 250 may be provided to be opposite to each other. More specifically, in each of the plurality of second fans 250, the fan discharge duct 254b may be positioned to be deviated by a predetermined distance from a central axis of the second passage P2, and here, the fan discharge duct 254b may have an inclined shape in which an outer end through which air is discharged extends toward the central axis of the second passage P2.

However, the shape, arrangement, number, and the like of the second fans 250 are not limited thereto, and the second fans 250 may be provided in various other ways. For example, the second fans 250 may be configured as various types of fans such as an axial fan. For example, the second fan 250 may be provided as a single second fan 250.

The second fan 250 described above is only one example of a configuration generating pressure to allow air to flow along the second passage P2 of the second air cleaning unit 20, and the spirit of the present disclosure is not limited thereto.

The second air cleaning unit 20 may include the second fan support frame 261. The second fan 250 may be supported by the second fan support frame 261.

The second fan support frame 261 may be coupled to the second inner frame 220. For example, the second fan support frame 261 may be coupled to a lower portion of the second inner frame 220.

The second fan support frame 261 may be coupled to the second fan guide portion 260. For example, the second fan support frame 261 may be coupled to an upper portion of the second fan guide portion 260.

However, the present disclosure is not limited thereto, and the second fan 250 may be supported by various other configurations.

The second air cleaning unit 20 may include the second fan guard 262 disposed upstream of the second fan 250 in the second passage P2. The second fan guard 262 may cover one side of the second fan 250 that is adjacent to the second suction port 211. The second fan guard 262 may be provided between the second fan 250 and the second suction port 211.

The second fan guard 262 may include a fan guard hole (262a in FIG. 21). The fan guard hole 262a may be formed to allow passage of air flowing along the second passage P2. Air introduced into the second housing 210 through the second suction port 211 may pass through the fan guard hole 262a and flow toward the second fan 250.

The second air cleaning unit 20 may include the light source 240 provided in the second passage P2. The light source 240 may be configured to radiate ultraviolet rays to the second passage P2. The ultraviolet rays radiated from the light source 240 may have a wavelength range in which sterilization is possible. Organic matter such as bacteria and viruses present in air flowing along the second passage P2 may be destroyed and removed by the ultraviolet rays radiated from the light source 240. That is, the light source 240 may perform a function of sterilizing the air flowing along the second passage P2.

Detailed description of the configuration and operation of the light source 240 will be given below.

The second air cleaning unit 20 may include the reflective cover 270 provided to reflect ultraviolet rays radiated from the light source 240. The reflective cover 270 may cover an outer side of the light source 240. The reflective cover 270 may be provided in the second passage P2.

An inner surface of the reflective cover 270 that faces the light source 240 may be configured to include a material with high light reflectivity. For example, the inner surface of the reflective cover 270 may be plated with a metal material with high light reflectivity. Alternatively, for example, the reflective cover 270 may be configured as a single plate made of a metal material with high light reflectivity.

The reflective cover 270 may have a shape formed to be bent to surround the light source 240. For example, the reflective cover 270 may include a plurality of flat plate shapes, and the plurality of plate shapes may be provided to surround the light source 240 while forming a predetermined angle with each other.

As illustrated in FIG. 7, the reflective cover 270 may be provided as a plurality of reflective covers 270. The plurality of reflective covers 270 may each cover the outer side of the light source 240. Specifically, one of the plurality of reflective covers 270 may cover one side of the light source 240, and the other one of the plurality of reflective covers 270 may cover the other side of the light source 240.

However, the present disclosure is not limited thereto, and the reflective cover 270 may also be provided as a single reflective cover 270.

However, the present disclosure is not limited thereto, and the reflective cover 270 may be provided in various other ways to, from outside the light source 240, reflect ultraviolet rays radiated from the light source 240.

The second passage P2 may include the radiation area R1 in which ultraviolet rays are radiated from the light source 240. While the second fan 250 is driven, air introduced into the second housing 210 through the second suction port 211 may be sterilized while passing through the radiation area R1, and organic matter such as bacteria and viruses may be removed from the air.

The radiation area R1 may be provided at an inner side of the reflective cover 270. The radiation area R1 may be surrounded by the reflective cover 270, and thus an outer side of the radiation area R1 may be covered. For example, the reflective cover 270 may cover the radiation area R1 from beside the radiation area R1 in the horizontal direction.

By the above configuration, ultraviolet rays radiated from the light source 240 may be reflected by the reflective cover 270 and not be incident on an area outside the radiation area R1, and sterilization efficiency of the light source 240 may be improved.

The second air cleaning unit 20 may further include the light blocking member 280 provided to prevent ultraviolet rays radiated from the light source 240 from being incident on the outside of the radiation area R1.

The light blocking member 280 may be provided in the second passage P2. The light blocking member 280 may be formed to allow passage of air flowing along the second passage P2. That is, the light blocking member 280 may be provided to, while preventing ultraviolet rays radiated from the light source 240 from being emitted to the outside of the radiation area R1, allow air outside the radiation area R1 to flow to the inside of the radiation area R1 through the light blocking member 280 or allow air inside the radiation area R1 to flow to the outside of the radiation area R1 through the light blocking member 280.

For example, the light blocking member 280 may include a first light blocking member 280a, a second light blocking member 280b, and a third light blocking member 280c. For example, the first light blocking member 280a may be provided at one side of the radiation area R1 that faces the second suction port 211. The second light blocking member 280b and the third light blocking member 280c may be provided at the other side of the radiation area R1 that faces the second discharge port 212. Since the plurality of light blocking member 280b and 280c are provided at the other side of the radiation area R1 that faces the second discharge port 212 as illustrated in FIGS. 6 to 9, it is possible to more efficiently prevent ultraviolet rays from being emitted to the outside of the air cleaner 1 through the second discharge port 212 or the like and being introduced into a living space of a user.

The first light blocking member 280a and the second light blocking member 280b may be provided to support the light source 240. More specifically, the first light blocking member 280a and the second light blocking member 280b may be provided to support both ends of the light source 240.

The radiation area R1 may be provided between the first light blocking member 280a and the second light blocking member 280b. The first light blocking member 280a and the second light blocking member 280b may be provided at both ends of the radiation area R1. For example, the first light blocking member 280a and the second light blocking member 280b may be provided at both ends of the radiation area R1 in the up-down direction.

By the above configuration, ultraviolet rays radiated from the light source 240 may be blocked by the light blocking member 280 and not be incident on an area outside the radiation area R1, and components of the air cleaner 1 provided in the area outside the radiation area R1 may be prevented from being damaged due to the ultraviolet rays. Also, it is possible to prevent ultraviolet rays from being emitted to the outside of the air cleaner 1 through the second discharge port 212 or the like and being introduced into a living space of a user.

Detailed description of the configuration and function of the light blocking member 280 will be given below.

The air cleaner 1 may include the second control panel 218. The second control panel 218 may include an input button (218a in FIG. 16) and a display 218b. The second control panel 218 may be disposed in the second air cleaning unit 20. For example, the second control panel 218 may be supported by the second inner frame 220. For example, the second control panel 218 may be supported by the third light blocking member 280c.

More specifically, the second control panel 218 may be disposed at an upper portion of the second air cleaning unit 20. For example, the second air cleaning unit 20 may be provided to partially cover the second discharge port 212. For example, an outer edge of the second discharge port 212 may be covered by the second upper cover 216.

Detailed description of the configuration and operation of the second control panel 218 will be given below.

The control device 50 of the air cleaner 1 may include the second PBA 53.

The second PBA 53 may be configured to control the operation of the air cleaner 1. The second PBA 53 may be formed by electronic components for controlling the operation of the air cleaner 1 being mounted on a PCB.

The second PBA 53 may be disposed in the second air cleaning unit 20. For example, the second PBA 53 may be supported by the second inner frame 220 of the second air cleaning unit 20.

More specifically, the second inner frame 220 may include a board mounting portion 221 provided so that the second PBA 53 is mounted. In the case in which the second inner frame 220 is made up of a plurality of frames, the board mounting portion 221 may be provided on at least one of the plurality of frames constituting the second inner frame 220.

The second inner frame 220 may include a board mounting cover 222 configured to cover the second PBA 53. The board mounting cover 222 may be separably coupled to the board mounting portion 221. The board mounting cover 222 may be provided to protect the second PBA 53.

The second PBA 53 may be electrically connected to various components disposed on the second PBA 53, such as the second control panel 218, the light source 240, and the second fan 250. Further, the second PBA 53 may be electrically connected to the first PBA 52 described above. The second PBA 53 may be connected via a wire to the first PBA 52 and may receive a command for controlling the operation of the second air cleaning unit 20 from the first PBA 52.

The second PBA 53 may be configured to include a plurality of boards as illustrated in FIG. 6. In this case, the plurality of boards included in the second PBA 53 may be electrically connected to each other. However, the present disclosure is not limited thereto, and the second PBA 53 may also be configured to include a single board.

Features of the second PBA 53 are not limited thereto, and the second PBA 53 may be disposed at various other positions. Also, the second PBA 53 may be configured in various other ways to control the operation of the air cleaner 1.

The configuration of the second air cleaning unit 20 described above with reference to FIGS. 6 to 11 is only one example for describing the second air cleaning unit of the air cleaner according to the spirit of the present disclosure, and the spirit of the present disclosure is not limited thereto. The second air cleaning unit of the air cleaner according to the spirit of the present disclosure may be provided to include various other configurations for performing a function of purifying air flowing along the second passage.

Referring to FIGS. 9 and 11, the air cleaner 1 may include the light source 240 provided in the second passage P2. The air cleaner 1 may include each of the dust collector filter 140 provided in the first passage P1 in the first housing 110 and the light source 240 provided in the second passage P2 in the second housing 210 and thus improve air purification efficiency. The light source 240 may be one configuration included in the second air cleaning unit 20.

The light source 240 may be provided to radiate ultraviolet rays to the radiation area R1. Specifically, the light source 240 may be provided to radiate ultraviolet rays in a wavelength region suitable for removing organic matter such as bacteria and viruses. For example, the light source 240 may be provided to radiate ultraviolet rays included in the UV-C wavelength region (for example, a wavelength region having a range of about 250 to 260 nm). In this respect, the light source 240 may be referred to as a sterilization device, a sterilization lamp, or the like.

The light source 240 applied to a sterilization device may be configured using various methods such as a method in which an electrode inside a glass tube is used as in a hot cathode florescent lamp (HCFL) and a cold cathode florescent lamp (CCFL) and a method in which an electrode outside a glass tube is used as in an external electrode fluorescent lamp (EEFL).

Hereinafter, a specific configuration and operation of the light source 240 will be described in detail while assuming that the light source 240 is configured using the EEFL method.

The light source 240 may include a lamp body 241 from which light L is projected and an electrode portion 242 configured to receive power.

The lamp body 241 may have a substantially cylindrical shape. The lamp body 241 may extend in one direction. For example, the lamp body 241 may extend in the up-down direction.

The lamp body 241 may be configured to include a material through which ultraviolet rays can pass. For example, the lamp body 241 may be configured to include a material such as quartz or borosilicate.

The lamp body 241 may include a hollow discharge space S therein. A gas (not illustrated) for emitting ultraviolet rays through discharge may be accommodated in the lamp body 241. A rare gas or the like may be used as the gas for emitting ultraviolet rays through discharge. When voltage is applied to a gas, such as a rare gas, in a floor state, an excited dimer (hereinafter referred to as an "excimer") may be formed. The excimer is in an unstable state and thus immediately returns to the floor state, and in this process, ultraviolet rays may be generated. A rare gas with which the lamp body 241 is filled may be made of xenon (Xe), a Xe-mixed gas (including Xe, Ar, Ne, etc.), and the like.

An inner wall of the lamp body 241 may be coated with a fluorescent body (not illustrated) configured to convert a light emission wavelength region of Xe (for example, about 172 nm) into a sterilization wavelength region (for example, about 250 to 260 nm). However, the gas accommodated in the lamp body 241 is not limited to a rare gas such as Xe and a gas mixed with the rare gas, and various other types of gases configured to emit ultraviolet rays through discharge may be accommodated in the lamp body 241. The inner wall of the lamp body 241 may be coated with various other types of fluorescent bodies according to the wavelength of the emitted ultraviolet rays.

The light source 240 may include an external electrode (not illustrated) disposed at an outer surface of the lamp body 241. The external electrode may extend in a direction in which the lamp body 241 extends. In other words, the external electrode may be disposed on the outer surface of the lamp body 241 and extend in the longitudinal direction of the lamp body 241.

The external electrode may include a pair of external electrodes. The pair of external electrodes may be disposed to oppose each other on an outer peripheral surface of the lamp body 241, with respect to a central axis of the lamp body 241.

The external electrode may be provided in the shape of a thin tape on the outer surface of the lamp body 241. The external electrode may be configured to include a conductive material. For example, the external electrode may be configured to include a conductive metal material such as gold, silver, nickel, carbon, gold palladium, silver palladium, platinum, aluminum, or an alloy thereof.

The electrode portion 242 may be configured to receive power from a device provided outside the light source 240. For example, the electrode portion 242 may be electrically connected to the second PBA 53 and receive power from the second PBA 53.

The electrode portion 242 may be configured to include a conductive material in order to receive power form the outside. For example, the electrode portion 242 may be configured to include a conductive metal material.

The electrode portion 242 may be provided to receive power from the outside and transmit power to the external electrode provided on the outer surface of the lamp body 241. The electrode portion 242 may be electrically connected to the external electrode.

The electrode portion 242 may be provided as a pair of electrode portions 242, and each of the pair of electrode portions 242 may be fixed to one of both ends of the lamp body 241. The pair of electrode portions 242 may be configured to receive voltages of different polarities.

Each of the pair of electrode portions 242 may be electrically connected to one of the pair of external electrodes. Any one of the pair of external electrodes may be electrically connected to any one of the pair of electrode portions 242. The other one of the pair of external electrodes may be electrically connected to the other one of the pair of electrode portions 242. Accordingly, the pair of external electrodes may receive voltages of different polarities.

The light source 240 described above is only one example of the light source included in the air cleaner according to the spirit of the present disclosure, and the spirit of the present disclosure is not limited thereto.

The second air cleaning unit 20 may include a light source fixing member 290 provided to fix the light source 240. The light source fixing member 290 may fix the electrode portion 242 of the light source 240. The light source fixing member 290 may be provided as a pair of light source fixing members 290 to correspond to the number of electrode portions 242 of the light source 240. The pair of light source fixing members 290 may be arranged in parallel to a direction in which the light source 240 extends. For example, the pair of light source fixing members 290 may be arranged in the up-down direction.

For example, each of the pair of electrode portions 242 may be inserted into one of the pair of light source fixing members 290. Each of the pair of electrode portions 242 may be configured to be connected to one of the pair of light source fixing members 290 and receive power.

The light source fixing member 290 may be supported by the light blocking member 280. For example, any one of the pair of light source fixing members 290 may be supported by the first light blocking member 280a, and the other one of the pair of light source fixing members 290 may be supported by the second light blocking member 280b.

In this way, by supporting the light source fixing member 290, the light blocking member 280 may support the electrode portion 242 and support the light source 240. However, the present disclosure is not limited thereto, and the light blocking member 280 may also be formed to directly support the electrode portion 242.

By such a configuration, the light source 240 may receive power from the outside and be configured to radiate ultraviolet rays.

Hereinafter, the configuration and operation of the light source 240 in the radiation area R1 will be described in detail with reference to FIGS. 10 and 11.

The light source 240 may extend in one direction. The direction in which the light source 240 extends may correspond to a direction of extension of the radiation area R1 in which ultraviolet rays L are radiated from the light source 240. Further, the direction in which the light source 240 extends may correspond to the direction in which the second passage P2 extends. In other words, the radiation area R1 may extend in one direction to correspond to the light source 240. For example, the direction in which the light source 240 or the radiation area R1 extends may be the up-down direction of the air cleaner 1.

The reflective cover 270 may be provided to reflect at least one portion of the ultraviolet rays L radiated from the light source 240. The reflective cover 270 may extend in the direction of extension of the light source 240 in order to correspond to the light source 240. The reflective cover 270 may extend in the direction of extension of the radiation area R1 in order to correspond to the radiation area R1. For example, the direction in which the reflective cover 270 extends may be the up-down direction of the air cleaner 1.

The reflective cover 270 may cover the outer side of the light source 240. The reflective cover 270 may be disposed in the circumferential direction of the light source 240. The reflective cover 270 may cover the light source 240 from beside the light source 240 in the horizontal direction.

The reflective cover 270 may cover the outer side of the radiation area R1. The reflective cover 270 may be disposed in the circumferential direction of the radiation area R1. The reflective cover 270 may cover the radiation area R1 from beside the radiation area R1 in the horizontal direction.

The reflective cover 270 may cover at least one portion of a side surface of the light blocking member 280 from outside the light blocking member 280. The reflective cover 270 may be disposed in the circumferential direction of the light blocking member 280. The reflective cover 270 may cover the at least one portion of the side surface of the light blocking member 280 from beside the light blocking member 280 in the horizontal direction. The reflective cover 270 may be formed to have a shape that corresponds to the shape of the side surface or edge of the light blocking member 280.

The light blocking member 280 may be provided in the second passage P2. The light blocking member 280 may be provided at one side of the radiation area R1 in one direction (that is, the direction of extension of the light source 240, the radiation area R1, and the like). Specifically, each of the plurality of light blocking members 280a and 280b may be provided at one of both sides of the radiation area R1 in the one direction.

The radiation area R1 is one configuration of the second passage P2 and should be provided to allow an air flow, and accordingly, the light blocking member 280 should be provided to allow passage of air flowing along the second passage P2. This is particularly because the light blocking member 280 may be disposed at one side of the radiation area R1 in the one direction.

However, since the ultraviolet rays L radiated from the light source 240 may have high energy, there is a possibility of damage to other components of the second air cleaning unit 20 when the ultraviolet rays L are emitted to the outside of the radiation area R1. Also, when the ultraviolet rays L are emitted through the second discharge port 212, there is a possibility that the ultraviolet rays L may enter a living space of a user.

The light blocking member 280 may be provided to prevent the ultraviolet rays L radiated from the light source 240 from being incident on the outside of the radiation area R1. Also, the light blocking member 280 may be provided to allow passage of air flowing along the second passage P2.

For example, the light blocking member 280 may include a plurality of grille portions 281 and an air ventilation portion 282 formed between the plurality of grille portions 281 and configured to be penetrated to allow passage of air in the second passage P2. Air introduced into the second housing 210 through the second suction port 211 may be introduced into the radiation area R1 through the air ventilation portion 282 of the first light blocking member 280a, discharged from the radiation area R1 through the air ventilation portion 282 of the second light blocking member 280b and the third light blocking member 280c, and flow to the second discharge port 212.

Each of the plurality of grille portions 281 may be formed so that one surface 281a facing the grille portion 281 adjacent thereto is inclined relative to the one direction in which the radiation area R1 extends. In other words, each of the plurality of grille portions 281 may extend in a direction inclined relative to the one direction in which the radiation area R1 extends. Hereinafter, the one surface of each of the plurality of grille portions 281 that faces the grille portion 281 adjacent thereto will be referred to as an inclined surface 281a.

Since the inclined surface 281a is formed to be inclined relative to the direction in which the radiation area R1 extends, in order to correspond thereto, the air ventilation portion 282 may also be formed to be inclined relative to the direction in which the radiation area R1 extends.

A portion of the ultraviolet rays L radiated from the light source 240 may be incident toward the light blocking member 280. A rectilinear propagation path of the ultraviolet rays L incident toward the light blocking member 280 may be blocked by the inclined surface 281a. The ultraviolet rays L incident on the inclined surface 281a may be absorbed by the inclined surface 281a or reflected back toward the radiation area R1.

The light blocking member 280 may be configured to include an opaque material so that the ultraviolet rays L cannot pass therethrough. The ultraviolet rays L incident on the light blocking member 280 may be absorbed or reflected by the light blocking member 280. For example, light reflectivity of the light blocking member 280 may be configured to be lower than light reflectivity of the reflective cover 270, but the present disclosure is not limited thereto.

By such a configuration, the light blocking member 280 may allow passage of air flowing along the second passage P2 but prevent the ultraviolet rays L radiated from the light source 240 from being incident on the outside of the radiation area R1.

The light blocking member 280 may include a light source support portion 283 provided to support the light source 240. The light source support portion 283 may be formed so that one portion of the light source 240 passes therethrough. More specifically, the light source support portion 283 may be formed to be penetrated by an end of the lamp body 241 of the light source 240. The light source fixing member 290 provided to fix the electrode portion 242 may be accommodated in the light source support portion 283. The light source support portion 283 may support the light source fixing member 290 and, accordingly, support the light source 240. That is, the light blocking member 280 may be provided to also perform a function of supporting or fixing the light source 240.

The above-described grille portion 281 and air ventilation portion 282 may be formed along the circumference of the light source support portion 283. The grille portion 281 and the air ventilation portion 282 may be provided to surround the light source support portion 283.

However, the present disclosure is not limited thereto, and the light blocking member 280 may be formed to have various other shapes.

The light source fixing member 290 may be covered by the light blocking member 280. Specifically, the light source fixing member 290 may be covered by the light source support portion 283 in the one direction (that is, the direction of extension of the light source 240, the radiation area R1, and the like). For example, the light blocking member 280 may cover the light source fixing member 290 in a direction toward the radiation area R1. Accordingly, the light source fixing member 290 may be protected from the ultraviolet rays L radiated from the light source 240.

By the above configuration, at least one portion of the ultraviolet rays L radiated from the light source 240 may be reflected by the reflective cover 270, and organic matter may be removed from air flowing along the radiation area R1. Also, at least another portion of the ultraviolet rays L radiated from the light source 240 may be incident toward the light blocking member 280 and may be absorbed or reflected by the light blocking member 280.

However, the above-described features of the configurations provided in the light source 240 or the radiation area R1 are only some examples of the configuration for removing organic matter in the second passage using the light source radiating ultraviolet rays in the air cleaner according to the spirit of the present disclosure. The spirit of the present disclosure is not limited to the above description.

For example, the light source provided in the second passage P2 may be configured as a point light source by a light emitting diode (LED). Alternatively, for example, the light source provided in the second passage P2 may be configured by a plurality of LEDs extending in one direction.

Also, for example, the light source, the radiation area, the reflective cover, and the like provided in the second passage P2 may not extend in parallel to the one direction. In such a case, the light source may be disposed in various other ways to radiate ultraviolet rays to the radiation area, and the reflective cover may be disposed in various other ways to uniformly radiate light to the radiation area. Here, the light blocking member configured to prevent the ultraviolet rays radiated from the light source from being incident on the outside of the radiation area may be provided on at least one side of the radiation area.

FIG. 12 is a view illustrating a bottom of a second air cleaning unit and a perspective appearance of a first air cleaning unit of the air cleaner according to one embodiment of the present disclosure. FIG. 13 is a view illustrating a base cover, a base holder, a first upper cover, and a coupling duct of the air cleaner according to one embodiment of the present disclosure. FIG. 14 is a cross-sectional perspective view illustrating a coupled state of the base cover, the base holder, the first upper cover, and the coupling duct shown in FIG. 13. FIG. 15 is an enlarged cross-sectional view illustrating an enlarged cut-out of a partial configuration of the air cleaner according to one embodiment of the present disclosure.

Referring to FIGS. 12 to 15, the first air cleaning unit 10 may include the coupling duct 30 positioned at the upper portion of the first housing 110. The coupling duct 30 may be located on the lower side of the first upper cover 115 and the first discharge port cover 116.

The coupling duct 30 may include a coupling plate 32 and a first unit coupler 31 protruding upward from the coupling plate 32. The coupling plate 32 may extend in a circumferential direction. The first unit coupler 31 may protrude upward from the coupling plate 32.

The first unit coupler 31 may include a first unit coupling hole 31a. The first unit coupler 31 may be disposed on a lower side of a second unit coupler (230 in FIG. 6). The first unit coupler 31 may be coupled to the second unit coupler 230.

The coupling plate 32 may include an insertion hole 35 extending in a circumferential direction. The insertion hole 35 may be provided in plural, and may be provided as holes through which coupling protrusions 45 of a base holder 42 are inserted.

The insertion hole 35 may extend in a circumferential direction such that the base holder 42 and the coupling plate 32 may be coupled to each other as the coupling protrusion 45 rotates clockwise. The coupling plate 32 may include a fixing portion 36 to restrict an upward movement of the coupling protrusion 45 inserted into the insertion hole 35. The fixing portion 36 may be provided to cover the upper side of the coupling protrusion 45. Since the structure restricts the upward movement of the coupling protrusion 45 inserted into the insertion hole 35, the coupling strength between the coupling plate 32 and the base holder 42 may be increased.

The coupling base 40 may include a base cover 43 having a hollow and the base holder 42 supporting the base cover 43. When the coupling base 40 is coupled to the coupling duct 30, the second air cleaning unit 20 and the first air cleaning unit 10 may be coupled to each other, thus allowing the second air cleaning unit 20 to be supported by the first air cleaning unit 10. In addition, when the coupling base 40 is separated from the coupling duct 30, the second air cleaning unit 20 may be supported by the floor.

The coupling base 40 may include a coupling base hole 40a, and the coupling base hole 40a may be configured to allow the first unit coupler 31 to be inserted thereinto.

The base holder 42 may be disposed on the lower side of the second housing 210 and configured to separably coupled to the coupling duct 30. The base holder 42 may include a guide hole 41 formed on a guide surface 42a. The guide hole 41 may communicate with the second suction hole 211.

The guide surface 42a may be formed to widen toward the upper side. The guide surface 42a may be formed to slope outwardly of the second housing 210 in an upward direction. The guide surface 42a may extend in a circumferential direction to surround the coupling base hole 40a. Such a structure is provided such that, when the coupling base 40 is coupled to the coupling duct 30, a portion of the airflow discharged through the first discharge port (112 in FIG. 17) is guided by the guide surface 42a and discharged to the outside of the second housing 210.

The base holder 42 may include the guide surface 42a forming the guide hole 41. The base cover 43 may cover an upper side of the base holder 42. The base cover 43 may be connected to an upper end 42aa of the guide surface 42a. The base cover 43 may be provided in a shape of a circular plate having a hollow. According to the configuration, parts of the base holder 42 or the coupling plate 32 may be covered, and the appearance aesthetics may be improved.

The base holder 42 may be provided in a shape of a circular plate having a hollow. The base holder 42 may include the guide surface 42a protruding downward from the edge of the base cover 43, and the guide hole 41 may extend in the upper-lower direction of the guide surface 42a from a lower end 42ab of the guide surface 42a toward the base cover 43. Since the upper end 42aa of the guide surface 42a may be disposed above and spaced apart from the lower end 42ab of the guide surface 42a, a first upper end 41a of the guide hole 41 positioned on the guide surface 42a may also be located above and spaced apart from the floor. To space the first upper end 41a of the guide hole 41 apart from the floor is to facilitate intake of external air into the second housing 210 as the second air cleaning unit 20 separated from the first air cleaning unit 10 is located on the floor side.

The guide hole 41 may be provided such that outside air flows into the second passage (P2 in FIG. 21) as the second air cleaning unit 20 is separated from the first air cleaning unit 10. According to the structure, even when the coupling plate 32 and the base holder 42 are separated from each other, outside air may be introduced into the second suction port 211 through the guide hole 41, and thus the second air cleaning unit 20 may operate independent of the first air cleaning unit 10.

On the other hand, the guide surface 42a of the base holder 42 may be formed to widen in a direction toward an outer edge 43a of the base cover 43. The base cover 43 may include the outer edge 43a and an inner edge 43b. Since the guide surface 42a has a shape sloping upward, a plurality of the guide holes 41 may be provided, and each may extend in the upper-lower direction along the extension direction of the guide surface 42a. Such a structure allows a greater amount of outside air to be introduced into the second housing 210 through the guide hole 41 even when the coupling base 40 is supported by the floor.

The base holder 42 may include a lower surface 42b disposed on a radially inner side of the guide surface 42a and disposed above and spaced apart from the lower end 42ab of the guide surface 42a. The lower surface 42b may have a hollow. The lower surface 42b may extend along the circumferential direction in the horizontal direction.

The base holder 42 may include a connection surface 42c extending from the lower end 42ab of the guide surface 42a to the lower surface 42b. The connection surface 42c may extend in a vertical direction while extending in a circumferential direction. The connection surface 42c may be a portion supported by the coupling duct 30 when the base holder 42 is coupled to the coupling plate 32. The connection surface 42c may be formed to slope, narrowing in an upward direction. The guide hole 41 may also be provided in plural even on the connection surface 42c and extend along the connection surface 42c. The guide hole 41 may extend along the guide surface 42a and the connection surface 42c. According to the structure, the first upper end 41a of the guide hole 41 provided on the guide surface 42a and a second upper end 41c of the guide hole 41 provided on the connection surface 42c separately from the first upper end 41a of the guide hole 41 may be disposed above and spaced apart from the lower end 42ab of the guide surface 42a, thereby allowing a greater amount of outside air to be introduced into the second housing 210.

The base holder 42 may include the coupling protrusion 45 protruding downward and extending in a circumferential direction. The coupling protrusion 45 may be a configuration for coupling with the coupling plate 32. The coupling protrusion 45 may be formed at a position corresponding to the position of the insertion hole 35 of the coupling plate 32.

The coupling protrusion 45 may be moved downward in alignment with the position of the insertion hole 35 to be inserted into the insertion hole 35 and rotated clockwise with respect to the coupling plate 32. The coupling protrusion 45 rotated while being inserted into the insertion hole 35 may be restricted in the upward movement by the fixing portion 36, and the coupling between the coupling plate 32 and the base holder 42 may be completed.

According to the structure, as the coupling protrusion 45 is positioned in alignment with the insertion hole 35 and rotated with respect to the coupling plate 32, coupling of the second air cleaning unit 20 and the first air cleaning unit 10 may be facilitated, and conversely, separation of the second air cleaning unit 20 and the first air cleaning unit 10 may also be facilitated. Therefore, consumer satisfaction with use may be improved.

In the above description, the coupling relationship between the coupling protrusion 45 and the insertion hole 35 has been described in detail, but the base holder 42 may include a shape of an insertion hole extending in the circumferential direction, and the coupling duct 30 may include a configuration that protrudes upward and extends in a cylindrical shape, similar to a coupling protrusion. In addition, the rotation direction for coupling with the coupling protrusion 45 is not limited to the clockwise direction as long as the base holder 42 and the coupling duct 30 are coupled to each other through insertion into the insertion hole 35.

Meanwhile, the first air cleaning unit 10 and the second air cleaning unit 20, coupled to each other, may be electrically connected to each other. More specifically, as shown in FIG. 14, the coupling duct 30 may include a first connection terminal 39, and the coupling base 40 may include a second connection terminal 49 provided to be electrically connected to the first connection terminal 39.

The first connection terminal 39 may be provided on a radially outer side of the first unit coupler 31 or on the coupling plate 32. The second connection terminal 49 may be disposed on an inner surface 42d of the base holder 42. As the coupling protrusion 45 is rotated along the insertion hole 35 while the base holder 42 is located on the upper side of the coupling plate 32, the first connection terminal 39 comes in contact with the second connection terminal 49, enabling electrical connection therebetween.

Different from the drawings, the first connection terminal 39 and the second connection terminal 49 may be configured to make a vertical contact such that the first connection terminal 39 and the second connection terminal 49 come into contact with each other by moving the second air cleaning unit 20 downward toward the first air cleaning unit 10.

Also, the second power connector (217 in FIG. 1) may be provided to be connected to the second connection terminal 49. More specifically, the second power connector 217 may be provided on the coupling base 40.

According to the structure, the coupling of the second air cleaning unit 20 and the first air cleaning unit 10 may allow the light source 240 and/or the second fan 250 to be controlled through the first air cleaning unit 10 and allow the dust collector filter 140 and/or the first fan 150 to be controlled through the second air cleaning unit 20.

In more detail, the first processor 51 to be described below may control a second fan drive 250d and/or the electric dust collector filter 142, and the second processor 55 may not control a first fan drive 150d and/or the light source 240. In addition, the disclosure is not limited thereto, and the second processor 55 may control the first fan drive 150d and/or the light source 240 (see FIG. 16).

When the second air cleaning unit 20 is separated from the first air cleaning unit 10 and separately used, the coupling base 40 may include a second pre-filter 47 separably provided on the base holder 42 or the base cover 43. The second pre-filter 47 may be provided upstream of the second suction port 211 in a direction of an airflow drawn into the second housing 210. The second pre-filter 47 is provided to prevent foreign substances (e.g., hair) having a large volume in the air outside the second housing 210 from being introduced into the second housing 210. With such a structure, the durability of the second air cleaning unit 20 may be improved. In addition, the second pre-filter 47 may also be provided inside the second housing 210.

In addition, the coupling base 40 may include a damper structure capable of physically opening and closing the second suction port 211, rather than the above-described pre-filter structure. The damper may include a damper blade configured to open and close the second suction port 211. As the damper blade closes the second suction port 211, bulky foreign substances in the air outside the second housing 210 may be filtered out, allowing only air to be drawn into the second housing 210.

Referring to FIG. 15, the air cleaner 1 according to an embodiment of the present disclosure may include the connection passage CP connecting the first passage P1 and the second passage P2. The connection passage CP may be connected between the first passage P1 and the second passage P2. The connection passage CP may branch from the first passage P1 and extend toward the second passage P2.

The connection passage CP may be provided to extend from at least a portion of the first discharge port 112 to the second suction port 211. The connection passage CP may be provided between at least a portion of the first discharge port 112 and the second suction port 211.

At least a portion of air discharged from the first discharge port 112 may be introduced into the connection passage CP. The connection passage CP may be provided such that air discharged from the first discharge port 112 and introduced into the connection passage CP flows through the second suction port 211 to the second passage P2.

The connection passage CP may be provided such that air in the first passage P1 flows into the second passage P2 when the second fan 250 is driven. For example, air introduced into the first passage P1 through the first suction port 111 when the first fan 150 and the second fan 250 simultaneously are driven may be introduced to the second passage P2 via the connection passage CP. For example, when the first fan 150 is not driven and the second fan 250 is driven, air outside the air cleaner 1 may be introduced into the first passage P1 through the first discharge port 112 by the suction force of the second fan 250, and the air introduced into the first passage P1 may be discharged through the first discharge port 112 and then introduced into the connection passage CP. The air introduced into the connection passage CP may be introduced into the second passage P2 through the second suction port 211.

The connection passage CP may extend in a direction from at least a portion of the first discharge port 112 toward the second suction port 211, for example, in an upper-lower direction as shown in FIG. 15. At least a portion of the air discharged from the first housing 110 through the first discharge port 112 may be caused to flow upward along the connection passage CP, and introduced into the second housing 210 through the second suction port 211.

The first passage P1, the second passage P2, and the connection passage CP may extend in directions parallel with each other. For example, the first passage P1, the second passage P2, and the connection passage CP may each extend in the upper-lower direction of the air cleaner 1. When the first fan 150 and the second fan 250 are simultaneously driven, at least a portion of the air introduced into the first housing 110 through the first suction port 111 may flow along the first passage P1, the connection passage CP, and the second passage P2 in the substantially parallel directions. Accordingly, the efficiency of airflow in the first air cleaning unit 10 and the second air cleaning unit 20 may be improved.

However, it is not limited thereto, and the direction in which the connection passage CP extends may vary depending on the arrangement of the first air cleaning unit 10 and the second air cleaning unit 20, the shapes of the first discharge port 112 and the second suction port 211, and the like.

The connection passage CP may be formed inside of the second unit coupler 230. The second unit coupler 230 may cover the outside of the connection passage CP. The second unit coupler 230 may cover the connection passage CP at a lateral side in the horizontal direction.

The second unit coupler 230 may guide at least a portion of the air discharged from the first discharge port 112 to flow into the second suction port 211. At least a portion of the air discharged from the first discharge port 112 may be guided to the second suction port 211 by the second unit coupler 230. The second unit coupler 230 may be provided such that air introduced into the second unit coupler 230 flows into the second housing 210 along the connection path CP.

The second unit coupler 230 may cover at least a portion of the first discharge port 112. Accordingly, at least a portion of the air discharged from the first discharge port 112 may flow into the second unit coupler 230.

The second unit coupler 230 may cover the entirety of the second suction port 211. Accordingly, all of the air flowing along the second unit coupler 230 may be introduced into the second housing 210.

The second unit coupler 230 may extend in a direction from at least a portion of the first discharge port 112 toward the second suction port 211, for example, in the upper-lower direction as shown in FIG. 15. At least a portion of the air discharged through the first discharge port 112 may be introduced into the second unit coupler 230 and flow upward, to thereby be introduced into the second housing 210 through the second suction port 211.

As for the air discharged from the first discharge port 112, at least another portion of the air other than the portion introduced into the connection passage CP may be discharged to the outside of the air cleaner 1. In other words, at least another portion of the air discharged from the first discharge port 112 may be discharged to the outside of the first air cleaning unit 10 and the second air cleaning unit 20.

The air cleaner 1 may include a discharge passage DP provided such that at least a portion of the air discharged from the first discharge port 112 is discharged to the outside of the air cleaner 1. When the first fan 150 is driven, at least a portion of the air discharged from the first discharge port 112 may flow along the discharge passage DP.

The discharge passage DP may extend from at least a portion of the first discharge port 112. The discharge passage DP may branch from the first passage P1 and extend outwardly of the air cleaner 1. A region in which the discharge passage DP branches from the first passage P1 may be located adjacent to the first discharge port 112.

The discharge passage DP may be located outside the edge of the connection passage CP. In other words, the discharge passage DP may be disposed to surround the outside of the connection passage CP. Accordingly, a portion of the air discharged through the first discharge port 112 may flow in an inward direction along the connection passage CP, and another portion of the air discharged through the first discharge port 112 may flow in an outward direction along the discharge passage DP.

The discharge passage DP may extend in a direction different from a direction in which the connection passage CP extends. For example, the connection passage CP may extend in the upper-lower direction, and the discharge passage DP may extend obliquely to have a predetermined angle with respect to the upper-lower direction.

The discharge passage DP may extend to become distant away from the connection passage CP along a direction in which the air is discharged. In other words, the discharge passage DP may be provided to discharge air in a direction away from the connection passage CP or the second unit coupler 230. For example, the discharge passage DP may extend with an upward slope as being directed toward the outer edge of the first discharge port 112.

The coupling base 40 may be provided to guide the flow of at least a portion of the air discharged from the first discharge port 112. The coupling base 40 may be provided to guide air flowing along the discharge passage DP. The coupling base 40 may guide the flow of air such that a portion of the air discharged from the first discharge port 112 but not flowing into the connection passage CP flows along the discharge passage DP. More specifically, due to the guide surface 42*a* of the base holder 42, at least a portion of the air discharged from the first discharge port 112 may be discharged to the outside of the second housing 210.

One side of the discharge passage DP may be covered by the coupling base 40. The other side of the discharge passage DP may be covered by the first housing 110, for example, the first discharge port cover 116 or the first upper cover 115.

The coupling base 40 may be disposed to face the first discharge port 112 on the outside of the first air cleaning unit 10. The coupling base 40 may cover at least a portion of the first discharge port 112. For example, the coupling base 40 may cover at least a portion of the first discharge port 112 from the upper side.

The coupling base 40 may extend in a direction corresponding to the extending direction of the first discharge port 112. For example, when the first discharge port 112 extends in the horizontal direction of the air cleaner 1, the coupling base 40 may also extend correspondingly, and thus the air flowing along the discharge passage DP may be discharged to the outside by flowing in the horizontal direction with respect to the air cleaner 1 or a direction similar thereto.

The coupling base 40 may be coupled to the first air cleaning unit 10. More specifically, the coupling base 40 may be coupled to the first housing 110. For example, the coupling base 40 may be coupled to the coupling duct 30 of the first air cleaning unit 10.

The coupling base 40 may be located outside of the second unit coupling portion 230. In other words, the coupling base 40 may be formed to surround the outside of the second unit coupling portion 230.

The air cleaner 1 may include a guide opening OP formed between the outer edge of the coupling base 40 and the outer edge of the first discharge port 112. In detail, the guide opening OP may be formed between the outer end of the coupling base 40 and the outer end of the upper cover 115. The guide opening OP may be disposed parallel to the edge of the first discharge port 112.

The discharge passage DP may extend toward the guide opening OP from at least a portion of the first discharge port 112. The first discharge port 112 may be provided at one end of the discharge passage DP, and the guide opening OP may be provided at the other end of the discharge passage DP.

When the first fan 150 and the second fan 250 are driven at the same time or only the first fan 150 is driven alone, the guide opening OP may serve as an outlet through which air from the first discharge port 112 is discharged along the discharge passage DP. When the first fan 150 is not driven and only the second fan 250 is driven alone, the guide opening OP may serve as an inlet through which external air is introduced into the discharge passage DP.

Due to the coupling base 40, air flowing toward the connection passage CP and air flowing toward the discharge passage DP may be divided from each other.

As described above, the first housing 110 may further include the first discharge port cover 116 covering the first discharge port 112. Air flowing along the first passage P1 may pass through the first discharge port cover 116 and exit from the first housing 110.

Hereinafter, an example of a specific shape of the first discharge port cover 116 will be described. The first discharge port cover 116 may cover the central portion of the upper side of the first housing 110 and the circumferential portion of the upper side of the first housing 110. When the first fan 150 is driven, at least a portion of air discharged from the first discharge port 112 may pass through a penetrating shape of the first discharge port cover 116 and flow into the discharge passage DP.

Meanwhile, when the first fan 150 is not driven and the second fan 250 is driven, the air outside the air cleaner 1 may flow along the guide hole 41 to be introduced into the second housing 210.

One side of the first discharge port cover 116 may be covered by the coupling base 40. For example, the coupling base 40 may cover at least a portion of the first discharge port cover 116 from the upper side.

With such a configuration, at least a portion of the air discharged from the first discharge port 112 may flow to the connection passage CP, and at least another portion of the air discharged from the first discharge port 112 may flow to the discharge passage DP.

The configuration of the first discharge port cover 116 described above is only one example of a first discharge port cover included in the air cleaner according to the aspect of the present disclosure, and the aspect of the present disclosure is not limited thereto.

FIG. 16 is a block diagram illustrating a configuration of the air cleaner according to one embodiment of the present disclosure.

Referring to FIG. 16, the air cleaner 1 according to one embodiment of the present disclosure may include the control device 50 configured to control the operation of the air cleaner 1. The control device 50 may include a processor 50*a*. The processor 50*a* may include a first processor 51 and a second processor 55.

The first processor 51 may include the first PBA 52. The second processor 55 may include the second PBA 53.

For example, the processor 50*a* may be electrically connected to each of the first fan drive 150*d*, a second fan drive 250*d*, the electric dust collector filter 142, and the light source 240. For example, the processor 50*a* may be configured to control the operation of each of the first fan drive 150*d*, the second fan drive 250*d*, the electric dust collector filter 142, and the light source 240.

The first control panel 118 and the second control panel 218 may provide a user interface for interaction with a user to the user. Although the first control panel 118 may be disposed at the upper portion of the first air cleaning unit 10, and the second control panel 218 may be disposed at the upper portion of the second air cleaning unit 20, the first control panel 118 and the second control panel 218 are not limited in position and may be provided at various other positions in the air cleaner 1.

The first control panel 118 may include a first input button 118*a* and/or a first display 118*b*.

The second control panel 218 may include a second input button 218*a* and/or a second display 218*b*.

The first control panel 118 and the second control panel 218 may be provided on the outer walls of the first housing 110 and the second housing 210, respectively, to be exposed to the outside of the first air cleaning unit 10 and the second air cleaning unit 20 when the first air cleaning unit 10 and the second air cleaning unit 20 are separated from each other.

The input buttons 118*a* and 218*a* may obtain a user input related to the operation of the air cleaner 1. For example, when the first air cleaning unit 10 and the second air cleaning unit 20 are coupled to each other. The first input button 118*a* and the second input button 218*a* may include a power button for turning the operation of the air cleaner 1 on or off, an air volume button for controlling an air volume of the air cleaner 1, and an operation mode button for selecting an operation mode of the air cleaner 1 (for example, a mode in which the operation of the first air cleaning unit 10 and the operation of the second air cleaning unit 20 are simultaneously performed (hereinafter referred to as a "first mode 1A," see FIG. 17), a mode in which only the operation of the first air cleaning unit 10 is performed (hereinafter referred to as a "second mode 1B," see FIG. 18), or a mode in which only the operation of the second air cleaning unit 20 is performed (hereinafter referred to as a "third mode 1C," see FIG. 19).

When the first air cleaning unit 10 and the second air cleaning unit 20 are separated from each other, the first input button 118*a* may include an operation mode button for selecting an operation mode of the first air cleaning unit 10, and the second input button 118*b* may include an operation mode button for selecting an operation mode of the second air cleaning unit 20.

The first input button 118*a* and the second input button 218*a* may provide an electrical signal corresponding to a user input (a user input signal) (for example, a voltage signal or a current signal) to the processor 50*a*. The processor 50*a* may identify the user input based on processing the user input signal.

The first input button 118a and the second input button 218a may include a tact switch, a push switch, a slide switch, a toggle switch, a micro-switch, or a touch switch.

The first display 118b and the second display 218b may obtain operation information of the air cleaner 1 from the processor 50a and display the operation information of the air cleaner 1.

For example, when the first air cleaning unit 10 and the second air cleaning unit 20 are coupled to each other, at least one of the first display 118b or the second display 218b may display the operation mode (the first mode 1A, the second mode 1B, the third mode 1C, or the like) of the air cleaner 1 selected by the user. At least one of the first display 118b or the second display 218b may display the air volume of the air cleaner 1. Also, at least one of the first display 118b or the second display 218b may display information on an air condition (for example, concentration of dust, a gas, organic matter, or the like in air) measured by the sensor 90.

For example, the first display 118b and the second display 218b may include a liquid crystal display (LCD) panel, an LED panel, an LED, or the like.

The first display 118b may be integrated with the first input button 118a. The second display 218b may be integrated with the second input button 118a. For example, a plurality of LEDs configured to emit light may be provided behind or inside the first input button 118a and the second input button 218a. As another example, the first control panel 118 and the second control panel 218 may include a touchscreen in which the display and a touchpad are integrated.

The sensor 90 may detect air around the air cleaner 1 and measure a condition of the air. In other words, the sensor 90 may measure a condition of air in an indoor space where the air cleaner 1 is installed.

For example, information on the air condition measured by the sensor 90 may include information on concentration of dust in air, concentration of carbon dioxide in air, concentration of other harmful gases (e.g., total volatile organic compounds (TVOC)) in air, concentration of organic matter in air, and the like.

The sensor 90 may send an electrical signal (for example, a voltage signal or a current signal) corresponding to the measured air condition (for example, concentration of dust, concentration of carbon dioxide, concentration of other harmful gases, and concentration of organic matter in air) to the processor 50a. The processor 50a may identify a condition of air around the air cleaner 1 based on the electrical signal received from the sensor 90.

The sensor 90 may be disposed in the first air cleaning unit 10. Specifically, the sensor 90 may be disposed at the first inner frame 120 and may detect outside air through the sensing hole 113a provided in the first housing 110. However, the present disclosure is not limited thereto, and the sensor 90 may be disposed in various other ways. For example, the sensor 90 may be disposed at a position adjacent to the first suction port 111 and detect air drawn into the first suction port 111. Alternatively, for example, the sensor 90 may be provided in the second air cleaning unit 20 and detect outside air. Alternatively, for example, the sensor 90 may be provided inside the second air cleaning unit 20 and detect air in the second passage P2.

Alternatively, for example, the sensor 90 may be configured as a flow sensor (not illustrated) configured to detect a flow rate or flow velocity of air flowing along the second passage P2. The flow sensor may be provided inside the second air cleaning unit 20 and configured to output an electrical signal corresponding to the flow rate or flow velocity of air flowing along the second passage P2. For example, the flow sensor may be disposed inside the radiation area R1 and configured to output an electrical signal corresponding to a flow rate or flow velocity of air flowing along the radiation area R1. The processor 50a may be configured to, based on a signal output from the flow sensor, determine the flow rate or flow velocity of air flowing along the second passage P2.

Alternatively, for example, the sensor 90 may be configured as a flow sensor (not illustrated) configured to detect a flow rate or flow velocity of air flowing along the connection passage CP. The flow sensor may be provided inside the coupling duct 30 and configured to output an electrical signal corresponding to the flow rate or flow velocity of air flowing along the connection passage CP. The processor 50a may be configured to, based on a signal output from the flow sensor, determine the flow rate or flow velocity of air flowing along the connection passage CP.

The first air cleaning unit 10 may include the first fan drive 150d electrically connected to the first fan 150. The first fan drive 150d may receive an electrical signal relating to driving of the first fan 150 from the processor 50a. The first fan drive 150d may control the driving of the first fan 150 based on the electrical signal received from the processor 50a.

The second air cleaning unit 20 may include the second fan drive 250d electrically connected to the second fan 250. The second fan drive 250d may receive an electrical signal relating to driving of the second fan 250 from the processor 50a. The second fan drive 250d may control the driving of the second fan 250 based on the electrical signal received from the processor 50a.

A communication module 60 may exchange data with external devices such as a server and/or a user device according to control of the processor 50a.

The communication module 60 may include a wired communication module 61 configured to exchange data with the external devices via a wire and a wireless communication module 62 configured to wirelessly exchange data with the external devices.

The wired communication module 61 may connect to a wired communication network and communicate with the external devices through the wired communication network. For example, the wired communication module 61 may connect to the wired communication network through the Ethernet (based on IEEE 802.3) and receive data from the external devices through the wired communication network.

The wireless communication module 62 may wirelessly communicate with a base station or an access point (AP) and may connect to the wired communication network through the base station or AP. The wireless communication module 62 may also communicate with the external devices connected to the wired communication network via the base station or AP. For example, the wireless communication module 62 may wirelessly communicate with the AP using WiFi™ (based on IEEE 802.11) or may communicate with the base station using Code-Division Multiple Access (CDMA), Wideband Code Division Multiple Access (WCDMA), Global System for Mobile Communications (GSM), Long Term Evolution (LTE), Wireless Broadband Internet (WiBro), or the like. The wireless communication module 62 may also receive data from the external devices via the base station or AP.

Further, the wireless communication module 62 may directly communicate with the external devices. For example, the wireless communication module 62 may wirelessly receive data from the external devices using WiFi™, Bluetooth™ (based on IEEE 802.15.1), ZigBee™ (based on IEEE 802.15.4), or the like.

In this way, the communication module 60 may exchange data with the external devices. The communication module 60 may transmit data received from the external devices to the processor 50a and may send data received from the processor 50a to the external devices.

The processor 50a may generate a control signal for controlling the operation of the air cleaner 1. The first processor 51 may include a first memory 51a configured to recall and/or store a program and data for generating the control signal. The second processor 55 may include a second memory 55a configured to recall and/or store a program and data for generating the control signal. The first memory 51a may be integrally provided with the first processor 51 or separately provided from the first processor 51.

The second memory 55a may be provided integrally with the second processor 55 or may be provided separately from the second processor 55.

When the first air cleaning unit 10 and the second air cleaning unit 20 are coupled to each other, the first processor 51 may be configured to apply power to at least one of the dust collection filter 140 or the light source 240. As the coupling base 40 is coupled to the coupling duct 30, the second processor 55 may be configured to apply power to at least one of the dust collector filter 140 or the light source 240.

As the first air cleaning unit 10 and the second air cleaning unit 20 are separated from each other, the first processor 51 may be configured to apply power to the dust collector filter 140. As the first air cleaning unit 10 and the second air cleaning unit 20 are separated from each other, the second processor 55 may be configured to apply power to the light source 240.

The processor 50a may process data and/or a signal according to the program stored in the memories 51a and 55a and may provide a control signal to each configuration of the air cleaner 1 based on a processing result.

The processor 50a may receive an electrical signal indicating a user input on the control panels 118 and 218 and an electrical signal indicating an output value of the sensor 90 relating to an air condition. The processor 50a may, based on processing the electrical signals, identify the user input and the measured air condition.

The processor 50a may determine driving of the air cleaner 1 based on the user input on the control panels 118 and 218, the communication data of the communication module 60, or the output value of the sensor 90.

For example, in a case in which the user inputs a selected operation mode among the operation modes of the air cleaner 1 (the first mode 1A, the second mode 1B, the third mode 1C, and the like) using the control panels 118 and 218 or an external device performing communication with the communication module 60 while the first air cleaning unit 10 and the second air cleaning unit 20 are coupled to each other, the processor 50a may determine driving of the first air cleaning unit 10 and the second air cleaning unit 20 that corresponds to the selected operation mode.

For example, in a case in which the user inputs an operation mode of the first air cleaning unit 10 using the first control panel 118 or an external device that communicates with the communication module 60 while the first air cleaning unit 10 and the second air cleaning unit 20 are separated from each other, the processor 50a may determine to drive the first air cleaning unit 10. In addition, in a case in which the user inputs an operation mode of the second air cleaning unit 20 using the second control panel 218 or an external device that communicates with the communication module, the processor 50a may determine to drive the second air cleaning unit 20.

For example, in a case in which the user inputs a selected air volume using the control panels 118 and 218 or an external device performing communication with the communication module 60, the processor 50a may determine a rotational speed of the first fan 150 and/or the second fan 250 that corresponds to the selected air volume.

For example, the processor 50a may identify concentration of dust, a gas, or the like in air that is measured by the sensor 90 and determine the rotational speed of the first fan 150 and/or the second fan 250 for providing a target air volume according to the concentration of the dust, gas, or the like.

The processor 50a may store a table including data relating to concentration of dust, a gas, or the like in air, data relating to a target air volume of the air cleaner 1 corresponding thereto, and data relating to a rotational speed of the first fan 150 and the second fan 250 corresponding thereto. Using the table, the processor 50a may determine an air volume of the air cleaner 1 that corresponds to the measured concentration of the dust, gas, or the like in the air and may determine the rotational speed of the first fan 150 and the second fan 250.

For example, the processor 50a may identify concentration of organic matter in air that is measured by the sensor 90 and may determine an operation mode of the air cleaner 1 that corresponds to the concentration of the organic matter. For example, the processor 50a may determine the first mode 1A as the operation mode of the air cleaner 1 in a case in which the concentration of the organic matter in the air is higher than a first concentration value. The processor 50a may determine the second mode 1B as the operation mode of the air cleaner 1 in a case in which the concentration of the organic matter in the air is lower than the first concentration value and higher than a second concentration value. The processor 50a may determine the third mode 1C as the operation mode of the air cleaner 1 in a case in which the concentration of the organic matter in the air is lower than the second concentration value.

The processor 50a may store a table including data relating to concentration of organic matter in air and the operation modes of the air cleaner 1 corresponding thereto. Using the table, the processor 50a may determine an operation mode of the air cleaner 1 that corresponds to the measured concentration of the organic matter in the air.

The processor 50a may, based on the user input on the control panels 118 and 218, the communication data of the communication module 60, or the output value of the sensor 90, provide a control signal for driving of the air cleaner 1 to the first fan drive 150d, the second fan drive 250d, the light source 240, the electric dust collector filter 142, and the like.

Control of each configuration by the processor 50a will be described by referring to the case in which the first air cleaning unit 10 operates as a first operation and referring to the case in which the second air cleaning unit 20 operates as a second operation.

The first processor 51 may control the first fan drive 150d to rotate the first fan 150 in the first operation. In the first operation, the first processor 51 may be configured to apply power to the electric dust collector filter 142. For example, the processor 50a may control the power supply to apply power to the electric dust collector filter 142.

The second processor 55 may control the second fan drive 250*d* to rotate the second fan 250 in the second operation. In the second operation, the second processor 55 may control the light source 240 to radiate ultraviolet rays to the radiation area R1.

However, in a state in which the first air cleaning unit 10 and the second air cleaning unit 20 are coupled to each other, the first processor 51 may control the light source 240 or the second fan drive 250*d*, and the second processor 55 may control the electric dust collector filter 142 or the first fan drive 150*d*.

The first mode 1A of the air cleaner is an operation mode in the case in which the first operation and the second operation are simultaneously performed.

For example, in the case in which the processor 50*a* determines the first mode 1A as the operation mode of the air cleaner 1, the processor 50*a* may control the first fan drive 150*d* and the second fan drive 250*d* to rotate the first fan 150 and the second fan 250, control the electric dust collector filter 142, and control the light source 240 to radiate ultraviolet rays.

The second mode 1B of the air cleaner is an operation mode in the case in which only the first operation is performed among the first operation and the second operation.

For example, in the case in which the processor 50*a* determines the second mode 1B as the operation mode of the air cleaner 1, the processor 50*a* may control the first fan drive 150*d* and the second fan drive 250*d* to rotate the first fan 150 and not rotate the second fan 250, control to operate the electric dust collector filter 142, and control the light source 240 to not radiate ultraviolet rays.

The third mode 1C of the air cleaner is an operation mode in the case in which only the second operation is performed among the first operation and the second operation.

For example, in the case in which the processor 50*a* determines the third mode 1C as the operation mode of the air cleaner 1, the processor 50*a* may control the first fan drive 150*d* and the second fan drive 250*d* to not rotate the first fan 150 and to rotate the second fan 250, control not to operate the electric dust collector filter 142, and control the light source 240 to radiate ultraviolet rays.

The configuration of the air cleaner 1 described above with reference to FIG. 16 is only one example of a configuration of the air cleaner according to the spirit of the present disclosure, and the present disclosure is not limited thereto.

FIG. 17 is a lateral cross-sectional view for describing an operation according to the first mode when the first air cleaning unit and the second air cleaning unit are coupled to each other according to one embodiment of the present disclosure.

Referring to FIG. 17, the air cleaner 1 according to one embodiment of the present disclosure may be operated in the first mode 1A in which the first air cleaning unit 10 and the second air cleaning unit 20 may be simultaneously driven. In the first mode 1A, the first air cleaning unit 10 may purify air of the first passage P1, and the second air cleaning unit 20 may purify air of the second passage P2.

In the first mode 1A, the first fan 150 and the second fan 250 may be simultaneously driven.

In the first mode 1A, the dust collector filter 140 and the light source 240 may be simultaneously driven.

In the first mode 1A, the first passage P1 may be provided such that air introduced from the first suction port 111 flows to be discharged to the first discharge port 112. For example, in the first mode 1A, air flowing along the first passage P1 may flow in the up-down direction.

In the first mode 1A, the second passage P2 may be provided such that air introduced from the second suction port 211 flows to be discharged to the second discharge port 212. For example, in the first mode 1A, air flowing along the second passage P2 may flow in the up-down direction.

In the first mode 1A, the connection passage CP may be provided such that at least one portion of air discharged from the first discharge port 112 flows to be discharged to the second suction port 211. For example, in the first mode 1A, air flowing along the connection passage CP may flow in the up-down direction. When both the first fan 150 and the second fan 250 are driven, the pressure of the airflow generated by the second fan 250 may be greater than the pressure of the airflow generated by the first fan 150. Accordingly, air from the outside of the second housing 210 may be prevented from being introduced into the second housing 210 through the guide hole (41 in FIG. 15).

In the first mode 1A, the discharge passage DP may be provided such that at least another portion of the air discharged from the first discharge port 112 flows to be discharged to the outside of the air cleaner 1.

In order to improve purification efficiency of the air cleaner 1, a flow rate of air purified by the first air cleaning unit 10 and a flow rate of air purified by the second air cleaning unit 20 need to be appropriately set. A flow rate of air flowing along the first passage P1 and a flow rate of air flowing along the second passage P2 need to be appropriately set. The flow rates may be changed according to a ratio between a flow rate of air flowing along the connection passage CP branched from the first passage P1 and a flow rate of air flowing along the discharge passage DP branched from the first passage P1.

In order to improve air sterilization efficiency according to the second air cleaning unit 20, a flow velocity of air flowing in the second passage P2 may need to be appropriately set in consideration of the quantity, wavelength, or the like of ultraviolet rays radiated from the light source 240. This is because, in a case in which the flow velocity of air flowing along the second passage P2 is too high, there is a possibility that sterilization of air by ultraviolet rays may not be sufficiently performed, and conversely, in a case in which the flow velocity of air flowing along the second passage P2 is too low, there is a possibility that air purification efficiency may be reduced.

In order to optimize the flow velocity of air flowing along the second passage P2, a flow rate of air introduced into the second passage P2 through the connection passage CP may need to be appropriately set. In order to optimize the flow rate of the air introduced into the second passage P2, a ratio between a flow rate of air flowing to the connection passage CP and a flow rate of air flowing to the discharge passage DP in the first mode 1A may need to be appropriately set.

For example, in order to improve efficiency of sterilization by ultraviolet rays radiated from the light source 240, the flow velocity of air flowing along the second passage P2 may be set to be maintained at about 0.05 CMM (Cubic Meter per Minute). The flow rate of air introduced into the second passage P2 may be set in consideration of the flow velocity of air, a cross-sectional area of the second passage P2, and the like, and for example, a flow rate of air introduced into the connection passage CP and a flow rate of air introduced into the discharge passage DP may be set to have a ratio of about 20 to 80.

The numerical values relating to the flow velocity of air, the ratio between the flow rates, and the like described above are only some examples given to describe the process of setting the flow velocity of air in the second passage P2, the ratio between the flow rates of air introduced into the connection passage CP and air introduced into the discharge passage DP, and the like in order to improve purification efficiency of the air cleaner 1 according to one embodiment of the present disclosure, and the spirit of the present disclosure is not limited thereto.

The flow velocity of air, the ratio between the flow rates, and the like in the air cleaner 1 may be set in various ways according to characteristics, such as the quantity and wavelength, of ultraviolet rays radiated from the light source 240, the length or cross-sectional area of the second passage P2, the shape of the connection passage CP and the discharge passage DP, and other features of configurations constituting the air cleaner 1.

Hereinafter, an example of a method of controlling the operation of the air cleaner 1 in order to efficiently purify air in the first mode 1A will be described.

For example, the light source 240 of the air cleaner 1 may be configured to radiate ultraviolet rays in different quantities of various intensities such as a first quantity and a second quantity whose intensity is higher than the first quantity. The "first quantity," "second quantity," and the like mentioned herein are only terms used to compare the sizes of quantities of ultraviolet rays radiated from the light source 240, and the interpretation of the quantity of ultraviolet rays radiated from the light source 240 is not limited by expressions such as "first" and "second."

For example, the second fan 250 of the air cleaner 1 may be configured to rotate at various rotational speeds such as a first rotational speed and a second rotational speed faster than the first rotational speed.

The "first rotational speed," "second rotational speed," and the like mentioned herein are only terms used to compare the rotational speeds of the second fan 250, and the interpretation of the rotational speed of the second fan 250 is not limited by expressions such as "first" and "second."

The processor 50a of the air cleaner 1 may be configured to determine the quantity of ultraviolet rays radiated from the light source 240 and the rotational speed of the second fan 250 in order to efficiently purify air in the first mode 1A. The processor 50a may be configured to control the light source 240 based on the determined quantity of ultraviolet rays. The processor 50a may be configured to control the second fan drive 250d based on the determined rotational speed of the second fan 250.

For example, in the air cleaner 1 operated in the first mode 1A, the processor 50a which has received a user input, an output value of the sensor 90, or the like may determine to increase the flow velocity of air flowing along the second passage P2 in order to improve an air purification speed. Based on the determination, the processor 50a may control the second fan drive 250d such that the rotational speed of the second fan 250 changes from the first rotational speed to the second rotational speed.

As the flow velocity of air flowing along the second passage P2 increases, the intensity of ultraviolet rays radiated to the radiation area R1 may be required to be increased. Accordingly, the processor 50a may determine to increase the quantity of ultraviolet rays radiated to the radiation area R1 from the first quantity to the second quantity. Based on the determination, the processor 50a may control the light source 240 such that the quantity of ultraviolet rays radiated to the radiation area R1 changes from the first quantity to the second quantity.

Conversely, for example, in the air cleaner 1 operated in the first mode 1A, the processor 50a which has received a user input, an output value of the sensor 90, or the like may determine to decrease the flow velocity of air flowing along the second passage P2. Based on the determination, the processor 50a may control the second fan drive 250d such that the rotational speed of the second fan 250 changes from the second rotational speed to the first rotational speed.

As the flow velocity of air flowing along the second passage P2 decreases, the intensity of ultraviolet rays radiated to the radiation area R1 may be sufficient to purify air even when decreased. Accordingly, the processor 50a may determine to decrease the quantity of ultraviolet rays radiated to the radiation area R1 from the second quantity to the first quantity. Based on the determination, the processor 50a may control the light source 240 such that the quantity of ultraviolet rays radiated to the radiation area R1 changes from the second quantity to the first quantity.

Although description has been given above while assuming that the rotational speed of the second fan 250 is determined and then the quantity of ultraviolet rays radiated from the light source 240 is determined to correspond thereto, the present disclosure is not limited thereto. The processor 50a may also determine the quantity of ultraviolet rays radiated from the light source 240 and then determine the rotational speed of the second fan 250 to correspond thereto. Here, determining of the rotational speed of the second fan 250 and determining of the quantity of ultraviolet rays radiated from the light source 240 may be performed almost simultaneously.

The rotational speed of the second fan 250 may be configured to have discontinuous values. Alternatively, the rotational speed of the second fan 250 may be configured to have continuous values.

The quantity of ultraviolet rays radiated from the light source 240 may be configured to have discontinuous values. Alternatively, the quantity of ultraviolet rays radiated from the light source 240 may be configured to have continuous values.

Alternatively, for example, the first fan 150 may be configured to rotate at various rotational speeds. As described above in the example in which the rotational speed of the second fan 250 changes, the processor 50a may be configured to determine the quantity of ultraviolet rays radiated from the light source 240 and the rotational speed of the first fan 150 in order to efficiently purify air in the first mode 1A. The processor 50a may be configured to control the light source 240 based on the determined quantity of ultraviolet rays. The processor 50a may be configured to control the first fan drive 150d based on the determined rotational speed of the first fan 150.

For example, in a case in which the rotational speed of the first fan 150 increases, the flow velocity may increase in all of the passages including the first passage P1, the connection passage CP, and the second passage P2, and accordingly, the quantity of ultraviolet rays of the light source 240 may be required to be increased. Accordingly, the processor 50a may control the first fan drive 150d such that the rotational speed of the first fan 150 increases and may control the light source 240 such that the quantity of ultraviolet rays radiated to the radiation area R1 increases.

Conversely, in a case in which the rotational speed of the first fan 150 decreases, the flow velocity may decrease in all of the passages including the first passage P1, the connection passage CP, and the second passage P2, and accordingly, the quantity of ultraviolet rays of the light source 240 may be sufficient even when decreased. Accordingly, the processor 50a may control the first fan drive 150d such that the rotational speed of the first fan 150 decreases and may control the light source 240 such that the quantity of ultraviolet rays radiated to the radiation area R1 decreases.

The processor 50*a* may be configured to determine the flow velocity of air by various configurations in order to control the fan drives 150*d* and 250*d*, the light source 240, or the like.

For example, the air cleaner 1 may include a flow sensor (not illustrated) configured to measure the flow rate or flow velocity of air, and the processor 50*a* may be configured to determine the flow rate or flow velocity of the air based on an electrical signal output from the flow sensor and, based on the determined flow rate or flow velocity of the air, control driving of each configuration of the air cleaner 1.

For example, the flow sensor may be provided in the first air cleaning unit 10 and configured to output an electrical signal that corresponds to the flow rate or flow velocity of air flowing along the first passage P1, and the processor 50*a* may be configured to, based on the electrical signal output from the flow sensor, determine the flow rate or flow velocity of the air flowing along the first passage P1. The processor 50*a* may be configured to control the first fan drive 150*d* or the light source 240 based on the determined flow rate or flow velocity of the air in the first passage P1.

For example, the flow sensor may be provided in the second air cleaning unit 20 and configured to output an electrical signal that corresponds to the flow rate or flow velocity of air flowing along the second passage P2, and the processor 50*a* may be configured to, based on the electrical signal output from the flow sensor, determine the flow rate or flow velocity of the air flowing along the second passage P2. The processor 50*a* may be configured to control the second fan drive 250*d* or the light source 240 based on the determined flow rate or flow velocity of the air in the second passage P2.

For example, the flow sensor may be configured to output an electrical signal that corresponds to the flow rate or flow velocity of air flowing along the connection passage CP, and the processor 50*a* may be configured to, based on the electrical signal output from the flow sensor, determine the flow rate or flow velocity of the air flowing along the connection passage CP. The processor 50*a* may be configured to control the second fan drive 250*d* or the light source 240 based on the determined flow rate or flow velocity of the air in the connection passage CP.

Alternatively, for example, the processor 50*a* may store a table including data relating to current/voltage input to the fan drives 150*d* and 250*d* and data relating to current/voltage input to the light source 240 corresponding thereto. The processor 50*a* may be configured to, using the table, control the fan drives 150*d* and 250*d* and the light source 240.

However, the content described above is only one of various examples of the method in which the processor 50*a* controls each configuration of the air cleaner 1 to improve air purification efficiency of the air cleaner 1 in the first mode 1A, and the spirit of the present disclosure is not limited thereto.

FIG. 18 is a lateral cross-sectional view for describing an operation according to the second mode when the first air cleaning unit and the second air cleaning unit are coupled to each other according to one embodiment of the present disclosure.

Referring to FIG. 18, the air cleaner 1 according to one embodiment of the present disclosure may be operated in the second mode 1B in which only the first air cleaning unit 10 may be driven among the first air cleaning unit 10 and the second air cleaning unit 20. In the second mode 1B, the first air cleaning unit 10 may purify air of the first passage P1, and the second air cleaning unit 20 may purify air of the second passage P2.

In the second mode 1B, only the first fan 150 may be driven among the first fan 150 and the second fan 250.

In the second mode 1B, only the dust collector filter 140 may be driven among the dust collector filter 140 and the light source 240.

In the second mode 1B, the first passage P1 may be provided such that air introduced from the first suction port 111 flows to be discharged to the first discharge port 112. For example, in the second mode 1B, air flowing along the first passage P1 may flow in the up-down direction.

In the second mode 1B, the discharge passage DP may be provided such that air discharged from the first discharge port 112 flows to be discharged to the outside of the air cleaner 1.

In the second mode 1B, air discharged from the first discharge port 112 may not flow to the second passage P2 through the connection passage CP.

In the second mode 1B, even in a case in which the first fan 150 is driven and generates pressure for an air flow, since the second fan 250 is not driven, resistance may be generated for an airflow in the second passage P2. In other words, the second fan 250 may generate pressure opposite to the pressure generated by the first fan 150 and may generate resistance in the opposite direction for air about to flow along the second passage P2.

Accordingly, although the first passage P1 and the second passage P2 are still connected by the connection passage CP, and the first housing 110 and the second housing 210 still communicate in the second mode 1B, most of the air discharged from the first discharge port 112 may flow to the discharge passage DP and not flow to the second passage P2.

In particular, in the following embodiment in which the second fan 250 is configured as a centrifugal fan, air may be more efficiently prevented from flowing from the first passage P1 to the second passage P2 while the second fan 250 is not driven.

When a direction in which the connection passage CP and the second passage P2 are connected is referred to as a first direction, and a direction of the rotating shaft of the second fan 250, that is, the second fan rotating shaft 253, is referred to as a second direction, the first direction and the second direction may be orthogonal to each other. In other words, the connection passage CP and the second passage P2 may be connected in the first direction, and the second fan 250 may have the rotating shaft parallel to the second direction orthogonal to the first direction.

The second fan 250 may be provided such that air is discharged in the direction orthogonal to the second direction, which is the direction of the second fan rotating shaft 253, toward the light source 240. The direction orthogonal to the second direction mentioned herein may be a direction corresponding to the above first direction but may also be a direction inclined to have a predetermined angle relative to the first direction.

For example, the connection passage CP and the second passage P2 may extend in the up-down direction of the air cleaner 1. The second fan 250 may have the rotating shaft parallel to the horizontal direction of the air cleaner 1. The second fan 250 may be provided such that air introduced into the second fan case 254 is discharged in the direction orthogonal to the horizontal direction toward the light source 240.

In such a case, air may flow in the up-down direction as a whole in the connection passage CP and the second passage P2, but since airflow directions in the fan inlet 254a and the fan discharge duct 254b of the second fan 250 are different from each other (see FIG. 9 and so on), resistance may be efficiently generated for air about to flow from the first passage P1 to the second passage P2.

In this way, the second fan 250 may, while driven, allow introduction of air from the first passage P1 to the second passage P2 and, while not driven, serve as a damper that prevents introduction of air from the first passage P1 to the second passage P2.

However, the present disclosure is not limited thereto, the air cleaner according to one embodiment of the present disclosure may include a separate damper configured to open and close the connection passage CP or the second passage P2. The damper may be open in the first mode 1A or the third mode 1C and may be closed in the second mode 1B.

By the above configuration, the air cleaner 1 may be operated in the second mode 1B in a case in which an air purification function can be sufficiently performed by operating only the first air cleaning unit 10 or a case in which a user wants to operate only the first air cleaning unit 10. Accordingly, an unnecessary operation of the second air cleaning unit 20 may be stopped to reduce power consumption.

Hereinafter, an example of controlling the operation of the air cleaner 1 to efficiently purify air in the second mode 1B will be described.

For example, the electric dust collector filter 142 may be configured to receive voltage/current of various sizes through the first power connector 117.

For example, the first fan 150 may be configured to rotate at various rotational speeds.

The processor 50a may be configured to determine the size of the voltage/current applied to the electric dust collector filter 142 and the rotational speed of the first fan 150 in order to efficiently purify air in the second mode 1B. The processor 50a may be configured to control the power supply based on the determined size of the voltage/current applied to the electric dust collector filter 142. The processor 50a may be configured to control the first fan drive 150d based on the determined rotational speed of the first fan 150.

For example, in a case in which the rotational speed of the first fan 150 increases, the flow velocity of air flowing along the first passage P1 may increase, and accordingly, the intensity of the voltage/current applied to the electric dust collector filter 142 may be required to be increased. Accordingly, the processor 50a may control the first fan drive 150d such that the rotational speed of the first fan 150 increases and may control such that the intensity of the voltage/current applied to the electric dust collector filter 142 increases.

Conversely, for example, in a case in which the rotational speed of the first fan 150 decreases, the flow velocity of air flowing along the first passage P1 may decrease, and accordingly, the intensity of the voltage/current applied to the electric dust collector filter 142 may be sufficient even when decreased. Accordingly, the processor 50a may control the first fan drive 150d such that the rotational speed of the first fan 150 decreases and may control such that the intensity of the voltage/current applied to the electric dust collector filter 142 decreases.

Here, for example, determining of the rotational speed of the first fan 150 and determining of the voltage/current applied to the electric dust collector filter 142 may be performed almost simultaneously.

The rotational speed of the first fan 150 may be configured to have discontinuous values. Alternatively, the rotational speed of the first fan 150 may be configured to have continuous values.

The voltage/current applied to the electric dust collector filter 142 may be configured to have discontinuous values. Alternatively, the voltage/current applied to the electric dust collector filter 142 may be configured to have continuous values.

The processor 50a may be configured to determine the flow velocity of air by various configurations in order to control the first fan drive 150d, the power supply, or the like.

For example, the air cleaner 1 may include a flow sensor (not illustrated) provided in the first air cleaning unit 10 and configured to output an electrical signal that corresponds to the flow rate or flow velocity of air flowing along the first passage P1. The processor 50a may be configured to, based on the electrical signal output from the flow sensor, determine the flow rate or flow velocity of the air flowing along the first passage P1. The processor 50a may be configured to control the first fan drive 150d based on the determined flow rate or flow velocity of the air in the first passage P1.

Alternatively, for example, the processor 50a may store a table including data relating to current/voltage input to the first fan drive 150d and data relating to current/voltage applied to the electric dust collector filter 142 corresponding thereto. The processor 50a may be configured to, using the table, control the first fan drive 150d.

However, the content described above is only one of various examples of the method in which the processor 50a controls each configuration of the air cleaner 1 to improve air purification efficiency of the air cleaner 1 in the second mode 1B, and the spirit of the present disclosure is not limited thereto.

FIG. 19 is a lateral cross-sectional view for describing an operation according to the third mode when the first air cleaning unit and the second air cleaning unit are coupled to each other according to one embodiment of the present disclosure.

Referring to FIG. 19, the air cleaner 1 according to one embodiment of the present disclosure may be operated in the third mode 1C in which only the second air cleaning unit 20 may be driven among the first air cleaning unit 10 and the second air cleaning unit 20. In the third mode 1C, the second air cleaning unit 20 may purify air of the second passage P2.

In the third mode 1C, only the second fan 250 may be driven among the first fan 150 and the second fan 250.

In the third mode 1C, only the light source 240 may be driven among the dust collector filter 140 and the light source 240.

In the third mode 1C, air may not flow along the first passage P1.

In the third mode 1C, the second passage P2 may be provided such that air introduced from the second suction port 211 flows to be discharged to the second discharge port 212. For example, in the third mode 1C, air flowing along the second passage P2 may flow in the up-down direction.

In the third mode 1C, the connection passage CP may be provided such that air introduced from the outside through the guide hole 41 flows to the second passage P2 through the second suction port 211. For example, in the third mode 1C, air flowing along the connection passage CP may flow in the up-down direction.

By the above configuration, the air cleaner 1 may be operated in the third mode 1C in a case in which an air purification function can be sufficiently performed by operating only the second air cleaning unit 20 or a case in which a user wants to operate only the second air cleaning unit 20. Accordingly, an unnecessary operation of the first air cleaning unit 10 may be stopped to reduce power consumption.

By the above configuration, the air cleaner 1 according to one embodiment of the present disclosure may drive the dust collector filter 140 provided in the first passage P1 and the light source 240 provided in the second passage P2 as necessary and may improve air purification efficiency.

Also, in the air cleaner 1 according to one embodiment of the present disclosure, since the connection passage CP and the discharge passage DP are included, passages for air purification can be configured in various ways.

Also, since the operations of the first air cleaning unit 10 and the second air cleaning unit 20 of the air cleaner 1 according to one embodiment of the present disclosure can be selectively controlled, power consumption can be reduced, and efficient operation of the air cleaner 1 may be promoted.

Hereinafter, an example of controlling the operation of the air cleaner 1 to efficiently purify air in the third mode 1C will be described.

For example, the light source 240 of the air cleaner 1 may be configured to radiate ultraviolet rays in different quantities of various intensities such as a third quantity and a fourth quantity whose intensity is higher than the third quantity. The "third quantity," "fourth quantity," and the like mentioned herein are only terms used to compare the sizes of quantities of ultraviolet rays radiated from the light source 240, and the interpretation of the quantity of ultraviolet rays radiated from the light source 240 is not limited by expressions such as "third" and "fourth."

For example, the second fan 250 of the air cleaner 1 may be configured to rotate at various rotational speeds such as a third rotational speed and a fourth rotational speed faster than the third rotational speed. The "third rotational speed," "fourth rotational speed," and the like mentioned herein are only terms used to compare the rotational speeds of the second fan 250, and the interpretation of the rotational speed of the second fan 250 is not limited by expressions such as "third" and "fourth."

The processor 50a of the air cleaner 1 may be configured to determine the quantity of ultraviolet rays radiated from the light source 240 and the rotational speed of the second fan 250 in order to efficiently purify air in the third mode 1C. The processor 50a may be configured to control the light source 240 based on the determined quantity of ultraviolet rays. The processor 50a may be configured to control the second fan drive 250d based on the determined rotational speed of the second fan 250.

For example, in the air cleaner 1 operated in the first mode 1A, the processor 50a may control the second fan drive 250d such that the second fan 250 rotates at the third rotational speed. Also, in the air cleaner 1 operated in the first mode 1A, the processor 50a may control the light source 240 such that the third quantity of ultraviolet rays is radiated from the light source 240.

Here, even in a case in which the operation mode of the air cleaner 1 is changed from the first mode 1A to the third mode 1C, when the rotational speed of the second fan 250 is maintained, there is a possibility that the flow rate of air flowing along the second passage P2 may be decreased and air purification efficiency may be reduced.

Accordingly, when the operation mode of the air cleaner 1 is changed from the first mode 1A to the third mode 1C, the processor 50a may determine to increase the flow rate and flow velocity of air flowing along the second passage P2. Based on the determination, the processor 50a may control the second fan drive 250d such that the rotational speed of the second fan 250 changes from the third rotational speed to the fourth rotational speed.

As the flow velocity of air flowing along the second passage P2 increases, the intensity of ultraviolet rays radiated to the radiation area R1 may be required to be increased. Accordingly, the processor 50a may determine to increase the quantity of ultraviolet rays radiated to the radiation area R1 from the third quantity to the fourth quantity. Based on the determination, the processor 50a may control the light source 240 such that the quantity of ultraviolet rays radiated to the radiation area R1 changes from the third quantity to the fourth quantity.

Conversely, for example, when the operation mode of the air cleaner 1 is changed from the third mode 1C to the first mode 1A, the processor 50a may determine to decrease the flow velocity of air flowing along the second passage P2. Based on the determination, the processor 50a may control the second fan drive 250d such that the rotational speed of the second fan 250 changes from the fourth rotational speed to the third rotational speed.

As the flow velocity of air flowing along the second passage P2 decreases, the intensity of ultraviolet rays radiated to the radiation area R1 may be sufficient for air purification even when decreased. Accordingly, the processor 50a may determine to decrease the quantity of ultraviolet rays radiated to the radiation area R1 from the fourth quantity to the third quantity. Based on the determination, the processor 50a may control the light source 240 such that the quantity of ultraviolet rays radiated to the radiation area R1 changes from the fourth quantity to the third quantity.

Although description has been given above while assuming that the rotational speed of the second fan 250 is determined and then the quantity of ultraviolet rays radiated from the light source 240 is determined to correspond thereto, the present disclosure is not limited thereto. The processor 50a may also determine the quantity of ultraviolet rays radiated from the light source 240 and then determine the rotational speed of the second fan 250 to correspond thereto. Here, determining of the rotational speed of the second fan 250 and determining of the quantity of ultraviolet rays radiated from the light source 240 may be performed almost simultaneously.

The rotational speed of the second fan 250 may be configured to have discontinuous values. Alternatively, the rotational speed of the second fan 250 may be configured to have continuous values.

The quantity of ultraviolet rays radiated from the light source 240 may be configured to have discontinuous values. Alternatively, the quantity of ultraviolet rays radiated from the light source 240 may be configured to have continuous values.

The processor 50a may be configured to determine the flow velocity of air by various configurations in order to control the second fan drive 250d, the light source 240, or the like.

For example, the air cleaner 1 may include a flow sensor (not illustrated) configured to measure the flow rate or flow velocity of air, and the processor 50a may be configured to determine the flow rate or flow velocity of the air based on an electrical signal output from the flow sensor and, based on the determined flow rate or flow velocity of the air, control driving of each configuration of the air cleaner 1.

For example, the flow sensor may be provided in the second air cleaning unit 20 and configured to output an electrical signal that corresponds to the flow rate or flow velocity of air flowing along the second passage P2, and the processor 50a may be configured to, based on the electrical signal output from the flow sensor, determine the flow rate or flow velocity of the air flowing along the second passage P2. The processor 50a may be configured to control the second fan drive 250d or the light source 240 based on the determined flow rate or flow velocity of the air in the second passage P2.

For example, the flow sensor may be configured to output an electrical signal that corresponds to the flow rate or flow velocity of air flowing along the connection passage CP, and the processor 50a may be configured to, based on the electrical signal output from the flow sensor, determine the flow rate or flow velocity of the air flowing along the connection passage CP. The processor 50a may be configured to control the second fan drive 250d or the light source 240 based on the determined flow rate or flow velocity of the air in the connection passage CP.

Alternatively, for example, the processor 50a may store a table including data relating to current/voltage input to the second fan drive 250d and data relating to current/voltage input to the light source 240 corresponding thereto. The processor 50a may be configured to, using the table, control the second fan drive 250d and the light source 240.

However, the content described above is only one of various examples of the method in which the processor 50a controls each configuration of the air cleaner 1 to improve air purification efficiency of the air cleaner 1 in the third mode 1C, and the spirit of the present disclosure is not limited thereto.

Meanwhile, embodiments in which the flow rate and flow velocity of air flowing along the first passage P1, the second passage P2, and the connection passage CP are controlled by the rotational speed of the fans 150 and 250 (further, whether the fans 150 and 250 are rotated or stopped) have been described above with reference to FIGS. 17 to 19.

However, the spirit of the present disclosure is not limited thereto, and the flow rate and flow velocity of air flowing along the first passage P1, the second passage P2, and the connection passage CP may be controlled by various other methods corresponding to the operation modes 1A, 1B, and 1C of the air cleaner 1.

Meanwhile, the rotational speeds of the first fan 150 and the second fan 250 when the first air cleaning unit 10 and the second air cleaning unit 20 are coupled to each other may be configured to be different from those when the first air cleaning unit 10 and the second air cleaning unit 20 are separated from each other.

For example, the rotational speeds of the first fan 150 and the second fan 250 when the first air cleaning unit 10 and the second air cleaning unit 20 are coupled to each other, and the rotational speeds of the first fan 150 and the second fan 250 when the first air cleaning unit 10 and the second air cleaning unit 20 are separated from each other may be provided to correspond with Table 1 below.

TABLE 1

| | Rotational speed (RPM) of Second Fan | | |
| | Strong | Medium | weak |
| separated | 500 | 375 | 250 |
| coupled | 700 | 525 | 350 |

<Table 1. Rotational Speed of the Second Fan when the First Air Cleaning Unit and the Second Air Cleaning Unit are Coupled or Separated>

According to Table 1, in response to the first fan 150 being driven while the first air cleaning unit 10 and the second air cleaning unit 20 are coupled to each other, the second fan 250 may be selectively driven at 700 (Revolutions Per Minute) RPM, 525 RPM, or 350 RPM.

In this case, the rotational speed of the second fan 250 for "strong" is a rotational speed for securing the time exposed to the light source 240 to achieve a 99% sterilizing power of the air passing through the second air cleaning unit 20.

The rotational speed of the second fan 250 for "medium" may be a rotational speed corresponding to 75% of the rotational speed for "strong". The rotational speed of the second fan 250 for "weak" may be a rotational speed corresponding to 50% of the rotational speed for "strong".

In this way, when the rotational speed of the second fan 250 is "medium" or "weak", the sterilizing power of the air passing through the second air cleaning unit 20 may reach 99% or more. In particular, when the rotational speed of the second fan 250 is "weak", the sterilizing power of air may reach 99.9%.

Meanwhile, the second fan 250 when the first air cleaning unit 10 and the second air cleaning unit 20 are separated from each other may be driven at a rotational speed lower than that when the first air cleaning unit 10 and the second air cleaning unit 20 are coupled to each other For example, when the first air cleaning unit 10 and the second air cleaning unit 20 are separated from each other, the second fan 250 may be driven at 500 RPM, 375 RPM, or 250 RPM.

Even when the first air cleaning unit 10 and the second air cleaning unit 20 are separated from each other, the rotational speed of the second fan 250 for "medium" and the rotational speed of the second fan 250 for "weak" may be a rotational speed corresponding to 75% of the rotational speed for "strong" and a rotational speed corresponding to 50% of the rotational speed for "strong".

For example, when the first air cleaning unit 10 and the second air cleaning unit 20 are separated from each other, the rotational speed of the second fan 250 may be adjusted to 500 RPM for strong, 375 RPM for medium, and 250 RPM for weak, to achieve a sterilization power greater than or equal to 99% for the air passing through the second air cleaning unit 20.

For example, in order to achieve a 99% sterilization power of air passing through the air cleaner 1 when the first air cleaning unit 10 and the second air cleaning unit 20 are coupled to each other, there is a need to adjust the rotational speed of the second fan 250 such that a portion of air discharged through the first air cleaning unit passes through the second air cleaning unit 20. When the second fan 250 is not operated while the first fan 150 is in operation, most of the air passing through the first air cleaning unit 10 may be discharged to the outside of the second air cleaning unit 20 without flowing into the second air cleaning unit 20. Therefore, in order that a portion of the air passing through the first air cleaning unit 10 is guided to the second air cleaning unit 20 when the first air cleaning unit 10 and the second air cleaning unit 20 are coupled to each other, there is a need to properly adjust the rotational speed of the second fan 250, and the rotational speed of the second fan 250 may be adjusted to strong (700 RPM), medium (525 RPM), or weak (350 RPM).

The reason for setting the rotational speed of the second fan 250 when the first air cleaning unit 10 and the second air cleaning unit 20 are coupled to each other to be higher than that when the second air cleaning unit 20 is separated from the first air cleaning unit 10 is that an insufficient rotational speed when the first air cleaning unit 10 and the second air cleaning unit 20 may cause most of the air discharged through the first discharge port 112 to be discharged to the outside of the second housing 210 without being guided to the inside of the second housing 210. That is, the rotational speed is adjusted to allow a portion of the air discharged through the first air cleaning unit 10 to pass through the second air cleaning unit 20 such that the time for exposure to the light source 240 is secured to achieve a 99% sterilization of the air discharged through the air cleaner 1.

For the rotational speed described above, the processor 50a or the second processor 55 may determine whether the first air cleaning unit 10 and the second air cleaning unit 20 are coupled to or separated from each other through the total power consumption of the air cleaner 1, and accordingly, control the second fan 250 to be driven at the rotational speeds shown in Table 1.

Meanwhile, "strong", "medium", and "weak" for the rotational speed of the second fan 250 may be determined by a user or predetermined by the processor 50a or the second processor 55.

While the above describes the rotational speeds of the second fan 250 according to manual control, the second fan 250 may also be driven to correspond with the rotational speeds shown in Table 2 below when the second air cleaning unit 10 and the second air cleaning unit 20 are coupled to or separated from each other.

TABLE 2

| Rotational speed (RPM) according to Sensing Flow Velocity | | |
| --- | --- | --- |
| | Strong | Medium | Weak |
| 2 m/s | 500 | 375 | 250 |
| 1 m/s | 700 | 525 | 350 |
| 0.5 m/s | 1000 | 750 | 500 |

<Table 2. Rotational Speed of the Second Fan According to the Flow Velocity when the First Air Cleaning Unit and the Second Air Cleaning Unit are Coupled to or Separated from Each Other>

Since at least one of the first air cleaning unit 10 or the second air cleaning unit 20 may be provided with a flow sensor, the flow velocity of the air drawn through the first suction port 111 or the second suction port 211 may be detected by the flow sensor.

However, the flow sensor described below may be provided adjacent to the second suction port 211 of the second air cleaning unit 20, and measure the speed of the airflow introduced into the second housing 210 through the second suction port 211, and accordingly, the rotational speed of the second fan 250 may be adjusted. To this end, the flow sensor of the second air cleaning unit 20 may be provided on the second passage P2 to be adjacent to the second suction port 211.

For example, when the first air cleaning unit 10 and the second air cleaning unit 20 are coupled to each other, the airflow introduced through the second suction port 211 may have a speed of 1 m/s. When the second air cleaning unit 20 coupled to the first air cleaning unit 10 is separated from the first air cleaning unit 10, the speed of the airflow introduced through the second suction port 211 may be increased from 1 m/s to 2 m/s. Based on the speed of the airflow from 1 m/s being detected by the flow sensor as increasing from 1 m/s to 2 m/s, the processor 50a or the second processor 55 may identify that the first air cleaning unit 10 and the second air cleaning unit 20 are separated from each other.

The reason why the speed of the airflow introduced through the second suction port 211 is increased as the second air cleaning unit 20 is separated from the first air cleaning unit 10 may be that the air resistance is reduced when air is introduced into the second air cleaning unit 20.

The processor 50a or the second processor 55 may, based on the second air cleaning unit 20 being separated from the first air cleaning unit 10, control the second fan 250 to lower the rotational speed of the second fan 250 from 700 RPM to 500 RPM.

In addition, in a case in which the rotational speed of the second fan 250 while the first air cleaning unit 10 and the second air cleaning unit 20 are coupled to each other is 525 RPM or 350 RPM, the rotational speed of the second fan 250 while the second air cleaning unit 20 is separated from the first air cleaning unit 20 may be controlled to 375 RPM or 250 RPM, respectively.

For example, dust contamination of a portion through which airflow is introduced via the second suction port 211 or any other circumstances that increase the resistance of the passage may cause a decrease in the speed of the airflow, in which case the speed of the airflow detected by the flow sensor may be 0.5 m/s.

The processor 50a or the second processor 55 may, based on the speed of the airflow passing through the second suction port 211 being detected as 0.5 m/s, control the second fan 250 such that the rotational speed of the second fan 250 reaches 1000 RPM.

In addition, in a case in which the rotational speed of the second fan 250 while the first air cleaning unit 10 and the second air cleaning unit 20 are coupled to each other is 525 RPM ("medium") or 350 RPM ("weak"), the processor 50a or the second processor 55 may, in response to the increasing resistance in the passage due to a contamination of a portion adjacent to the second suction port 211 or the like, control the rotational speed of the second fan 250 to 750 RPM or 500 RPM, respectively.

As a result, even when a portion of the second suction port 211 is contaminated, the rotational speed of the second fan 250 is increased, so that the amount of air introduced into the second air cleaning unit 20 may be increased.

In Table 2, the rotational speeds of the second fan 250, "strong", "medium", and "weak" may be determined by the processor 50a or the second processor 55 or by being preset by the user.

Meanwhile, the rotational speeds of the second fan 250 in Tables 1 and 2 described above is only an example, and the second fan 250 may be controlled without being limited to the rotational speeds shown in Tables 1 and 2.

The rotational speed of the second fan 250 of the second air cleaning unit 20 may be automatically adjusted to maintain a flow velocity for securing a sterilization power greater than or equal to 99% for the air passing through the second air cleaning unit 20. With respect to a case when the first air cleaning unit 10 and the second air cleaning unit 20 are coupled to each other, a separation of the first air cleaning unit 10 and the second air cleaning unit 20 leads to a decrease in the air resistance and thus the rotational speed of the second fan 250 of the second air cleaning unit 20 may be reduced. Upon a filter contamination or a resistance on the suction passage, which causes a decrease in the flow velocity, the rotational speed of the second fan 250 of the second air cleaning unit 20 may be increased.

At least one processor may control to automatically adjust the rotational speed of the second fan 250 of the second air cleaning unit 20 based on the flow velocity detected in the coupling or separation of the second air cleaning unit 20.

Meanwhile, a control method of the above-described air cleaner may be implemented in the form of recording media storing computer-executable instructions. The instructions may be stored in the form of program codes and may, when executed by a processor, generate a program module to perform operations of the disclosed embodiments. The recording media may be implemented as computer-readable recording media.

The computer-readable recording media include all kinds of recording media in which computer-readable instructions are stored. Examples of the computer-readable recording media may include a read-only memory (ROM), a random-access memory (RAM), a magnetic tape, a magnetic disk, a flash memory, an optical data storage device, and the like.

Device-readable storage media may be provided in the form of non-transitory storage media. Here, "non-transitory" only indicates that the storage media are tangible devices and do not contain signals (e.g., electromagnetic waves), and this term does not distinguish between a case in which data is semi-permanently stored in storage media and a case in which data is temporarily stored. For example, "non-transitory storage media" may include a buffer in which data is temporarily stored.

According to one embodiment, control methods of the air cleaner according to various embodiments disclosed in this document may be provided by being included in computer program products. The computer program products may be traded between sellers and buyers as commodities. The computer program products may be distributed in the form of device-readable storage media (e.g., a compact disc read-only memory (CD-ROM)) or may be, through an application store (e.g., Play Store™) or between two different user devices (e.g., smartphones), directly distributed (e.g., downloaded or uploaded) online. In the case of online distribution, at least a part of the computer program products (e.g., downloadable apps) may be at least temporarily stored in device-readable storage media such as a server of a manufacturer, a server of an application store, or a memory of a relay server or may be temporarily generated.

FIG. 20 is a side cross-sectional view of a first air cleaning unit of an air cleaner according to one embodiment of the present disclosure. Referring to FIG. 20, the first air cleaning unit 10 may be separated from the second air cleaning unit (20 in FIG. 21) and separately supported by the floor. The first air cleaning unit 10 may operate independently.

In the first air cleaning unit 10, when the first fan 150 operates, air is introduced through the first suction port 111 and pass through the first passage P1. The air introduced into the first passage P1 may have dust collected by the dust collector filter (140 in FIG. 4), and the air, which has been cleaned by passing through the dust collector filter 140, may be discharged to the outside of the first housing 110 through the first discharge port 112.

Since the first air cleaning unit 10 is independently operable by being separated from the second air cleaning unit 20, the first air cleaning unit 10 may be used in cases such as when the consumer does not drive the second air cleaning unit 20. In this case, relatively little power may be required because the second air cleaning unit 20 is not driven. In addition, consumer convenience may be improved because only the first air cleaning unit 10 is operable when the indoor air contains a relatively large amount of dust but does not require sterilization.

FIG. 21 is a side cross-sectional view of a second air cleaning unit of an air cleaner according to one embodiment of the present disclosure. FIG. 22 is a cross-sectional view illustrating external air being introduced through a guide hole of a second air cleaning unit of an air cleaner according to one embodiment of the present disclosure.

Referring to FIGS. 21 and 22, the second air cleaning unit 20 may be separated from the first air cleaning unit 10 (see FIG. 20) and separately supported by the floor. The second air cleaning unit 10 may operate independently.

The second air cleaning unit 20 may be independently disposed on the floor by the coupling base 40 even when the coupling base 40 is separated from the coupling duct 30. As described above, the second air cleaning unit 20 may allow for introduction of outside air separately from the first air cleaning unit 10 due to the structure of the guide hole 41 of the base holder 42.

More specifically, when the second fan 250 is driven, air introduced through the guide hole 41 may be introduced into the second passage P2 through the second suction port 211. The air introduced into the second passage P2 may be sterilized by being irradiated with light from the light source 240 and discharged to the outside of the second housing 210 through the second discharge port 212.

With such a structure, only the second air cleaning unit 20 is independently usable separately from the first air cleaning unit 10, and thus less power may be required. In addition, when indoor air contains a small amount of dust and requires cleaning only for sterilization, the consumer may only use the second air cleaning unit 20, and thus the convenience of use may be improved.

FIG. 23 is a view illustrating appearances of a first air cleaning unit and a first housing cover of the air cleaner according to one embodiment of the present disclosure.

Referring to FIG. 23, the air cleaner (1 in FIG. 1) may include a first housing cover 190 configured to cover the coupling duct 30 when the first air cleaning unit 10 is used by being separated from the second air cleaning unit 20.

The first housing cover 190 may be disposed on the upper side of the first housing 110. The first housing cover 190 may be separably coupled to the coupling duct 30. The first housing cover 190 may be coupled to the coupling duct 30 when only the first air cleaning unit 10 is used, and thus aesthetics may be improved.

The first housing cover 190 may include a cover plate 191 formed in a circular shape and a cover coupling protrusion 195 protruding downward from the cover plate 191 and coupled to the coupling duct 30.

The cover coupling protrusion 195 may correspond to the shape of the coupling protrusion (45 in FIG. 13) of the base holder 42. Like the coupling protrusion 45 of the base holder 42, the cover coupling protrusion 195 may also be inserted into the insertion hole 35 and rotated clockwise such that the first housing cover 190 and the coupling duct 30 may be coupled to each other, and thus the coupling duct 30 may be prevented from being exposed to the outside.

FIG. 24 is a perspective view of a second air cleaning unit including an open type pin according to one embodiment of the present disclosure.

The second air cleaning unit 20 may include a second power connector 417 for receiving external power. Unlike the second power connector 217 shown in FIG. 1, the second power connector 417 may have an open pin shape.

Although not shown in the drawings, the shape of a first power connector for supplying external power to the first air cleaning unit 10 may also correspond to the shape of the second power connector 417.

In addition, the shape of the power connector is not limited thereto, and the configuration of the power connector may be variously provided as long as it can receive external power.

FIG. 25 is a cross-sectional view of a pogo pin structure according to one embodiment of the present disclosure.

Referring to FIG. 25, the first power connector and the second power connector may have a shape of a pogo pin. That is, as a structure for supplying external power to the first air cleaning unit 10 or the second air cleaning unit 20, the first power connector or the second power connector may have a shape of a pogo pin 617.

More specifically, the pin 617*a* may include a plunger 617*c*, a pin body 617*b*, and a pin spring 617*d* provided at an inner side of the pin body 617*b*. On the other hand, the power connector may include a pin groove 617*e*. When the pin 617*a* is inserted into the pin groove 617*e*, power may be supplied to the power connector through the plunger 617*c*.

As for the pogo pin 617, the plunger 617*c* is given an elastic force toward the pin groove 617*e* by the pin spring 617*d*, and thus power connection may be more stably established and power failure may be prevented during operation.

In addition, the structure for the first air cleaning unit 10 and the second air cleaning unit 20 to receive power is not limited thereto, and the above-described structure may also be applied to a structure in which the first air cleaning unit 10 and the second air cleaning unit 20 are coupled and electrically connected to each other.

Embodiments of the disclosure may provide an air cleaner including a first air cleaning unit including: a first housing including a first suction port and a first discharge port; a first fan disposed inside the first housing; a dust collector filter disposed inside the first housing; and a coupling duct disposed on an upper portion of the first housing. The air cleaner includes a second air cleaning unit including: a second housing including a second suction port and a second discharge port and having a shape different from a shape of the first housing; a second fan disposed inside the second housing; a light source disposed inside the second housing to emit ultraviolet rays onto air drawn into the second housing through the second suction port; and a coupling base disposed on a lower side of the second housing and configured to be coupleable to the coupling duct, the coupling base including a guide surface having a guide hole that communicates with the second suction port. The second air cleaning unit may be provided such that, when the coupling base is coupled to the coupling duct, a portion of air discharged through the first discharge port is introduced into a second passage and another portion of the air discharged through the first discharge port is guided to an outside of the second housing by the guide surface. When the coupling base is separated from the coupling duct, external air may be drawn into the second housing through the guide hole formed in the guide surface of the coupling base.

The guide hole may be provided on the guide surface of the coupling base and extend in an upper-lower direction along the guide surface.

The coupling base may have a hollow, and the guide surface may slope outwardly in an upward direction.

The coupling base may include a base holder having a hollow shape and including a coupling protrusion formed to protrude downward while extending in a circumferential direction. The coupling duct may include a coupling plate having an insertion hole into which the coupling protrusion may be inserted.

Embodiments of the disclosure may provide an air cleaner including a first housing including a first suction port and a first discharge port; a first fan formed inside the first housing; a dust collector filter formed inside the first housing; a coupling duct formed on an upper portion of the first housing; and a first processor including a first input device mounted on the first housing to be exposed to an outside, the first processor configured to control the dust collector filter. The air cleaner includes: a second housing including a second suction port and a second discharge port; a second fan formed inside the second housing; a light source disposed inside the second housing to emit ultraviolet rays onto air drawn into the second housing through the second suction port; a coupling base disposed on a lower side of the second housing and separably provided on the coupling duct; and a second processor including a second input device mounted on the second housing to be exposed to an outside, the second processor configured to control the light source. The second processor is configured to, when the coupling base is coupled to the coupling duct, apply power to at least one of the dust collector filter or the light source, and when the coupling base is separated from the coupling duct, apply power to the light source.

According to the spirit of the present disclosure, the sterilization unit is separable from the cleaning unit, and thus the sterilization unit and the cleaning unit can be separately used.

According to the spirit of the present disclosure, even when the sterilization unit is separated from the cleaning unit, external air is introduced through a separate guide hole, and thus the sterilization unit can be used independently.

According to the spirit of the present disclosure, the sterilization unit includes a controller separately from the cleaning unit, and thus the sterilization unit can be independently controllable.

According to the spirit of the present disclosure, a cover capable of covering the cleaning unit is provided even when the sterilization unit is separated from the cleaning unit, and thus the appearance of the cleaning unit can be improved.

Advantageous effects according to the spirit of the present disclosure are not limited to those mentioned above, and other unmentioned advantageous effects should be clearly understood by those of ordinary skill in the art to which the present disclosure pertains from the description above.

Specific embodiments illustrated in the drawings have been described above. However, the present disclosure is not limited to the embodiments described above, and those of ordinary skill in the art to which the disclosure pertains may make various changes thereto without departing from the gist of the technical spirit of the disclosure defined in the claims below.

The invention claimed is:

1. An air cleaner comprising:
a first housing including:
  a first suction port, and
  a first discharge port;
a first fan inside the first housing;
a dust collector filter inside the first housing;
a coupling duct on an upper portion of the first housing;
a second housing including:
  a second suction port, and
  a second discharge port;
a second fan inside the second housing;
a light source inside the second housing to emit ultraviolet rays onto air drawn into the second housing through the second suction port; and a coupling base on a lower portion of the second housing, the coupling base including a guide surface sloping outwardly of the second housing in an upward direction, wherein the coupling base is separably couplable to the coupling duct so that:

when the coupling base is coupled to the coupling duct, a portion of the air discharged through the first discharge port is guided by the guide surface to be discharged to an outside of the second housing, and when the coupling base is separated from the coupling duct, the air drawn into the second suction port is guided by the guide surface into the second housing.

2. The air cleaner of claim 1, wherein the guide surface includes a guide hole communicating with the second suction port, and when the coupling base is separated from the coupling duct, the air drawn into the second suction port passes through the guide hole.

3. The air cleaner of claim 2, wherein the guide hole extends along the guide surface of the coupling base, from a lower portion of the guide surface toward an upper portion of the guide surface.

4. The air cleaner of claim 2, wherein the coupling base includes a lower end of the guide surface configured to be supported on a floor when the coupling base is separated from the coupling duct, and the guide hole extends upward from the lower end of the guide surface.

5. The air cleaner of claim 4, wherein the coupling base includes:

a connection surface extending from the lower end of the guide surface toward an inside of the guide surface, the connection surface configured to be supported by the coupling duct when the coupling base is coupled to the coupling duct, and at least a portion of the guide hole extends along the connection surface.

6. The air cleaner of claim 1, wherein the coupling base includes:

a base holder having a hollow and including a coupling protrusion protruding downward and extending in a circumferential direction relative to the hollow, and the coupling duct includes:

a coupling plate having an insertion hole into which the coupling protrusion is insertable.

7. The air cleaner of claim 6, wherein the insertion hole extends in a circumferential direction of the coupling plate so that the coupling protrusion is rotatable with respect to the coupling plate.

8. The air cleaner of claim 7, wherein the coupling duct includes a fixing portion configured to cover an upper side of the coupling protrusion to fix the coupling protrusion when the coupling protrusion is inserted into the insertion hole and rotated.

9. The air cleaner of claim 1, further comprising:

a first housing cover configured to be couplable to the coupling duct to cover an upper side of the first housing when the coupling base is separated from the coupling duct.

10. The air cleaner of claim 9, wherein the first housing cover includes:

a cover plate, and a coupling protrusion protruding downward from the cover plate and couplable to the coupling duct.

11. The air cleaner of claim 1, further comprising:

a first air cleaning unit including:

the first housing, the first fan, the dust collector filter, the coupling duct, and a first connection terminal; and a second air cleaning unit including:

the second housing, the second fan, the light source, the coupling base, and a second connection terminal, wherein the first connection terminal and the second connection terminal are electrically connected to each other when the coupling base is coupled to the coupling duct.

12. The air cleaner of claim 11, wherein the coupling base includes an inner surface located inside of the guide surface, and on which the guide hole is formed, such that the second connection terminal is mounted on the inner surface, and the first connection terminal is disposed at the coupling duct to be connected to the second connection terminal when the coupling base is coupled to the coupling duct.

13. The air cleaner of claim 1, wherein the second housing includes a power connector configured to supply the second fan and the light source with power when the coupling base is separated from the coupling duct.

14. The air cleaner of claim 1, wherein the coupling base is configured to be supported on a floor when the coupling base is separated from the coupling duct.

15. The air cleaner of claim 1, wherein the first housing has a cylindrical shape, and the second housing has a cylindrical shape with a diameter smaller than a diameter of the first housing.

* * * * *